(12) United States Patent
Frezza et al.

(10) Patent No.: US 9,289,502 B2
(45) Date of Patent: Mar. 22, 2016

(54) PREPARATION OF OLIGO CONJUGATES

(71) Applicant: Emerald Therapeutics, Inc., Menlo Park, CA (US)

(72) Inventors: Brian M. Frezza, Redwood City, CA (US); Courtney E. Webster, Palo Alto, CA (US); Daniel J. Kleinbaum, Redwood City, CA (US)

(73) Assignee: EMERALD THERAPEUTICS, INC., Menlo Park, CA (US)

( * ) Notice: Subject to any disclaimer, the term of this patent is extended or adjusted under 35 U.S.C. 154(b) by 225 days.

(21) Appl. No.: 13/790,922

(22) Filed: Mar. 8, 2013

(65) Prior Publication Data

US 2014/0256911 A1    Sep. 11, 2014

(51) Int. Cl.
C07H 21/00 (2006.01)
C07H 21/02 (2006.01)
A61K 47/48 (2006.01)

(52) U.S. Cl.
CPC .......... *A61K 47/48092* (2013.01); *C07H 21/00* (2013.01); *Y10S 977/932* (2013.01)

(58) Field of Classification Search
CPC .......................... C07H 21/00; A61K 47/48092
USPC ................................................ 536/23.1, 25.3
See application file for complete search history.

(56) References Cited

U.S. PATENT DOCUMENTS

| | | | |
|---|---|---|---|
| 4,855,225 A | 8/1989 | Fung et al. | |
| 5,188,934 A | 2/1993 | Menchen et al. | |
| 5,539,082 A | 7/1996 | Nielsen et al. | |
| 6,238,927 B1 | 5/2001 | Abrams et al. | |
| 6,395,474 B1 | 5/2002 | Buchardt et al. | |
| 6,448,387 B1 * | 9/2002 | Slater et al. | 536/23.1 |
| 6,632,609 B2 | 10/2003 | Lizardi | |
| 7,087,770 B2 | 8/2006 | Wolff et al. | |
| 7,501,253 B2 | 3/2009 | Pourmand et al. | |
| 7,538,202 B2 | 5/2009 | Zhang et al. | |
| 7,745,594 B2 | 6/2010 | Seelig et al. | |
| 2002/0119458 A1 | 8/2002 | Suyama et al. | |
| 2002/0177133 A1 | 11/2002 | Egholm et al. | |
| 2003/0152924 A1 | 8/2003 | Ullman et al. | |
| 2005/0075792 A1 | 4/2005 | Shapiro et al. | |
| 2005/0112065 A1 | 5/2005 | Drummond et al. | |
| 2005/0112614 A1 | 5/2005 | Cook et al. | |
| 2007/0072215 A1 | 3/2007 | Seelig et al. | |
| 2007/0110798 A1 | 5/2007 | Drummond et al. | |
| 2009/0170719 A1 | 7/2009 | Kazakov et al. | |

(Continued)

FOREIGN PATENT DOCUMENTS

WO    WO 91/05060 A2    4/1991
WO    WO 2008/097929 A2    8/2008

OTHER PUBLICATIONS

Wenska et al. Nucleic Acids Research 2011, vol. 39, No. 20 pp. 9047-9059.*

(Continued)

*Primary Examiner* — Jezia Riley
(74) *Attorney, Agent, or Firm* — Sheppard Mullin Richter & Hampton LLP

(57) ABSTRACT

Conjugated molecules are prepared that comprise a predetermined number of oligo conjugation components. The conjugated molecules also may comprise one or more detectable labels. Preparation of these molecules can be implemented according to an asymmetric or a symmetric conjugation strategy.

8 Claims, 5 Drawing Sheets

Asymmetric protocol schematic

(56) References Cited

U.S. PATENT DOCUMENTS

| | | | |
|---|---|---|---|
| 2009/0191546 | A1 | 7/2009 | Zhang et al. |
| 2010/0069621 | A1 | 3/2010 | Maune et al. |
| 2011/0077169 | A1 | 3/2011 | Mckernan et al. |
| 2011/0294687 | A1 | 12/2011 | Kleinbaum et al. |
| 2012/0100633 | A1* | 4/2012 | Manetto et al. ............ 436/501 |

OTHER PUBLICATIONS

Biswas et al., "Branch Migration Through Dna Sequence Heterology", J. Mol. Biol. (1998) 279, 795-806.

Braasch et al., "Locked nucleic acid (LNA): fine-tuning the recognition of DNA and RNA", Chemistry & Biology, 8 (2001) 1-7.

Chen, et al., "Classic and contemporary approaches to modeling biochemical reactions", Genes & Development, 24: 1861-1875, (2010).

Doktycz, "Nucleic Acids: Thermal Stability and Denaturation," Encyclopedia of Life Sciences, pp. 1-18, John Wiley & Sons Ltd, Chichester. http://www.els.net [doi: 10.1038/npg.els.0003123] (Oct. 2002).

Dragulescu-Andrasi et al., "Cell-permeable GPNA with appropriate backbone stereochemistry and spacing binds sequence-specifically to RNA", Chem. Commun., 2005, 244-246.

Dragulescu-Andrasi et al., "A Simple -Backbone Modification Preorganizes Peptide Nucleic Acid into a Helical Structure", J. Am. Chem. Soc. 2006, 128, 10258-10267.

Ferrer, et al., "Synthesis of peptide nucleic acid oligomers carrying 5-methycytosine derivatives by postsynthetic substitution", Letters in Peptide Science, 7: 195-206, (2000).

Freier et al., "The ups and downs of nucleic acid duplex stability: structure-stability studies on chemically-modified DNA:RNA duplexes", Nucleic Acids Research, 1997, vol. 25, No. 22, 4429-4443.

Frezza et al., "Modular Multi-Level Circuits from Immobilized DNA-Based Logic Gates", J. Am. Chem. Soc., 2007, 129, pp. 14875-14879.

Ganesh, et al., "Peptide nucleic acids: Analogs and Derivatives", Current Organic Chemistry, 4: 931-943, (2000).

Gildea, et al., "PNA solubility enhancers", Tetrahedron Letters, 39: 7255-7258, (1998).

Harrison, et al., "Synthesis and hybridization analysis of a small library of peptide-oligonucleotide conjugates", Nucleic Acids Research, vol. 26, No. 13, pp. 3136-3145, (1998).

Hudson, et al., "Chemistry for the synthesis of nucleobase-modified peptide nucleic acid", Pure Appl. Chem., vol. 76, Nos. 7-8, pp. 1591-1598, (2004).

Imoto, et al., "Synthesis of the peptide nucleic acid (PNA) incorporating 2-amino-6-vinylpurine derivative and evaluation of the reactivity", Nucleic Acids Symposium Series, No. 52, pp. 391-392, (2008).

Kahan et al., "Towards molecular computers that operate in a biological environment", Science Direct Physica D 237, (2008) 1165-1172.

Kramer, et al., "Metal complex derivatives of peptide nucleic acids (PNA)", Metal ons in Life Sciences, 10: 319-343, (2012).

Krane et al., "Time for DNA Disclosure", Science, vol. 326, Dec. 18, 2009, 1631-1633.

Kutyavin et al., "Oligonucleotides Containing 2-Aminoadenine and 2-Thiothymine Act as Selectively Binding Complementary Agents", Biochemistry 1996, 35, 11170-11176.

Laplanche et al., "Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates," Nucleic Acids Res. 14(22):9081-9093 (1986).

Latimer et al., "Synthetic repeating sequence DNAs containing phosphorothioates: nuclease sensitivity and triplex formation," Nucleic Acids Res. 17(4):1549-1561 (1989).

Lee et al., "Chitosan: a novel platform in proton-driven DNA strand rearrangement actuation", Mol. BioSyst. 2009, 5, 391-396.

Lee, et al., "DNA sequencing with dye-labeled terminators and T7 DNA polymerase: effect of dyes and dNTPs on incorporation of dye-terminators and probability analysis of termination fragments", Nucleic Acids Research, vol. 20, No. 10, pp. 2471-2483, (1992).

Li et al., "A new class of homogeneous nucleic acid probes based on specific displacement hybridization", Nucleic Acids Research, 2002, vol. 30, No. 2, e5, 9 pages.

Luo, et al., "Synthetic DNA delivery systems", Nature Biotechnology, vol. 18, pp. 33-37, (2000).

Lusvarghi, et al., "Loop and backbone modifications of peptide nucleic acid improve G-Quadruplex binding selectivity", JACS, 131, 18415-18424, (2009).

Marks, et al., "Strain-promoted "Click" chemistry for terminal labeling of DNA", Bioconjugate Chem., 22: 1259-1263, (2011).

Maugh II, "Wolf & Lamb" Chemistry, Many useful reactions difficult to perform by conventional means can be carried out easily with polymeric reagents, Science, vol. 217, Aug. 20, 1982, pp. 719-720.

Mokhir, et al., "Conjugates of PNA with naphthalene diimide derivatives having a broad range of DNA affinities", Bioconjugate Chem., 14: 877-883, (2003).

Nielsen et al., "An Introduction to Peptide Nucleic Acid", Current Issues Molec. Biol. (1999), 1(2): 89-104.

Nishikawa, et al., "DNA computation simulator based on abstract bases", Soft Computing 5: 25-38, (2001).

Ogilvie, et al., "Synthesis of Oligoribonucleotides", J. Amer. Chem. Soc., 99: 7741-7743, (1997).

Ortega et al., "Binding Affinities of Oligonucleotides and PNAs Containing Phenoxazine and G-Clamp Cytosine Analogues Are Unusually Sequence Dependent", Organic Letters, 2007, vol. 9, No. 22, 4503-4506.

Panyutin et al., "Formation of a Single Base Mismatch Impedes Spontaneous DNA Branch Migration", J. Mol. Biol. (1993), 230, 413-424.

Panyutin et al., "The kinetics of spontaneous DNA branch migration", Proc. Natl. Acad. Sci., USA, vol. 91, pp. 2021-2025, Mar. 1994.

Percot, et al., "A hydroxyethylated cholesterol-based cationic lipid for DNA delivery: effect of conditioning", International Journal of Pharmaceuticals, 278: 143-163, (2004).

Picuri et al., "Universal Translators for Nucleic Acid Diagnosis", J. Am. Chem. Soc. 2009, 131, 9368-9377.

Podyminogin, et al., "Attachment of benzaldehyde-modified oligodeoxynucleotide probes to semicarbazide-coated glass", Nucleic Acids Research, vol. 29, No. 24, pp. 5090-5098, (2001).

Reese, "Oligo- and poly-nucleotides: 50 years of chemical synthesis", Organic & Biomolecular Chemistry, 3: 3851-3868, (2005).

Sager, et al., "Designing nucleotide sequences for computation: A survey of constraints", DNA11, LNCS 3892: 275-289, (2006).

Sahu et al., "Synthesis of Conformationally Preorganized and Cell Permeable Guanidine-Based-Peptide Nucleic Acids (GPNAs)", J. Org. Chem. 2009, 74, 1509-1516.

Santalucia, "A unified view of polymer, dumbbell, and oligonucleotide DNA nearest-neighbor thermodynamics", PNAS, vol. 95, pp. 1460-1465, (1998).

Seelig et al., "Enzyme-Free Nucleic Acid Logic Circuits", Science, vol. 314, Dec. 8, 2006, pp. 1585-1588.

Speicher, "Karyotyping human chromosomes by combinatorial multi-fluor FISH", Nature Genetics, 12: 368-375, (1996).

Summerton et al., "Review Article Morpholino Antisense Oligomers: Design, Preparation, and Properties", Antisense and Nucleic Acid Drug Development 7: 187-195 (1997).

Tajima et al., "Direct Oxidative Cyanation Based on the Concept of Site Isolation", J. Am. Chem. Soc. 2008, 130, 10496-10497.

Uhlmann, et al., "Synthesis and properties of PNA/DNA Chimeras", Angew. Chem. Int. Ed. Engl 35, No. 22, 2632-2635, (1996).

Veheijen, et al., "Transition metal derivatives of peptide nucleic acid (PNA) Oligomers—Synthesis, characterization, and DNA binding", Bioconjugate Chemistry, vol. 11, No. 6, pp. 741-743, (2000).

Voelcker et al., "Sequence-Addressable DNA Logic", Small 2008, 4, No. 4, pp. 427-431.

(56) References Cited

OTHER PUBLICATIONS

Voit, "Sequential One-Pot Reactions Using the Concept of Site Isolation", Angew. Chem. Int. Ed. 2006, 45, 4238-4240.

Yashin et al., "Networking Particles over Distance Using Oligonucleotide-Based Devices", J. Am. Chem. Soc., 2007, 129, 15581-15584.

Zhang et al., "Control of DNA Strand Displacement Kinetics Using Toehold Exchange", J. Am. Chem. Soc., 2009, 131, 17303-17314.

Zhang et al., "Engineering Entropy-Driven Reactions and Networks Catalyzed by DNA", Science, vol. 318, Nov. 16, 2007, 1121-1125.

Zhou et al., "Novel Binding and Efficient Cellular Uptake of Guanidine-Based Peptides Nucleic Acids (GPNA)", J. Am. Chem. Soc. 2003, 125, 6878-6879.

Chen, et al., "A Concise Method for the Preparation of Peptide and Arginine-Rich Peptide-Conjugated Antisense Oligonucleotide," Bioconjugate Chem, 2003, vol. 14, pp. 532-538.

International Preliminary Report on Patentability for PCT/US 2014/021148, mailed Sep. 8, 2015, 6 pages.

International Search Report for PCT/US 2014/021148, mailed Jul. 10, 2014, 2 pages.

Rozkiewicz, et al., "Transfer Printing of DNA by "Click" Chemistry," ChemBioChem, 2007, vol. 8, pp. 1997-2002.

\* cited by examiner

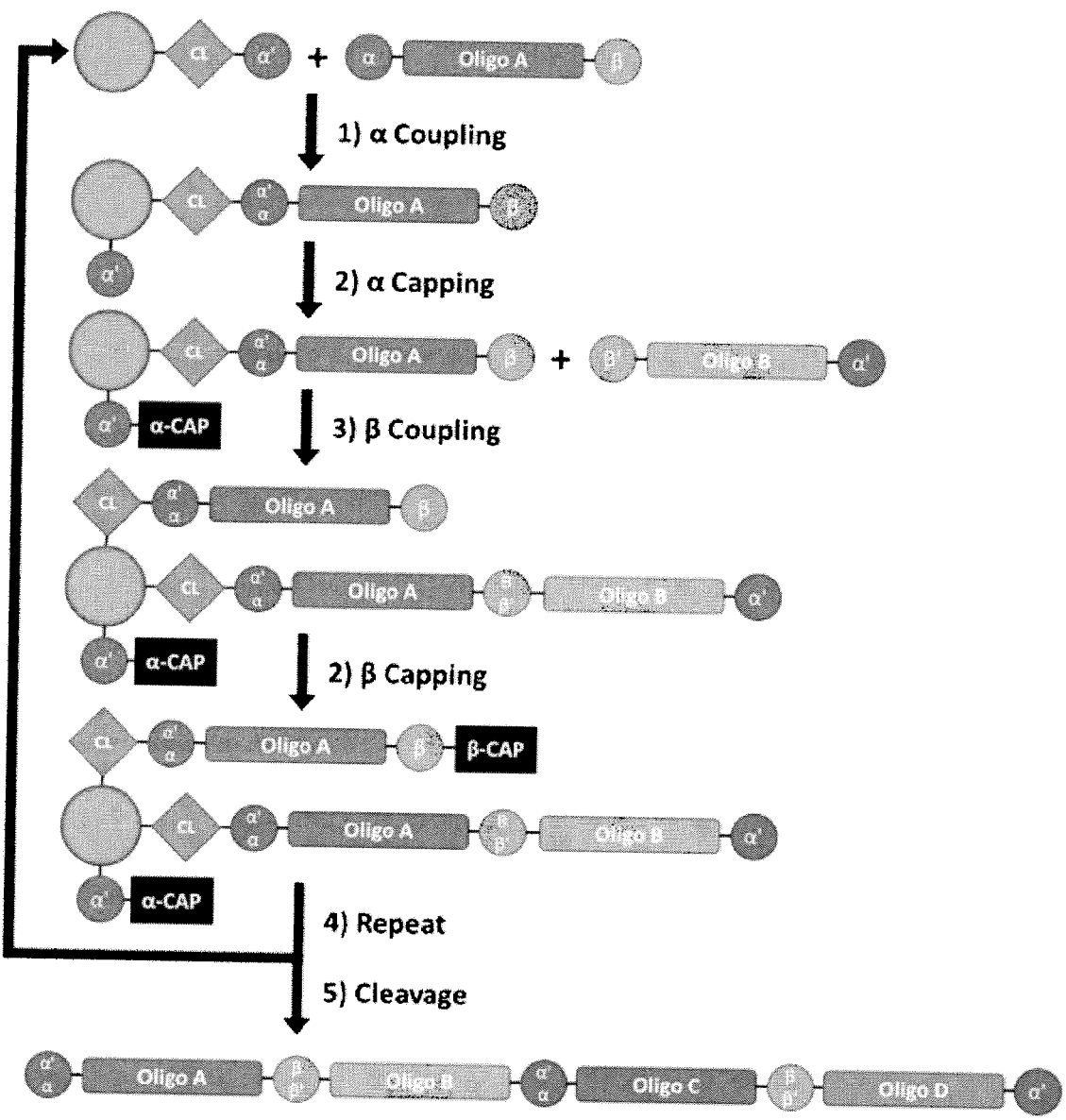
Figure 1. Asymmetric protocol schematic

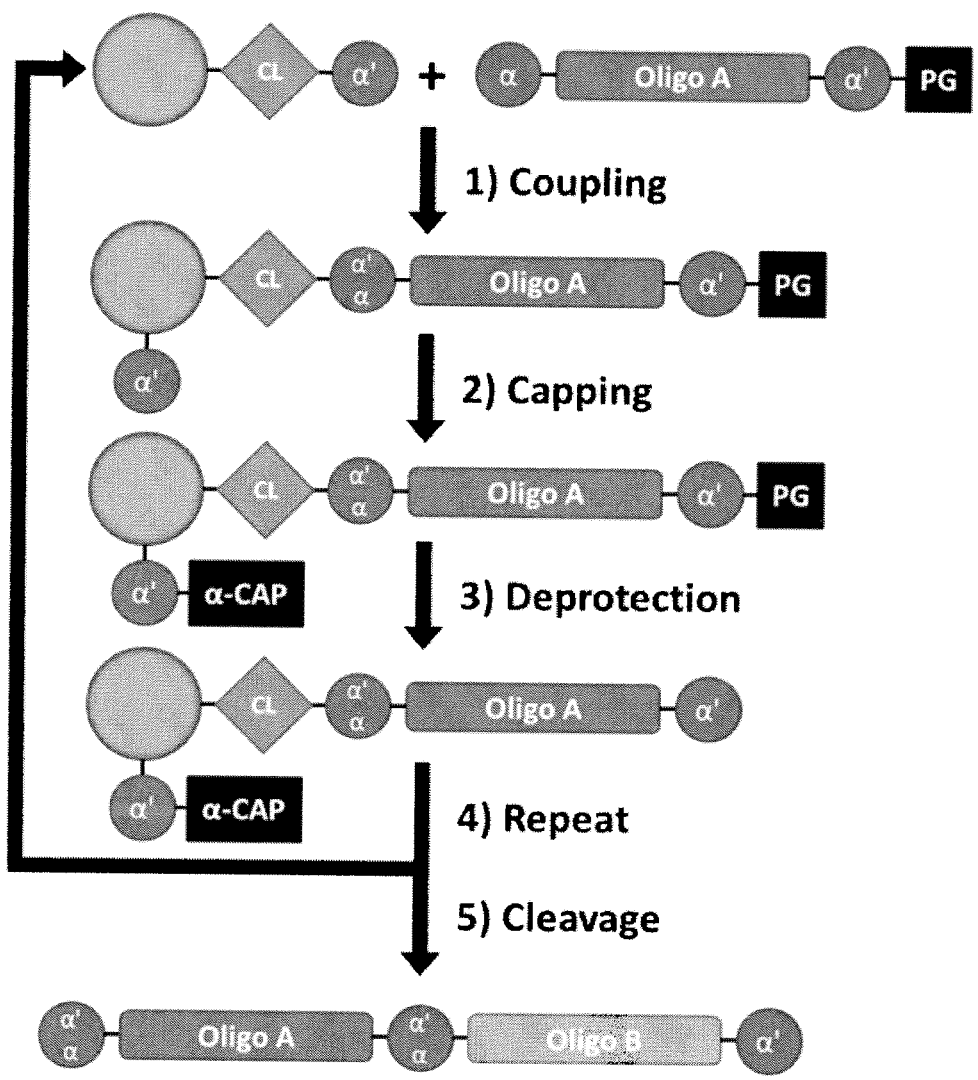
Figure 2. Symmetric protocol schematic

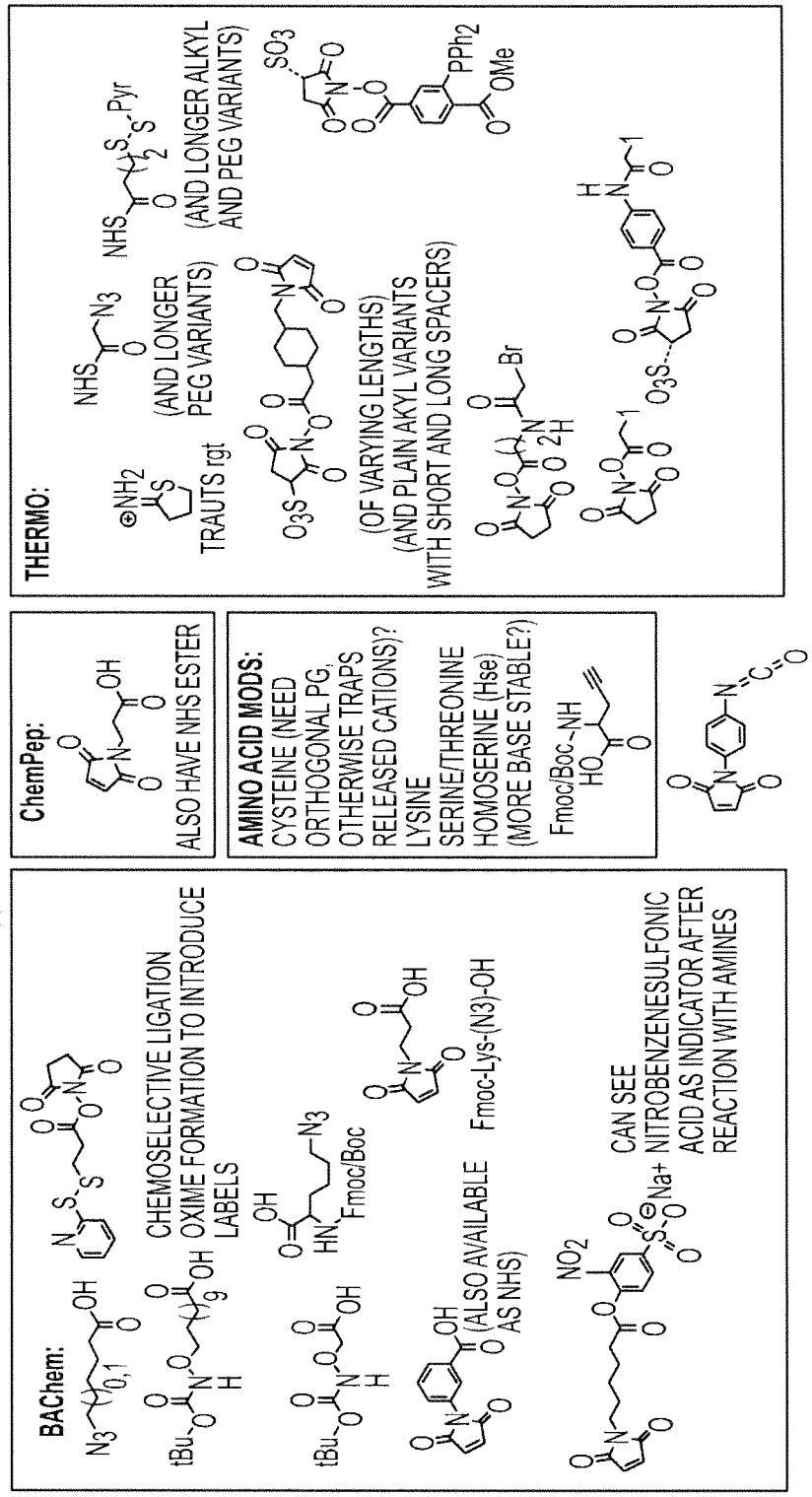
FIGURE 3A N-TERMINAL MODIFICATIONS OF PNA

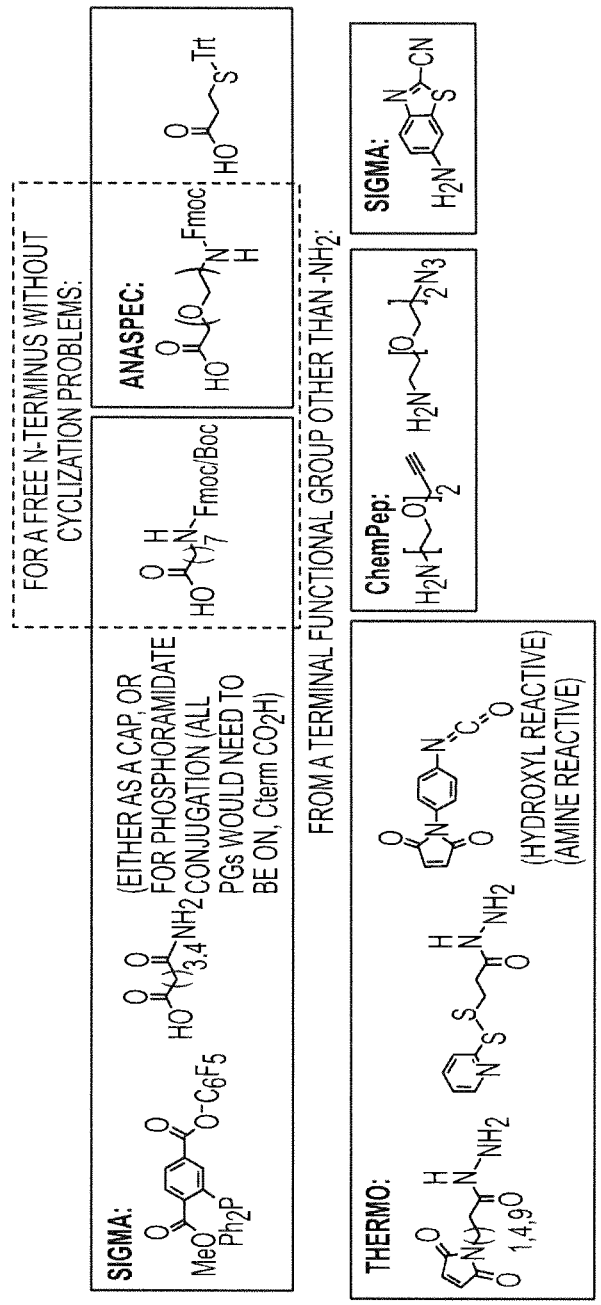
FIGURE 3B N-TERMINAL MODIFICATIONS OF PNA

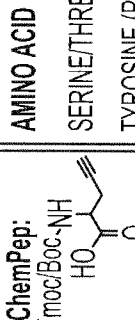
FIGURE 4 C-TERMINAL MODIFICATIONS OF PNA

PREPARATION OF OLIGO CONJUGATES

FIELD

The present technology relates generally to the preparation of oligo conjugates, which can be constituents of nano-scale information processing systems. In this context, the category of oligos encompasses polymers of 2'-deoxyribosenucleotide residues (DNA), ribonucleotide residues (RNA), or both DNA residues and RNA residues. The oligo category also includes polymers of peptide nucleic acids (PNAs) as well as heteropolymers that comprise both PNA monomers and RNA and/or DNA monomers.

BACKGROUND

Nucleic acids have been used to implement nano-scale information processing systems suitable for solving computational problems in a test tube or in a cell, as illustrated in U.S. patent application publications No. 20050112614, No. 20100069621 and No. 20110294687 and in U.S. Pat. No. 7,745,594. Such nano-scale systems typically must be compatible with a biological environment, particularly, if their potential for use in diagnostic assays or for treatment of diseases is to be realized.

A nano-scale information processing system suitable for such uses requires several nucleic acid segments that can serve as computation units that are capable of performing logical operations. Thus, there exists a need to develop synthetic strategies that will permit the synthesis of a diverse array of oligos, at high purity, as well as strategies for conjugating or annealing such oligos in an efficient, well-controlled manner.

SUMMARY

The methodology of the invention accommodates various conjugation components, discussed in detail below, to yield conjugated molecules that comprise a predetermined number of the components, as desired. The inventive methodology thus can be used to develop nano-scale information processing systems, as described above. In particular, the invention is also suitable for producing biological transistors, which can be part of integrated circuits capable of executing compound logic functions, e.g., in diagnostic or therapeutic contexts that entail targeting of neoplastic or virus-infected cells.

Accordingly, the invention provides a method for preparing a compound of the formula

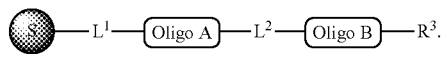

The inventive method comprises
(i) attaching a conjugation component of formula

wherein $R^2$ is $R^{2a}$ or $R^{2ap}$, to a solid support

to form a compound of formula

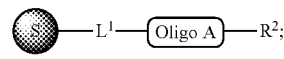

(ii) when $R^2$ is $R^{2ap}$, converting

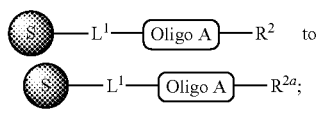

and
(iii) reacting

with a conjugation component of formula

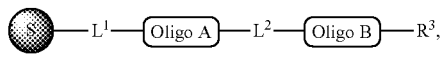

where $R^3$ can be a protected conjugation functionality $R^{3ap}$ or an unprotected conjugation functionality $R^{3a}$. When $R^3$ is $R^{3a}$ then (iv) the latter further reacts with an oligo. As noted above, the oligo can comprise (a) a sequence of 2'-deoxyribosenucleotide residues (DNA), (b) a sequence of ribonucleotide residues (RNA), or (c) a sequence containing both 2'-deoxyribosenucleotide residues and ribosenucleotide residues. Alternatively, the oligo can be comprised of peptide nucleic acid monomers (PNAs), linked by amide bonds, or it can be a heteropolymer that has both PNA monomers and RNA and/or DNA monomeric units. An oligo may optionally comprise a label.

The reaction (iv) forms

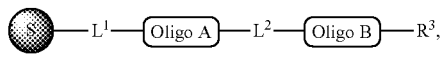

where

is a solid support material and

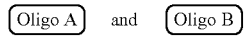

are independently selected from the category of oligos, defined above. In addition, - - - represents the point of connection to the part of the solid support-bound conjugated molecule that is closer to

, and ∿∿∿ represents the point of connection to the part of the solid support-bound conjugated molecule that is further away from

.

The inventive methodology thus described is qualified in that $R^2$ does not react with $R^{1a}$ or $R^{1b}$ and $R^3$ does not react with $R^{2a}$ or $R^{2b}$ as further described below. Furthermore, substituents $R^{1a}$ and $R^{1b}$ are complementary conjugation functionalities and $L^1$ is conjugate linker formed by reaction of $R^{1a}$ and $R^{1b}$. In keeping with this characterization of their respective chemical roles, selections of $R^{1a}$, $R^{1b}$ and $L^1$ can be grouped as follows:

(a) $R^{1a}$ is azido, $R^{1b}$ is —C≡C—$R^{23}$, and $L^1$ is

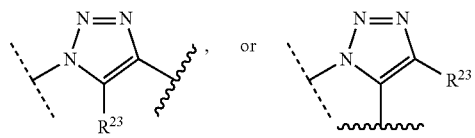

or
(b) $R^{1a}$ is —$NHR^{23}$, $R^{1b}$ is carboxy, and $L^1$ is —$NR^{23}C(=O)$—, or
(c) $R^{1a}$ is carboxy, $R^{1b}$ is —$NHR^{23}$, and $L^1$ is —$C(=O)NR^{23}$—, or
(d) $R^{1a}$ is —$NHR^{23}$, $R^{1b}$ is halo, and $L^1$ is —$NR^{23}$—, or
(e) $R^{1a}$ is —O—P(=O)(OH)(X), $R^{1b}$ is hydroxy, and $L^1$ is —O—P(=O)(OH)—O—, or
(f) $R^{1a}$ is —O—P(=O)(OH)(X), $R^{1b}$ is —$NHR^{23}$, and $L^1$ is —O—P(=O)(OH)—$NR^{23}$—, or
(g) $R^{1a}$ is —O—P(=O)(OH)(X), $R^{1b}$ is thio, and $L^1$ is —O—P(=O)(OH)—S—, or
(h) $R^{1a}$ is —X, $R^{1b}$ is thio, and $L^1$ is —S—, or
(i) $R^{1a}$ is

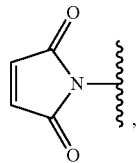, $R^{1b}$ is thio, and $L^1$ is

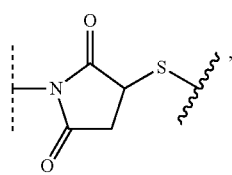, or
(j) $R^{1a}$ is —C≡C—$R^{23}$, $R^{1b}$ is azido, and $L^1$ is

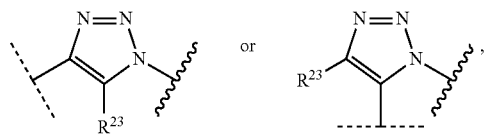

or
(k) $R^{1a}$ is —X, $R^{1b}$ is —$NHR^{23}$, and $L^1$ is —$NR^{23}$—, or
(l) $R^{1a}$ is hydroxy, $R^{1b}$ is —O—P(=O)(OH)(X), and $L^1$ is —O—P(=O)(OH)—O—, or
(m) $R^{1a}$ is —$NHR^{23}$, $R^{1b}$ is —O—P(=O)(OH)(X), and $L^1$ is —$NR^{23}$—P(=O)(OH)—O—, or
(n) $R^{1a}$ is thio, $R^{1b}$ is —O—P(=O)(OH)(X), and $L^1$ is —S—P(=O)(OH)—O—, or
(o) $R^{1a}$ is —O—P(=O)(OH)SH, $R^{1b}$ is —X, and $L^1$ is —O—P(=O)(OH)—S—, or
(p) $R^{1a}$ is —X, $R^{1b}$ is —O—P(=O)(OH)SH, and $L^1$ is —S—P(=O)(OH)—O—, or
(q) $R^{1a}$ is —$(CR^{25}R^{25})_sC(=O)OR^{23}$, $R^{1b}$ is —$NHR^{23}$, $L^1$ is —$(CR^{25}R^{25})C(=O)NR^{23}$—, or
(r) $R^{1a}$ is —$NHR^{23}$, $R^{1b}$ is —$(CR^{25}R^{25})_sC(=O)OR^{23}$, $L^1$ is —$NR^{23}C(=O)$—$(CR^{25}R^{25})_s$—, or
(s) $R^{1a}$ is thio, $R^{1b}$ is —X, and $L^1$ is —S—, or
(t) $R^{1a}$ is thio, $R^{1b}$ is

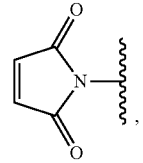 [SMILES: *N1C(=O)C=CC1=O]

and $L^1$ is

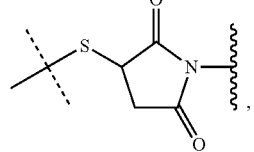, or
(u) $R^{1a}$ is —SH, $R^{1b}$ is —O—P(=O)(OH)(O—$(CH_2)_n$—SH) and $L^1$ is —S—S—$(CH_2)_n$—O—P(OH)(=O)—O—.

In the above characterization of $R^{1a}$ and $R^{1b}$ group X is selected from chlorine, bromine, fluorine, tosylate, mesylate, triflate, or dimethoxy triflate and n is 1, 2, 3, 4, 5, or 6.

Similarly, $R^{2a}$ and $R^{2b}$ are complementary conjugation functionalities and $L^2$ is conjugate linker formed by reacton of $R^{2a}$ and $R^{2b}$, and they likewise can be groups as above. Thus, (a') $R^{2ap}$ is halo, $R^{2a}$ is azido, $R^{2b}$ is —C≡C—$R^{23}$, and $L^2$ is

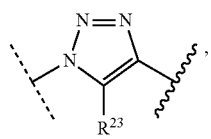

or
- (b') $R^{2ap}$ is —$NR^{23}Pr$, $R^{2a}$ is —$NHR^{23}$, $R^{2b}$ is carboxy, and $L^2$ is —$NR^{23}C(=O)$—, or
- (c') $R^{2ap}$ is carboxy ester, $R^{2a}$ is carboxy, $R^{2b}$ is —$NHR^{23}$, and $L^2$ is —$C(=O)NR^{23}$—, or
- (d') $R^{2ap}$ is —$NR^{23}Pr$, $R^{2a}$ is —$NHR^{23}$, $R^{2b}$ is halo, and $L^2$ is —$NR^{23}$—, or
- (e') $R^{2ap}$ is —OH, phosphate or phosphate ester, $R^{2}$ is —O—$P(=O)(OH)(X)$, $R^{2b}$ is hydroxy, and $L^2$ is —O—$P(=O)(OH)$—O—, or
- (f') $R^{2ap}$ is —OH, phosphate or phosphate ester, $R^{2a}$ is —O—$P(=O)(OH)(X)$, $R^{2b}$ is —$NHR^{23}$, and $L^2$ is —O—$P(=O)(OH)$—$NR^{23}$—, or
- (g') $R^{2ap}$ is —OH, phosphate or phosphate ester, $R^{2a}$ is —O—$P(=O)(OH)(X)$, $R^{2b}$ is thio, and $L^2$ is —O—$P(=O)(OH)$—S—, or
- (h') $R^{2a}$ is halo, $R^{2b}$ is thio, and $L^2$ is —S—, or
- (i') $R^{2a}$ is

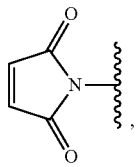

$R^{2b}$ is thio, and $L^2$ is

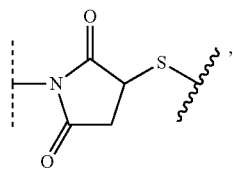

or
- (j') $R^{2a}$ is —C≡C—$R^{23}$, $R^{2b}$ is azido, and $L^2$ is

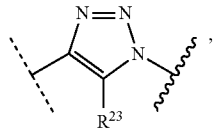

or
- (k') $R^{2a}$ is —X, $R^{2b}$ is —$NHR^{23}$, and $L^2$ is —$NR^{23}$—, or
- (l') $R^{2a}$ is hydroxy, $R^{2b}$ is —O—$P(=O)(OH)(X)$, and $L^2$ is —O—$P(=O)(OH)$—O—, or
- (m') $R^{2a}$ is —$NHR^{23}$, $R^{2b}$ is —O—$P(=O)(OH)(X)$, and $L^2$ is —$NR^{23}$—$P(=O)(OH)$—O—, or
- (n') $R^{2a}$ is thio, $R^{2b}$ is —O—$P(=O)(OH)(X)$, and $L^2$ is —S—$P(=O)(OH)$—O—, or
- (o') $R^{2ap}$ is —O—$P(=O)(OH)SR^{24}$, $R^{2a}$ is —O—$P(=O)(OH)SH$, $R^{2b}$ is —X, and $L^2$ is —O—$P(=O)(OH)$—S—, or
- (p') $R^{2a}$ is —X, $R^{2b}$ is —O—$P(=O)(OH)SH$, and $L^2$ is —S—$P(=O)(OH)$—O—, or
- (q') $R^{2a}$ is —$(CR^{25}R^{25})_sC(=O)OR^{23}$, $R^{2b}$ is —$NHR^{23}$, $L^2$ is —$(CR^{25}R^{25})_sC(=O)NR^{23}$—, or
- (r') $R^{2a}$ is —$NHR^{23}$, $R^{2b}$ is —$(CR^{25}R^{25})_sC(=O)OR^{23}$, $L^2$ is —$NR^{23}C(=O)$—$(CR^2R^2)_s$—, or
- (s') $R^{2a}$ is thio, $R^{2b}$ is —X, and $L^2$ is —S—, or

- (t') $R^{2a}$ is thio, $R^{2b}$ is

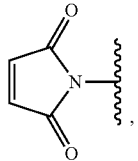

and $L^2$ is

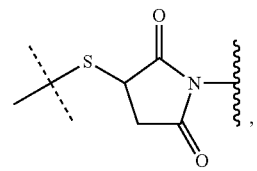

or
- (u') $R^{2a}$ is —SH, $R^{2b}$ is —O—$P(=O)(OH)(O$—$(CH_2)_n$—SH) and $L^2$ is —S—S—$(CH_2)_n$—O—$P(OH)(=O)$—O—.

In the above characterization of $R^{2a}$ and $R^{2b}$ group X is selected from chlorine, bromine, fluorine, tosylate, mesylate, triflate, or dimethoxy triflate.

In the foregoing description, $R^{23}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloalkynyl, substituted cycloalkynyl, heteroaryl, substituted heteroaryl, heterocyclic, and substituted heterocyclic. It also is the case that:

Pr is an amino protecting group;
$R^{24}$ is trityl or benzyl;
$R^{25}$ is hydrogen or $C_{1-6}$ alkyl;
s is an integer greater than 1;
$R^{3ap}$ is selected from the group consisting of halo, —$NR^{23}Pr$, —O—$P(=O)(OH)SR^{24}$, carboxy ester, phosphate and phosphate ester; and
$R^{3a}$ is selected from the group consisting of —X, azido, —C≡C—$R^{23}$, —$NHR^{23}$, carboxy, hydroxy, —C(=O)$OR^{23}$, —O—$P(=O)(OH)SH$ and —O—$P(=O)(OH)(X)$, and group X is selected from chlorine, bromine, fluorine, tosylate, mesylate, triflate, or dimethoxy triflate.

In one of its aspects, the inventive methodology embodies an asymmetric conjugation strategy, illustrated in FIG. 1. As shown, conjugation functionalities α, β are present at each end of a first oligo and conjugation functionalities α', β' at each end of a second oligo. FIG. 1 shows that (i) α reacts to form a new bond with α' and (ii) β reacts to form a new bond with β', but (iii) each of conjugation functionalities α or α' cannot react with β or β', respectively. Thus, two oligos, each having a different conjugation functionalities at their respective 5'-end and 3'-end, are linked to obtain a di-oligo product. In this way the asymmetric conjugation strategy of the invention permits the conjugation of components in a desired sequence and orientation, as exemplified by the product depicted in FIG. 1.

The inventive methodology also can proceed in accordance with a symmetric conjugation strategy, depicted in FIG. 2. Pursuant to this approach, every oligo has the same set of 5'- and 3'conjugation functionalities. Thus, oligo A and oligo B in FIG. 2 are shown to have the same set of α and α' functionalities at their respective termini.

Pursuant to the symmetric strategy of the invention, a polymer product containing oligo A and oligo B is obtained the by conjugating the unprotected α conjugation functionality of oligo A to solid support, the surface of which is functionalized with an α' group. The α' group at the other end of oligo A is protected, preventing unwanted conjugation between α and α' groups of separate oligo A molecules present in the reaction mixture. After oligo A is tethered to the solid support and the terminal α' group is deprotected, the tethered product is then allowed to come into contact with a molecule of oligo B, which has an unprotected α conjugation functionality at one end and a protected α' group at the other end.

By either the asymmetric approach or the symmetric approach, the present invention permits the "programmed" construction of a conjugated molecule of prescribed length and sequence. That is, production of a conjugated molecule pursuant to the invention can be designed beforehand and controlled in practice to determine, via the particular manner chosen by which the oligos are conjugated, the numbers and types of the oligos in the resultant conjugated molecule.

In a variation of inventive method, a compound of the formula

is produced by steps that comprise:
(i) attaching a compound of formula $$R^{1b} - \boxed{Oligo\ A} - R^{2a}$$

to a solid support

to form a compound of the formula

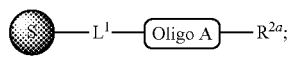

and
(iii) reacting

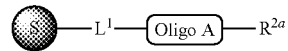

with a compound of the formula $$R^{2b} - \boxed{Oligo\ B} - R^{3a},$$

to form

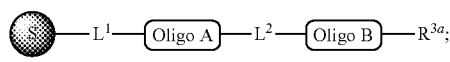

where:

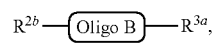

is a solid support material;

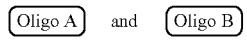

are independently selected from the group oligo;
$R^{1a}$ and $R^{1b}$ are complementary conjugation functionalities and $L^1$ is conjugate linker formed by reaction of $R^{1a}$ and $R^{1b}$, $R^{2a}$ and $R^{2b}$ are complementary conjugation functionalities and $L^2$ is conjugate linker formed by reacton of $R^{2a}$ and $R^{2b}$, $R^{1a}$, $R^{1b}$, $L^1$, $R^{2a}$, $R^{2b}$, $L^2$, and $R^{3a}$ are selected from

| $R^{1a}$, $R^{2a}$, or $R^{3a}$ | $R^{1b}$ or $R^{2b}$ | $L^1$ or $L^2$ |
|---|---|---|
| —C≡C—$R^{23}$ | azido | N=N triazole with $R^{23}$ |
| azido | —C≡C—$R^{23}$ | N=N triazole with $R^{23}$ |
| carboxy | —NHR$^{23}$ | —C(=O)NR$^{23}$— |
| —NHR$^{23}$ | carboxy | —NR$^{23}$C(=O)— |
| halo | —NHR$^{23}$ | —NR$^{23}$— |
| —NR$^{23}$Pr | halo | —NR$^{23}$— |
| hydroxy | —O—P(=O)(OH)(X) | —O—P(=O)(OH)—O— |
| —O—P(=O)(OH)(X) | hydroxy | —O—P(=O)(OH)—O— |
| —NHR$^{23}$ | —O—P(=O)(OH)(X) | —NR$^{23}$—P(=O)(OH)—O— |
| —O—P(=O)(OH)(X) | —NHR$^{23}$ | —O—P(=O)(OH)—NR$^{23}$— |

-continued

| $R^{1a}$, $R^{2a}$, or $R^{3a}$ | $R^{1b}$ or $R^{2b}$ | $L^1$ or $L^2$ |
|---|---|---|
| thio | —O—P(=O)(OH)(X) | —S—P(=O)(OH)—O— |
| —O—P(=O)(OH)(X) | thio | —O—P(=O)(OH)—S— |
| thio | —X | —S— |
| —X | thio | —S— |
| —O—P(=O)(OH)SH | —X | —O—P(=O)(OH)—S— |
| —X | —O—P(=O)(OH)SH | —S—P(=O)(OH)—O— |
| —(CR$^{25}$R$^{25}$)$_s$C(=O)OR$^{23}$ | —NHR$^{23}$ | —(CR$^{25}$R$^{25}$)$_s$C(=O)NR$^{23}$— |
| —NHR$^{23}$ | —(CR$^{25}$R$^{25}$)$_s$C(=O)OR$^{23}$ | —NR$^{23}$C(=O)—(CR$^{25}$R$^{25}$)$_s$— |
| thio | ![maleimide] | ![succinimide-S-tBu] |
| ![maleimide] | thio | ![succinimide-S] |
| —SH | —O—P(=O)(OH)(O—(CH$_2$)$_n$—SH) | —S—S—(CH$_2$)$_n$—O—P(OH)(=O)—O— | where the selection of $R^{1a}$, $R^{2a}$, or $R^{3a}$ is independent of each other provided that $L^1$ and $L^2$ are different, $R^{2a}$ does not react with $R^{1a}$ or $R^{1b}$, and $R^{3a}$ does not react with $R^{2a}$ or $R^{2b}$;

X is selected from chlorine, bromine, fluorine, tosylate, mesylate, triflate, or dimethoxy triflate;

$R^{23}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloalkynyl, substituted cycloalkynyl, heteroaryl, substituted heteroaryl, heterocyclic, and substituted heterocyclic;

$R^{25}$ is hydrogen or $C_{1-6}$ alkyl;

s is an integer of greater than 1;

- - - represents the point of connection to the part of the solid support-bound conjugated molecule that is closer to

, and ∿∿∿ represents the point of connection to the part of the solid support-bound conjugated molecule that is further away from

.

Pursuant to another variation of the inventive methodology, a compound is produced of the formula

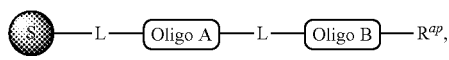

by steps comprising (i) attaching a compound of the formula

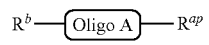

to a solid support

to form a compound of the formula

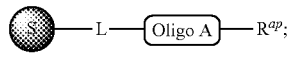;

(ii) converting

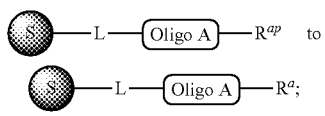

and (iii) reacting

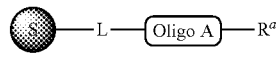

with a compound of the formula

, to form

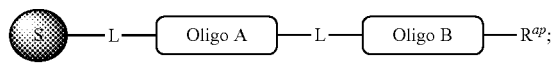

where:

is a solid support material;

are each independently selected from the group oligo;

$R^{ap}$ is protected conjugation functionality which when deprotected is converted to $R^a$, $R^a$ and $R^b$ are complementary conjugation functionalities and L is conjugate linker formed by reacton of $R^a$ and $R^b$. $R^{ap}$, $R^a$, $R^b$, and L are selected from (a) $R^{ap}$ is halo, $R^a$ is azido, $R^b$ is —C≡C—$R^{23}$, and L is

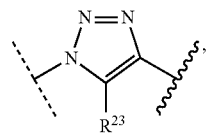

or (b) $R^{ap}$ is —$NR^{23}Pr$, $R^a$ is —$NHR^{23}$, $R^b$ is carboxy, and L is —$NR^{23}C(=O)$—, or (c) $R^{ap}$ is carboxy ester, $R^a$ is carboxy, $R^b$ is —$NHR^{23}$, and L is —$C(=O)NR^{23}$—, or (d) $R^{ap}$ is —$NR^{23}Pr$, $R^a$ is —$NHR^{23}$, $R^b$ is halo, and L is —$NR^{23}$—, or (e) $R^{ap}$ is —OH, phosphate or phosphate ester, $R^a$ is —O—P(=O)(OH)(X), $R^b$ is hydroxy, and L is —O—P(=O)(OH)—O—, or (f) $R^{ap}$ is —OH, phosphate or phosphate ester, $R^a$ is —O—P(=O)(OH)(X), $R^b$ is —$NHR^{23}$, and L is —O—P(=O)(OH)—$NR^{23}$—, or (g) $R^{ap}$ is —O—P(=O)(OH)$SR^{24}$, $R^a$ is —O—P(=O)(OH)SH, $R^b$ is halo, and L is —O—P(=O)(OH)—S—, or (h) $R^{ap}$ is —OH, phosphate or phosphate ester, $R^a$ is —O—P(=O)(OH)(X), $R^b$ is thio, and L is —O—P(=O)(OH)—S— or (i) $R^{ap}$ is —$SR^{24}$, $R^a$ is —SH, $R^b$ is —O—P(=O)(OH)SH and L is —O—P(=O)(OH)S—S—; where $R^{23}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloalkynyl, substituted cycloalkynyl, heteroaryl, substituted heteroaryl, heterocyclic, and substituted heterocyclic;

X is selected from chlorine, bromine, fluorine, tosylate, mesylate, triflate, or dimethoxy triflate;

Pr is an amino protecting group;

$R^{24}$ is trityl or benzyl; and

- - - represents the point of connection to the part of the solid support-bound conjugated molecule that is closer to

while ⁓⁓⁓ represents the point of connection to the part of the solid support-bound conjugated molecule that is further away from

In yet another variation, the method of the invention entails preparing a compound of the formula

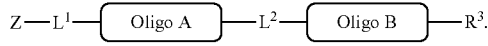

To this end the method comprises
cleaving the bond between

and $L^1$ of the compound of the formula

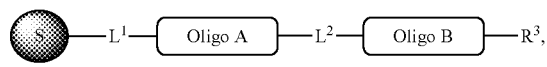

thereby obtaining

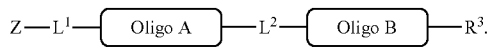

Z in the polymer product is selected from —OH, OH—($C_1$-$C_{10}$)alkylene-, —COOH, $NH_2C(O)$—, $NH_2NH$—C(O)—, COOH—($C_1$-$C_{10}$)alkylene-, $NH_2C(O)$—($C_1$-$C_{10}$)alkylene-, $NH_2NH$—C(O)—($C_1$-$C_{10}$)alkylene-, $CH_2$=CH—($C_1$-$C_{10}$)alkylene-, C≡C—($C_1$-$C_{10}$)alkylene- or HS—($C_1$-$C_{10}$)alkylene- and the alkylene can be optionally substituted by one or more groups selected from —OH, halogen, —NHR", —NHC(O)—($C_1$-$C_{10}$)alkylene-C≡CH, or —NHC(O)—($C_1$-$C_{10}$)alkylene-CH=$CH_2$. When the alkylene is substituted with an —NHR" group, variable R" is selected from ($C_1$-$C_{10}$)alkyl, ($C_3$-$C_{10}$)cycloalkyl, or ($C_3$-$C_{10}$)aryl Pursant to the present invention, conjugation functionality $R^3$ can be labeled by converting a compound of the formula

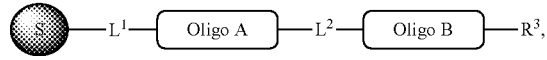

to a compound of the formula

In this context $R^3$ is brought into contact with an optically detectable group or a radiolabeled group, thereby to obtain a product that carries a detectable label. The labeled product can be cleaved from the solid support, in the manner described immediately above.

The invention also provides a method for producing a conjugated molecule that is bound to a solid support, as represented by the formula

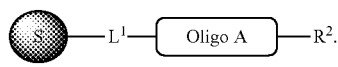

In the formula

is a solid support material,

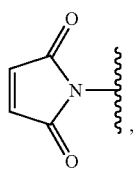 [SMILES: *N1C(=O)C=CC1=O]

is selected from the category of oligo defined above; and $R^2$ is either a protected conjugation functionality $R^{2ap}$, or an unprotected conjugation functionality $R^{2a}$. When $R^2$ is $R^{2ap}$ then $R^{2ap}$ is selected from the group consisting of halo, $NR^{23}Pr$, carboxy ester, phosphate, phosphate ester, and $-O-P(=O)(OH)SR^{24}$. Following removal of the protection group, $R^{2ap}$ is converted to $R^2$. $R^{2a}$ is a group selected from halo, azido, hydroxy, thio, $-NHR^{23}$, carboxy,

$-O-P(=O)(OH)(X)$, $-C\equiv C-R^{23}$, $-O-P(=O)(OH)SH$ and $-(CR^{25}R^{25})_sC(=O)OR^{23}$, and X is selected from chlorine, bromine, fluorine, tosylate, mesylate, triflate, or dimethoxy triflate. Furthermore, $L^1$ is selected from the group consisting of $-C(=O)NR^{23}-$, $-NR^{23}C(=O)-$, $-(CR^{25}R^{25})_sC(=O)NR^{23}-$, $-NR^{23}C(=O)-(CR^{25}R^{25})_s-$, $-NR^{23}-$, $-O-P(=O)(OH)-O-$, $-NR^{23}-P(=O)(OH)-O-$, $-O-P(=O)(OH)-NR^{23}-$, $-S-$, $-S-P(=O)(OH)-O-$, and $-O-P(=O)(OH)-S-$,

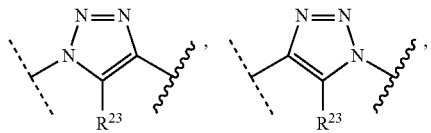

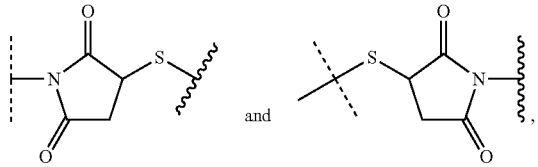

$R^{23}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloalkynyl, substituted cycloalkynyl, heteroaryl, substituted heteroaryl, heterocyclic, and substituted heterocyclic, $R^{24}$ is trityl or benzyl, $R^{25}$ is hydrogen or $C_{1-6}$ alkyl, s is an integer of greater than 1,

- - - represents the point of connection to the part of the solid support-bound conjugated molecule that is closer to

and ∿∿∿ represents the point of connection to the part of the solid support-bound conjugated molecule that is further away from

In yet another aspect, the invention provides a compound according formula:

where $R^2$ is a protected conjugation functionality $R^{2ap}$, or an unprotected conjugation functionality $R^{2a}$.

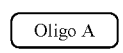

is selected from the oligo category defined above, and substituent $R^{1b}$ is selected from the group consisting of $-C\equiv C-R^{23}$, carboxy, $-NHR^{23}$, halo, hydroxy, thio, azido, $-O-P(=O)(OH)(X)$, $-O-P(=O)(OH)SH$, $-(CR^{25}R^{25})_sC(=O)OR^{23}$, and

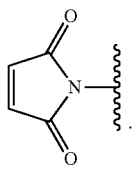 [SMILES: *N1C(=O)C=CC1=O]

Group X is selected from chlorine, bromine, fluorine, tosylate, mesylate, triflate, or dimethoxy triflate.

Furthermore, $R^{2ap}$ is selected from the group consisting of halo, $NR^{23}Pr$, carboxy ester, phosphate, phosphate ester, and —O—P(=O)(OH)$SR^{24}$, $R^{2a}$ is selected from the group consisting of halo, azido, hydroxy, thio, —$NHR^{23}$, carboxy, —$NHR^{23}$, —O—P(=O)(OH)(X),

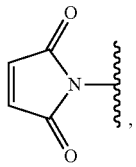 [SMILES: *N1C(=O)C=CC1=O]

—C≡C—$R^{23}$, —O—P(=O)(OH)SH and —$(CR^{25}R^{25})_sC(=O)OR^{23}$, $R^{23}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, $R^{24}$ is alkyl or benzyl, and ∿∿ represents the point of connection to Oligo A .

Group X is as defined above.

These and other aspects and embodiments of the invention are further described in the text that follows.

BRIEF DESCRIPTION OF THE DRAWINGS

The invention will be more fully understood by reference to the following drawings, which are for illustrative purposes only:

FIG. 1 illustrates an asymmetric conjugation strategy of the invention.

FIG. 2 illustrates a symmetric conjugation strategy of the invention.

FIGS. 3A and 3B Reagents for functionalizing the N-terminal of a PNA.

FIG. 4 Reagents for functionalizing the C-terminal of a PNA.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Definitions

Certain terms employed in this description have the following defined meanings. Terms that are not defined have their art-recognized meanings.

As used in the specification and claims, the singular form "a", "an" and "the" include plural references unless the context clearly dictates otherwise.

The term "comprising" is intended to mean that the devices and methods include the recited components or steps, but not excluding others. "Consisting essentially of" when used to define devices and methods, shall mean excluding other components or steps that would materially affect the basic and novel characteristics of the technology. "Consisting of" shall mean excluding any components or steps not specified in the claim. Embodiments defined by each of these transition terms are within the scope of this disclosure.

"Solid support" refers to a solid material on which a compound can be attached during solid phase synthesis. This class of materials is exemplified as polystyrene, such as styrene cross-linked with 1-2% divinylbenzene, polyacrylamide, PEG-polystyrene (PEG-PS), PEG-based supports, which are composed of a PEG-polypropylene glycol network or PEG with polyamide or polystyrene, controlled pore glass, cellulose fibers, and highly cross-linked polystyrene, gel-type polymers supported by rigid matrices.

The term "oligo" denotes a category, discussed above, that encompasses a polymer, having from 2 to about 150 covalently linked monomer units, that is characterized by (i) a sequence of 2'-deoxyribonucleotide residues (DNA), (ii) a sequence of ribonucleotide residues (RNA), or (iii) a sequence containing both 2'-deoxyribonucleotide residues and ribosenucleotide residues, which may be referred to as an oligonucleotide. The oligo category also encompasses polymers of peptide nucleic acid monomers (PNAs), in which the monomeric units are linked to each other by an amide bond. In the present context an oligo also can be a heteropolymer that has both PNA monomers and RNA and/or DNA monomeric units.

The monomeric units of an oligonucleotide can be linked through a phosphodiester bond, a phosphorothioate bond, a methylphosphonate bond, or an amide (—C(O)—NH—) bond, as a function of the chemical nature of monomers used to synthesize the oligo. In a given embodiment the oligo is functionalized through the conjugation of another group. The latter group also can be labeled with any manner of detectable group.

"Peptide" refers to a polymer amino acid monomers (whether or not naturally occurring) linked by peptide bonds (also known as amide bonds) formed when the carboxyl carbon atom of the carboxylic acid group bonded to the alpha-carbon of one amino acid (or amino acid residue) becomes covalently bound to the amino nitrogen atom of the amino group bonded to the alpha-carbon of an adjacent amino acid (or amino acid residue). Amino acids which have been incorporated into a peptide are termed amino acid residues. Every peptide has an N-terminus and C-terminus residue on the ends of the peptide (except for cyclic peptides). Peptides typically have fewer than 50 amino acid residues. "Protein" refers polymers of amino acid monomers linked by peptide bonds that have more amino acid residues than peptides.

"Peptide nucleic acid" or PNA refers to synthetic polymers comprising repeating N-(2-aminoethyl)-glycine units linked by amide bonds. The purine (adenine (A) guanine (G)) and pyrimidine (thymine (T) and cytosine (C)) bases are attached to the backbone through methylene carbonyl linkages. PNAs do not contain any pentose sugar moieties or phosphate groups. Examples of peptide nucleic acids are described in U.S. Pat. No. 5,539,082 and No. 6,395,474.

"Peptide nucleic acid derivative" refers to a peptide nucleic acid wherein the N-(2-aminoethyl)-glycine backbone or one or more bases are modified, or which comprises additional moieties, as a metal complex or a detectable moiety. Illustrative of peptide nucleic acid derivatives are those described in Hudson et al., *Pure Appl. Chem.* 76: 1591-98 (2004), Imoto, *Nucleic Acids Symp Ser* 52: 391-92 (2008), Ferrer et al., *Letters in Peptide Science* 7: 195-206 (2000), Krämer et al., *Metal Ions Life Sci.* 10: 319-40 (2012), Verheijen et al., *Bioconjugate Chem.* 11: 741-43 (2000), and Ganesh, *Current Organic Chem.* 4: 931-43 (2000).

"Conjugation functionality" refers to a functional group on a molecule that can react with a functional group on another molecule resulting in connection of the two molecules through the formation of one or more covalent bonds. Conjugation functionalities are designated as $\alpha, \alpha', \beta, \beta', R^{1a}, R^{1b}, R^{2a}, R^{2b}$, etc. and described herein. The two conjugation functionalities that react with each other are referred to as complementary conjugation functionalities. For example, in this specification $\alpha$ and $\alpha'$, $\beta$ and $\beta'$, $R^{1a}$ and $R^{1b}$, $R^{2a}$ and $R^{2b}$ are pairs of complementary conjugation functionalities.

"Conjugation component" refers to a molecule, such as an oligo, having at least one conjugation functionality.

"Conjugate linker" refers to a linker formed by reaction of a conjugation functionality of one conjugation component with a complementary conjugation functionality of another conjugation component. Conjugate linkers are designated as $L^2$ and $L^3$, etc., and are described herein.

"Conjugated molecule" refers to a molecule having two or more conjugation components that are linked via a conjugate linker described herein. A conjugated molecule may be a conjugation component if it comprises a conjugation functionality.

"Alkyl" refers to monovalent saturated aliphatic hydrocarbyl groups having from 1 to 10 carbon atoms and preferably 1 to 6 carbon atoms. "$C_{u-v}$ alkyl" refers to alkyl groups having from u to v carbon atoms, wherein u and v are integers. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡H).

"Substituted alkyl" and "substituted $C_{u-v}$ alkyl" encompass an alkyl group having from 1 to 5 and, in some embodiments, 1 to 3 or 1 to 2 substituents selected from the group consisting of alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, spirocycloalkyl, SO$_3$H, substituted sulfonyl, sulfonyloxy, thioacyl, thiocyanate, thiol, alkylthio, and substituted alkylthio, where such substituents are defined in this specification.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

Acylamino" refers to the groups —$NR^{15}C(O)$alkyl, —$NR^{15}C(O)$substituted alkyl, —$NR^{15}C(O)$cycloalkyl, —$NR^{15}C(O)$substituted cycloalkyl, —$NR^{15}C(O)$cycloalkenyl, —$NR^{15}C(O)$substituted cycloalkenyl, —$NR^{15}C(O)$alkenyl, —$NR^{15}C(O)$substituted alkenyl, —$NR^{15}C(O)$alkynyl, —$NR^{15}C(O)$substituted alkynyl, —$NR^{15}C(O)$aryl, —$NR^{15}C(O)$substituted aryl, —$NR^{15}C(O)$heteroaryl, —$NR^{15}C(O)$substituted heteroaryl, —$NR^{15}C(O)$heterocyclic, and —$NR^{15}C(O)$substituted heterocyclic wherein $R^{15}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are both alkyl, the substituted amino group is sometimes referred to herein as dialkylamino. When referring to a monosubstituted amino, it is meant that either R' or R" is hydrogen but not both. When referring to a disubstituted amino, it is meant that neither R' or R" are hydrogen.

"Aminocarbonyl" refers to the group —$C(O)NR^{10}R^{11}$ where $R^{10}$ and $R^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{10}$ and $R^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —$OC(O)NR^{10}R^{11}$ where $R^{10}$ and $R^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{10}$ and $R^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —$C(=NR^{12})NR^{10}R^{11}$ where $R^{10}$, $R^{11}$, and $R^{12}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{10}$ and $R^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" refers to —COOH or a salt thereof.

"Carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —$NR^{16}$—C(O)O-alkyl, —$NR^{16}$—C(O)O-substituted alkyl, —$NR^{16}$—C(O)O-alkenyl, —$NR^{16}$—C(O)O-substituted alkenyl, —$NR^{16}$—C(O)O-alkynyl, —$NR^{16}$—C(O)O-substituted alkynyl, —$NR^{16}$—C(O)O-aryl, —$NR^{16}$—C(O)O-substituted aryl, —$NR^{16}$—C(O)O-cycloalkyl, —$NR^{16}$—C(O)O-substituted cycloalkyl, —$NR^{16}$—C(O)O-cycloalkenyl, —$NR^{16}$—C(O)O-substituted cycloalkenyl, —$NR^{16}$—C(O)O-heteroaryl, —$NR^{16}$—C(O)O-substituted heteroaryl, —$NR^{16}$—C(O)O-heterocyclic, and —$NR^{16}$—C(O)O-substituted heterocyclic wherein $R^{16}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. One or more of the rings can be aryl, heteroaryl, or heterocyclic provided that the point of attachment is through the non-aromatic carbon. Examples of suitable cycloalkyl groups include, for instance, adamantyl, cyclopropyl, cyclobutyl, cyclopentyl, and cyclooctyl. Other examples of cycloalkyl groups include bicycle[2,2,2]octanyl, norbornyl, and spirobicyclo groups such as spiro[4.5]dec-8-yl:

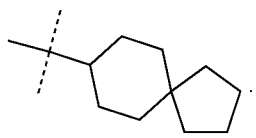

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Halo" or "halogen" refers to fluoro, chloro, bromo and iodo.

"Haloalkyl" refers to an alkyl group in which one or more hydrogen atoms are replaced by a halogen selected from chlorine, fluorine, bromine or iodine.

"Haloalkoxy" refers to —O-alkyl group in which one or more hydrogen atoms of the alkyl group are replaced by a halogen selected from chlorine, fluorine, bromine or iodine.

"Haloalkylthio" refers to —S-alkyl group in which one or more hydrogen atoms of the alkyl group are replaced by a halogen selected from chlorine, fluorine, bromine or iodine.

"Hydroxy" or "hydroxyl" refers to the group —OH.

"Heteroaryl" refers to a monocyclic aromatic group having 5 to 6 carbon atoms or a bicyclic ring having 8 to 10 carbon atoms containing 1 to 4 heteroatoms independently selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —$NO_2$.

"Oxo" refers to the atom (=O) or (—O).

"Spiro ring systems" refers to bicyclic ring systems that have a single ring carbon atom common to both rings.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" or "thio" refers to the group —SH.

"Thioether" refers to the group —S—.

"Alkylthio" refers to the group —S-alkyl wherein alkyl is as defined herein.

"Thiocarbonyl" refers to the divalent group —C(S)— which is equivalent to —C(=S)—.

"Thione" refers to the atom (=S).

"Substituted alkylthio" refers to the group —S-(substituted alkyl) wherein substituted alkyl is as defined herein.

"Azido" denotes the group —$N_3$.

"Amino protecting" groups are known in the field and illustrated by N-tert-butoxycarbonyl (t-Boc), 9-fluorenylmethoxycarbonyl (Fmoc), carboxybenzyl (Cbz), acetyl (Ac), benzoyl (Bz), p-methoxybenzyl carbonyl (Moz or MeOZ), benzyl (Bn), p-methoxybenzyl (PMB), 3,4-dimethoxybenzyl (DMPM), p-methoxyphenyl (PMP), etc.

"Phosphate" means —O—P(=O)(OH)$_2$.

"Phosphate ester" refers to —O—P(=O)(OH)(OR$^{23}$), wherein R$^{23}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic.

"Phosphoramidate" refers to the dianionic form of phosphoramidic acid [(OH)$_2$P(O)NH$_2$].

"Phosphonates" are organic compounds containing R$^{23}$—PO(OH)$_2$ or R$^{23}$—PO(OR)$_2$ groups where R is alkyl or aryl and R$^{23}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic.

"Phosphorothioate" refers to

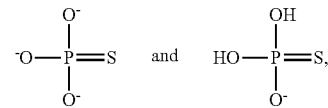

as well as to tautomers of these species, where "tautomer" denotes alternate forms of a compound that differ in the position of a proton.

General Conjugation Methodology

In one aspect, provided herewith is a method of preparing a solid support-bound conjugated molecule of the formula

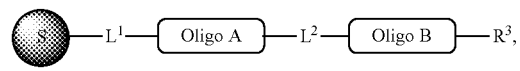

wherein the method comprises (i) attaching a conjugation component of the formula

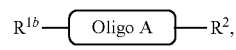

wherein R$^2$ is R$^{2a}$ or R$^{2ap}$, to a solid support

to form a compound of the formula

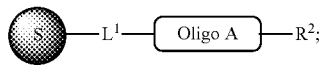

(ii) when $R^2$ is $R^{2ap}$, converting

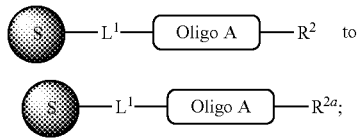

and
(iii) reacting

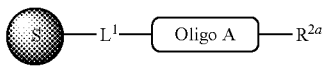

with a conjugation component of the formula

wherein $R^3$ is $R^{3a}$ or $R^{3ap}$, or $R^3$ is selected from —OH, a detectable label, or another oligo;
to form

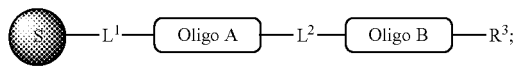

wherein:

is a solid support material;

Oligo A and Oligo B are each independently selected from the group oligo;

$R^{1a}$ and $R^{1b}$ are complementary conjugation functionalities, $L^1$ is conjugate linker, and $R^{1a}$, $R^{1b}$, and $L^1$ are:
(a) $R^a$ is azido, $R^{1b}$ is —C≡C—$R^3$, and $L^1$ is

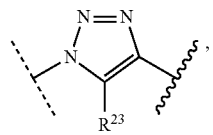

or
(b) $R^{1a}$ is —$NHR^{23}$, $R^{1b}$ is carboxy, and $L^1$ is —$NR^{23}$C(=O)—, or
(c) $R^{1a}$ is carboxy, $R^{1b}$ is —$NHR^{23}$, and $L^1$ is —C(=O)$NR^{23}$—, or
(d) $R^{1a}$ is —$NHR^{23}$, $R^{1b}$ is halo, and $L^1$ is —$NR^{23}$—, or
(e) $R^{1a}$ is —O—P(=O)(OH)(X), $R^{1b}$ is hydroxy, and $L^1$ is —O—P(=O)(OH)—O—, or
(f) $R^{1a}$ is —O—P(=O)(OH)(X), $R^{1b}$ is —$NHR^{23}$, and $L^1$ is —O—P(=O)(OH)—$NR^{23}$—, or
(g) $R^{1a}$ is —O—P(=O)(OH)(X), $R^{1b}$ is thio, and $L^1$ is —O—P(=O)(OH)—S—, or
(h) $R^{1a}$ is —X, $R^{1b}$ is thio, and $L^1$ is —S—, or
(i) $R^{1a}$ is

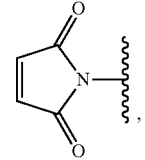 [SMILES: *N1C(=O)C=CC1=O]

$R^{1b}$ is thio, and $L^1$ is

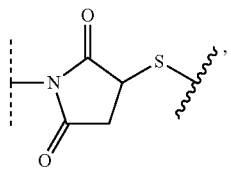

or
(j) $R^{1a}$ is —C≡C—$R^{23}$, $R^{1b}$ is azido, and $L^1$ is

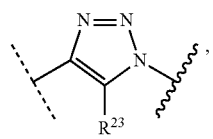

or
(k) $R^{1a}$ is halo, $R^{1b}$ is —$NHR^{23}$, and $L^1$ is —$NR^{23}$—, or
(l) $R^{1a}$ is hydroxy, $R^{1b}$ is —O—P(=O)(OH)(X), and $L^1$ is —O—P(=O)(OH)—O—, or
(m) $R^{1a}$ is —$NHR^{23}$, $R^{1b}$ is —O—P(=O)(OH)(X), and $L^1$ is —$NR^{23}$—P(=O)(OH)—O—, or
(n) $R^{1a}$ is thio, $R^{1b}$ is —O—P(=O)(OH)(X), and $L^1$ is —S—P(=O)(OH)—O—, or
(o) $R^{1a}$ is —O—P(=O)(OH)SH, $R^{1b}$ is —X, and $L^1$ is —O—P(=O)(OH)—S—, or
(p) $R^{1a}$ is —X, $R^{1b}$ is —O—P(=O)(OH)SH, and $L^1$ is —S—P(=O)(OH)—O—, or
(q) $R^{1a}$ is —$(CR^{25}R^{25})_sC(=O)OR^{23}$, $R^{1b}$ is —$NHR^{23}$, $L^1$ is —$(CRR^2R^2)_sC(=O)NR^{23}$—, or (r) $R^{1a}$ is —NHR$^{23}$, $R^{1b}$ is —(CR$^{25}$R$^{25}$)$_s$C(=O)OR$^{23}$, $L^1$ is —NR$^{23}$C(=O)—(CR$^{25}$R$^{25}$)—, or (s) $R^{1a}$ is thio, $R^{1b}$ is —X, and $L^1$ is —S—, or (t) $R^{1a}$ is thio, $R^{1b}$ is

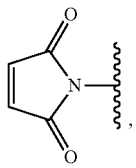 [SMILES: *N1C(=O)C=CC1=O]

and $L^1$ is

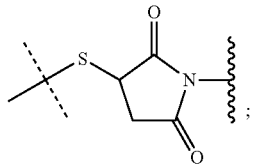

(u) $R^{1a}$ is —SH, $R^{1b}$ is —O—P(=O)(OH)(—O—(CH$_2$)$_n$—SH), and $L^1$ is —S—S—(CH$_2$)$_n$—O—P(OH)(=O)—O—.

In the above characterization of $R^{1a}$ and $R^{1b}$ group X is selected from chlorine, bromine, fluorine, tosylate, mesylate, triflate, or dimethoxy triflate where n is 1, 2, 3, 4, 5, or 6.

Similarly, $R^{2a}$ and $R^{2b}$ are complementary conjugation functionalities, $L^2$ is conjugate linker, and $R^{2ap}$, $R^{2a}$, $R^{2b}$, and $L^2$ are:

(a') $R^{2ap}$ is halo, $R^{2a}$ is azido, $R^{2b}$ is —C≡C—R$^{23}$, and $L^2$ is

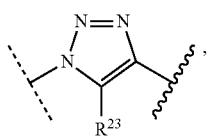

or (b') $R^{2ap}$ is —NR$^{23}$Pr, $R^{2a}$ is —NHR$^{23}$, $R^{2b}$ is carboxy, and $L^2$ is —NR$^{23}$C(=O)—, or (c') $R^{2ap}$ is carboxy ester, $R^{2a}$ is carboxy, $R^{2b}$ is —NHR$^3$, and $L^2$ is —C(=O)NR$^{23}$—, or (d') $R^{2ap}$ is —NR$^{23}$Pr, $R^{2a}$ is —NHR$^{23}$, $R^{2b}$ is halo, and $L^2$ is —NR$^2$—, or (e') $R^{2ap}$ is —OH, phosphate or phosphate ester, $R^{2a}$ is —O—P(=O)(OH)(X), $R^{2b}$ is hydroxy, and $L^2$ is —O—P(=O)(OH)—O—, or (f') $R^{2ap}$ is —OH, phosphate or phosphate ester, $R^{2a}$ is —O—P(=O)(OH)(X), $R^{2b}$ is —NHR$^{23}$, and $L^2$ is —O—P(=O)(OH)—NR$^{23}$—, or (g') $R^{2ap}$ is —OH, phosphate or phosphate ester, $R^{2a}$ is —O—P(=O)(OH)(X), $R^{2b}$ is thio, and $L^2$ is —O—P(=O)(OH)—S—, or (h') $R^{2a}$ is —X, $R^{2b}$ is thiO, and $L^2$ is —S—, or (i') $R^{2a}$ is

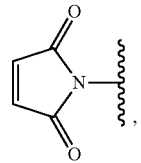 [SMILES: *N1C(=O)C=CC1=O]

$R^{2b}$ is thio, and $L^2$ is

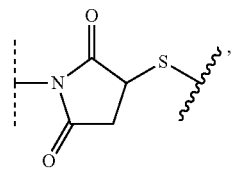

or (j') $R^{2a}$ is —C≡C—R$^{23}$, $R^{2b}$ is azido, and $L^2$ is

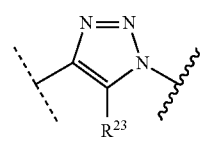

or (k') $R^{2a}$ is —X, $R^{2b}$ is —NHR$^{23}$, and $L^2$ is —NR$^{23}$—, or (l') $R^{2a}$ is hydroxy, $R^{2b}$ is —O—P(=O)(OH)(X), and $L^2$ is —O—P(=O)(OH)—O—, or (m') $R^{2a}$ is —NHR$^{23}$, $R^{2b}$ is —O—P(=O)(OH)(X), and $L^2$ is —NR$^{23}$—P(=O)(OH)—O—, or (n') $R^{2a}$ is thio, $R^{2b}$ is —O—P(=O)(OH)(X), and $L^2$ is —S—P(=O)(OH)—O—, or (o') $R^{2ap}$ is —O—P(=O)(OH)SR$^{24}$, $R^{2a}$ is —O—P(=O)(OH)SH, $R^{2b}$ is halo, and $L^2$ is —O—P(=O)(OH)—S—, or (p') $R^{2a}$ is —X, $R^{2b}$ is —O—P(=O)OH)SH, and $L^2$ is —S—P(=O)(OH)—O—, or (q') $R^{2a}$ is —(CR$^{25}$R$^{25}$)$_s$C(=O)OR$^{23}$, $R^{2b}$ is —NHR$^{23}$, $L^2$ is —(CR$^{25}$R$^{25}$)$_s$C(=O)NR$^{23}$—, or (r') $R^{2a}$ is —NHR$^{23}$, $R^{2b}$ is —(CR$^{25}$R$^{25}$)$_s$C(=O)OR$^{23}$, $L^2$ is —NR$^{23}$C(=O)—(CR$^2$SRR$^2$)$_s$—, or (s') $R^{2a}$ is thio, $R^{2b}$ is —X, and $L^2$ is —S—, or (t') $R^{2a}$ is thio, $R^{2b}$ is

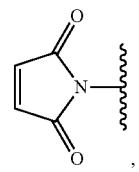 [SMILES: *N1C(=O)C=CC1=O]

and L² is

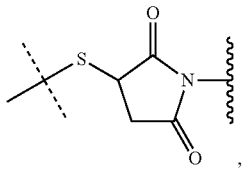

or
(u') R²ᵃ is —SH, R²ᵇ is —O—P(=O)(OH)(—O—(CH₂)ₙ—SH), and L² is —S—S—(CH₂)ₙ—O—P(OH)(=O)—O—.

In the above characterization of R¹ᵃ and R¹ᵇ group X is selected from chlorine, bromine, fluorine, tosylate, mesylate, triflate, or dimethoxy triflate Substituent R²³ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloalkynyl, substituted cycloalkynyl, heteroaryl, substituted heteroaryl, heterocyclic, and substituted heterocyclic, Pr is an amino protecting group, R²⁴ can be trityl or benzyl, substituent R²⁵ is hydrogen or $C_{1-6}$ alkyl and s is an integer greater than 1, for example, 2, 3, 4, 5, 6, 7, 8, 9, 10, 11, 12, 13, 14, 15, 16, 17, 18, 19, or 20.

For polymeric compounds synthesized using the inventive methodology, substituent $R^{3ap}$ is a protected conjugation functionality selected from the group consisting of halo, —NR²³Pr, —O—P(=O)(OH)SR²⁴, carboxy ester, phosphate and phosphate ester; and $R^{3a}$ is a conjugation functionality selected from the group consisting of azido, —C≡C—R²³, —NHR²³, carboxy, halo, hydroxy, —(CR¹²R²⁵)ₛC(=O)OR²³, —O—P(=O)(OH)SH and —O—P(=O)(OH)(X), where X is as defined above. In accordance with the inventive methodology, R² is not permitted to react with R¹ᵃ or R¹ᵇ, nor is R³ permitted to react with R²ᵃ or R²ᵇ. As discussed above, the symbol - - - represents the point of connection to the part of the solid support-bound conjugated molecule that is closer to

, and ∿∿∿ represents the point of connection to the part of the solid support-bound conjugated molecule that is further away from

.

In accordance with another aspect of the invention, the method is provided for preparing a solid support-bound conjugated molecule of the formula:

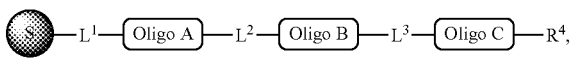

where the method comprises the following steps. When R³ is a protected conjugation functionality, such as the group $R^{3ap}$, deprotecting $R^{3ap}$ to convert

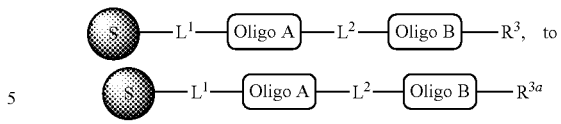

in a deprotection step. The deprotection step is followed by a conjugation step in which the solid support-bound conjugated molecule according to formula

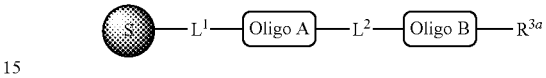

having a reactive conjugation functionality $R^{3a}$ is contacted with a conjugation component according to formula

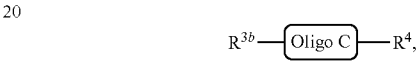

to form a solid support-bound conjugated molecule as illustrated below:

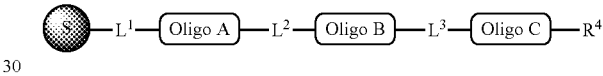

Substituent R⁴ in the obtained product is a group selected from halo, —NR²³Pr, —OH, —O—P(=O)(OH)SR²⁴, carboxy ester, phosphate, phosphate ester, azido, —C≡C—R²³, —NHR²³, carboxy, hydroxy, —(CR²⁵R²⁵)ₛC(=O)OR²³, —O—P(=O)(OH)SH, or —O—P(=O)(OH)(X). R⁴ can also be a detectable label or another oligo selected from DNA, RNA, a polymer containing both DNA and RNA residues, or a polymer composed entirely of PNA monomers. In any event, R⁴ does not react with $R^{3a}$ or $R^{3b}$.

The bond L¹ that binds the desired product to the solid support can be cleaved via a suitable cleavage method to give a conjugated molecule of the formula:

The method used to cleave the oligo product from the resin support will depend on the type of resin used to synthesize the oligo product, the chemical structure of L¹, the chemical identity of the other linkers (e.g., L², L³) in the product, as well as the stability of monomer groups in Oligos A, B and C to chemical reagents used to cleave the conjugated molecule from the solid support. The choice for using a particular resin will depend on protocols used for coupling the first monomer, the cleavage conditions to be used to obtain final product in high yield and the desired functionality, that is, the chemical nature of terminal group "Z" in the cleaved final product. Illustrative cleavage protocols are further described below. Several types of resin supports are commercially available. Exemplary of such supports without limitation are the controlled pore glass, PAM resin, benzhydrylamine resin (BHA), Wang resin, oxime resin (Kaiser), HMBA resin, Rink amide resin and PAL resin. Depending on the resin used, Z in the cleaved product can be any one of the following groups —OH, OH—($C_1$-$C_{10}$)alkylene-, —COOH, NH₂C(O)—, NH$_2$NH—C(O)—, COOH—(C$_1$-C$_{10}$)alkylene-, NH$_2$C(O)—(C$_1$-C$_{10}$)alkylene-, NH$_2$NH—C(O)—(C$_1$-C$_{10}$)alkylene-, CH$_2$=CH—(C$_1$-C$_{10}$)alkylene-, C≡C—(C$_1$-C$_{10}$)alkylene- or HS—(C$_1$-C$_{10}$)alkylene- and the alkylene can be optionally substituted by one or more groups selected from —OH, halogen, —NHR", —NHC(O)—(C$_1$-C$_{10}$)alkylene-C≡CH, or —NHC(O)—(C$_1$-C$_{10}$)alkylene-CH=CH$_2$ with R" defined as above. Illustrative of reagents used to cleave the oligo product from the solid support include UV light, acids such as trifluoromethane sulfonic acid, trifluoroacetic acid, hydrogen bromide, acetic acid. Nucleophilic reagents such as sodium hydroxide, hydrazine, alcohols primary amines and hydrides can be used to cleave the oligo product off HMBA and oxime resins. If the oligo is conjugated to solid support "S" through a disulfide linkage, cleavage of the oligo product from the solid support can be facilitated using a reducing agents. Illustrative of reagents suitable for cleaving a disulfide bond without limitation are β-mercaptoethanol dithiothreitol (DTT), tris-(2-carboxyethyl)phosphine (TCEP), or hydride reagents such as sodium borohydride and soudin cyanoborohydride. Depending on the cleaving reagent used oligo products having a terminal amide group, carboxylic acid group, alcohol group, aldehyde group or hydrazide group are obtained.

In some embodiments, the method further comprises repeating deprotection and conjugation steps described above "n" times to form a solid support-bound conjugated molecule of the formula:

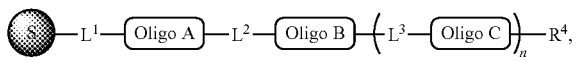

wherein n is an integer equal to or greater than 1, for example, an integer of between 1 and 50, or 1 and 25, or 1 and 20, or 1 and 10, and each

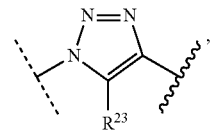

is independently selected from the above-discussed oligo category.

In the above method, the intermediate product after each conjugation step has a terminal group R$^4$. When R$^4$ is a conjugation functionality selected from the group consisting of azido, —C≡C—R$^{23}$, —NHR$^{23}$, carboxy, halo, hydroxy, —(CR$^{25}$R$^{25}$)$_s$C(=O)OR$^{23}$, —O—P(=O)(OH)SH and —O—P(=O)(OH)Br, R$^4$ is R$^{3a}$ and the deprotection step of converting R$^4$ to R$^{3a}$ may be omitted. When the R$^4$ is a group selected from halo, —NR$^{23}$Pr, —O—P(=O)(OH)SR$^{24}$, carboxy ester, phosphate or phosphate ester, the terminal protected conjugation functionality R$^4$ is first deprotected to obtain an intermediate that has the reactive conjugation functionality R$^{3a}$ described above. This intermediate then can be contacted with the next conjugation component

so as to permit a reaction between complementary conjugation functionalities R$^{3a}$ and R$^{3b}$, so as to covalently bond another

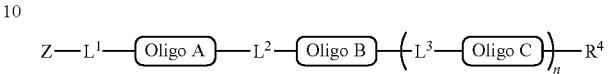

to the solid support-bound conjugated molecule.

After completion of the reaction sequence, the bond L$^1$ is cleaved under suitable cleavage conditions to give a conjugated molecule of the formula:

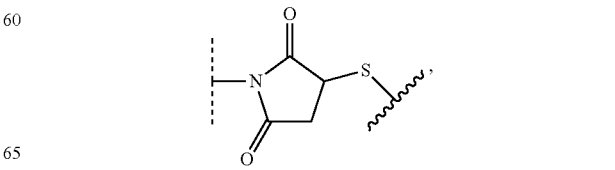

with Z being a group is as defined above.

For conjugated molecules that comport with the above formula, each set of R$^{3ap}$, R$^{3a}$, R$^{3b}$, and L$^3$ is independently selected from (a") R$^{3ap}$ is halo, R$^3$ is azido, R$^{3b}$ is —C≡C—R$^{23}$, and L$^3$ is

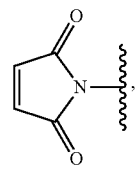 [SMILES: *N1C(=O)C=CC1=O ; ","]

or
(b") R$^{3ap}$ is —NR$^{23}$Pr, R$^{3a}$ is —NHR$^{23}$, R$^{3b}$ is carboxy, and L$^3$ is —NR$^{23}$C(=O)—, or
(c") R$^{3ap}$ is carboxy ester, R$^{3b}$ is carboxy, R$^{3b}$ is —NHR$^{23}$, and L$^3$ is —C(=O)NR$^{23}$—, or
(d") R$^{3ap}$ is —NR$^{23}$Pr, R$^{3a}$ is —NHR$^{23}$, R$^{3b}$ is halo, and L$^3$ is —NR$^{23}$—, or
(e") R$^{3ap}$ is —OH, phosphate or phosphate ester, R$^{3a}$ is —O—P(=O)(OH)(X), R$^{3b}$ is hydroxy, and L$^3$ is —O—P(=O)(OH)—O—, or
(f") R$^{3ap}$ is —OH, phosphate or phosphate ester. R$^{3a}$ is —O—P(=O)(OH)(X), R$^{3b}$ is —NHR$^{23}$, and L$^1$ is —O—P(=O)(OH)—NR$^{23}$—, or
(g") R$^{3ap}$ is —OH, phosphate or phosphate ester, R$^{3a}$ is —O—P(=O)(OH)(X), R$^{3b}$ is thio, and L$^1$ is —O—P(=O)(OH)—S—, or
(h") R$^{3a}$ is —X, R$^{3b}$ is thio, and L$^3$ is —S—, or
(i") R$^{3a}$ is

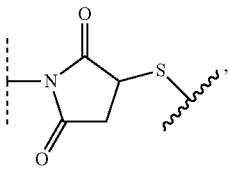

R$^{3b}$ is thio, and L$^3$ is

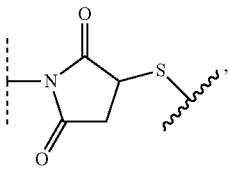

or (j") $R^{3a}$ is —C≡C—$R^{23}$, $R^{3b}$ is azido, and $L^3$ is

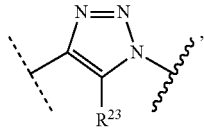

or (k") $R^{3a}$ is halo, $R^{3b}$ is —$NHR^{23}$, and $L^3$ is —$NR^{23}$—, or
(l") $R^{3a}$ is hydroxy, $R^{2b}$ is —O—P(=O)(OH)(X), and $L^3$ is —O—P(=O)(OH)—O—, or
(m") $R^{3a}$ is —$NHR^{23}$, $R^{3b}$ is —O—P(=O)(OH)(X), and $L^3$ is —$NR^{23}$—P(=O)(OH)—O—, or
(n") $R^{3a}$ is thio, $R^{3b}$ is —O—P(=O)(OH)(X), and $L^3$ is —S—P(=O)(OH)—O—, or
(o") $R^{3ap}$ is —O—P(=O)(OH)$SR^{24}$, $R^{3a}$ is —O—P(=O)(OH)SH, $R^{3b}$ is —X, and $L^3$ is —O—P(=O)(OH)—S—, or
(p") $R^{3a}$ is —X, $R^{3b}$ is —O—P(=O)(OH)SH, and $L^3$ is —S—P(=O)(OH)—O—, or
(q") $R^{3a}$ is —$(CR^{25}R^{25})_sC(=O)OR^{23}$, $R^{3b}$ is —$NHR^{23}$, $L^3$ is —$(CR^{25}R^{25})_sC(=O)NR^{23}$—, or
(r") $R^{3a}$ is —$NHR^{23}$, $R^{3b}$ is —$(CR^2SR^{25})C(=O)OR^{23}$, $L^3$ is —$NR^{23}C(=O)$—$(CR^{25}R^{25})_s$—, or (s") $R^{3a}$ is thio, $R^{3b}$ is —X, and $L^3$ is —S—, or
(t") $R^{3a}$ is thio, $R^{3b}$ is

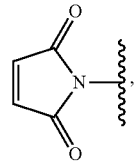 [SMILES: *N1C(=O)C=CC1=O ; ","]

and $L^3$ is or (u") $R^{3a}$ is —SH, $R^{3b}$ is —O—P(=O)(OH)(O—$(CH_2)_n$—SH) and $L^3$ is —S—S—$(CH_2)_n$—O—P(OH)(=O)—O—.

An embodiment of this general process is illustrated in Scheme 1.

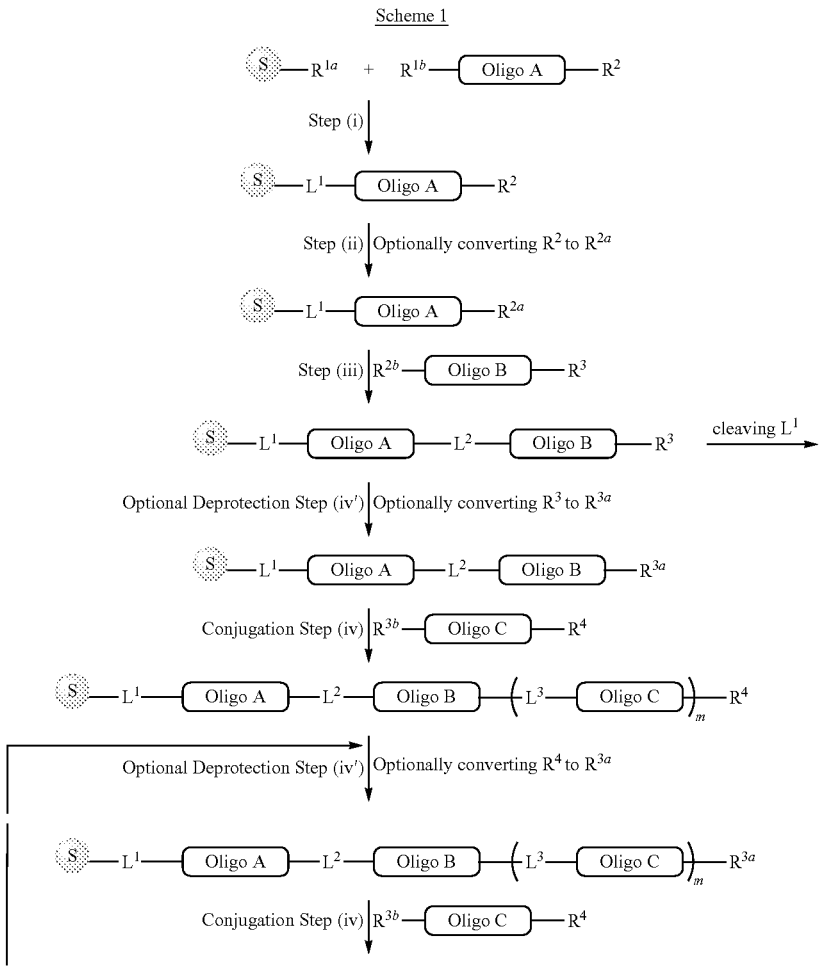

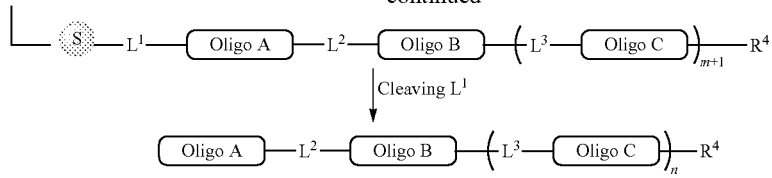

In Scheme 1, m is an integer starting from 1 and increasing by 1 after each optional deprotection and conjugation steps to a predetermined value "n". According to the protocol illustrated in Scheme 1, subscript "n" in the resin bound conjugated molecule is an integer between 0 and 25, for example, "n" can be 0, 1, 2, 3, 4, 5, 6, 7, 8, 9, 10, 12, 14, 16, 18, 20, 22, or 24. Other variables are as defined above.

Asymmetric Conjugation Methodology

In another aspect, is provided a method of preparing a compound of the formula

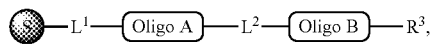

using an asymmetric conjugation strategy. According to this methodology, a conjugation component according to formula

is attached to a solid support

to form a compound of the formula

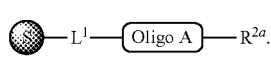

This intermediate then is allowed to react with a conjugation component of the formula

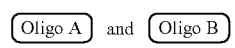

thereby to form

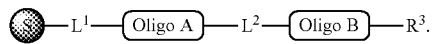

A solid support material

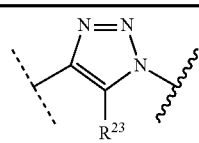

is used for synthesis, with each of

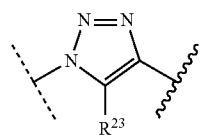

being selected independently from the category oligo described above.

$R^3$ is $R^{3a}$, a detectable label or an oligo. $R^{1a}$, $R^{1b}$ and $R^{2a}$, $R^{2b}$ are complementary conjugation functionalities, and $L^1$ and $L^2$ are conjugate linkers formed by reaction between $R^{1a}$ and $R^{1b}$ and between $R^{2a}$ and $R^{2b}$, respectively. $R^{1a}$, $R^{1b}$, $L^1$, $R^{2a}$, $R^{2b}$, $L^2$, and $R^{3a}$ are selected from:

| $R^{1a}$, $R^{2a}$, or $R^{3a}$ | $R^{1b}$ or $R^{2b}$ | $L^1$ or $L^2$ |
|---|---|---|
| —C≡C—$R^{23}$ | azido | triazole with $R^{23}$ |
| azido | —C≡C—$R^{23}$ | triazole with $R^{23}$ |
| carboxy | —NH$R^{23}$ | —C(=O)N$R^{23}$— |
| —NH$R^{23}$ | carboxy | —N$R^{23}$C(=O)— |
| halo | —NH$R^{23}$ | —N$R^{23}$— |

-continued

| $R^{1a}, R^{2a},$ or $R^{3a}$ | $R^{1b}$ or $R^{2b}$ | $L^1$ or $L^2$ |
|---|---|---|
| —$NR^{23}$ | halo | —$NR^{23}$— |
| hydroxy | —O—P(=O)(OH)(X) | —O—P(=O)(OH)—O— |
| —O—P(=O)(OH)(X) | hydroxy | —O—P(=O)(OH)—O— |
| —$NHR^{23}$ | —O—P(=O)(OH)(X) | —$NR^{23}$—P(=O)(OH)—O— |
| —O—P(=O)(OH)(X) | —$NHR^{23}$ | —O—P(=O)(OH)—$NR^{23}$— |
| thio | —O—P(=O)(OH)(X) | —S—P(=O)(OH)—O— |
| —O—P(=O)(OH)(X) | thio | —O—P(=O)(OH)—S— |
| thiol | —X | —S— |
| —X | thio | —S— |
| —O—P(=O)(OH)SH | —X | —O—P(=O)(OH)—S— |
| —X | —O—P(=O)(OH)SH | —S—P(=O)(OH)—O— |
| —$(CR^{25}R^{25})_sC$(=O)$OR^{23}$ | —$NHR^{23}$ | —$(CR^{25}R^{25})_sC$(=O)$NR^{23}$— |
| —$NHR^{23}$ | —$(CR^{25}R^{25})_sC$(=O)$OR^{23}$ | —$NHR^{23}C$(=O)—$(CR^{25}R^{25})_s$— |
| thio | 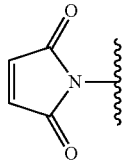 [SMILES: *N1C(=O)C=CC1=O] | 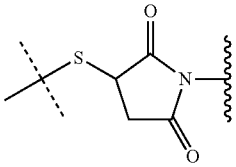 |
| 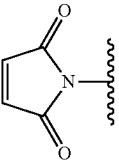 | thio | 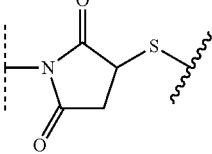 |
| —SH | —O—P(=O)(OH)(O—$(CH_2)_n$—SH) | —O—P(=O)(OH)(O—$(CH_2)_n$—S—S— |

X is a group selected from chlorine, bromine, fluorine, tosylate, mesylate, triflate, or dimethoxy triflate and the selection of $R^{1a}$, $R^{2a}$, or $R^{3a}$ are independent of each other provided that $L^1$ and $L^2$ are different, $R^{2a}$ does not react with $R^{1a}$ or $R^{1b}$, and $R^{3a}$ does not react with $R^{2a}$ or $R^{2b}$;

$R^{23}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloalkynyl, substituted cycloalkynyl, heteroaryl, substituted heteroaryl, heterocyclic, and substituted heterocyclic; and

- - - represents the point of connection to the part of the solid support-bound conjugated molecule that is closer to

, while ∿∿∿ represents the point of connection to the part of the solid support-bound conjugated molecule that is further away from

.

In accordance with the invention, a method also is provided for the manufacture of a solid support-bounded conjugated molecule according to the following formula:

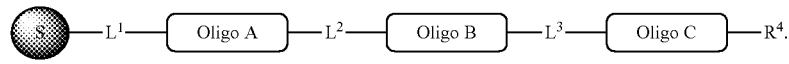

According to this method, a compound according to formula

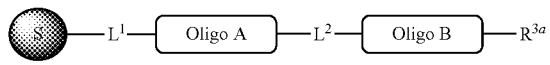

is reacted with a conjugation component

to obtain the following polymer

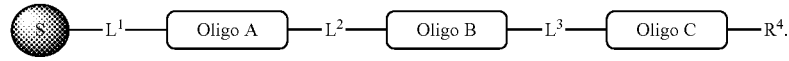

$R^4$ in such as polymer can be a conjugation functionality selected from the definitions for conjugation functionalities $R^{1a}$, $R^{2a}$, or $R^{3a}$, provided above, a detectable label or a polymer encompassed by the category oligo described above, provided that $R^4$ does not react with $R^{3a}$ or $R^{3b}$.

Upon completion of the synthesis, the target polymer is cleaved from the solid support using a suitable cleavage method to give

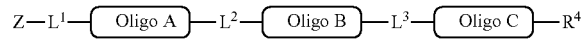

where Z is selected from —OH, OH—($C_1$-$C_{10}$)alkylene-, —COOH, $NH_2C(O)$—, $NH_2NH$—C(O)—, COOH—($C_1$-$C_{10}$)alkylene-, $NH_2C(O)$—($C_1$-$C_{10}$)alkylene-, $NH_2NH$—C(O)—($C_1$-$C_{10}$)alkylene-, $CH_2$=CH—($C_1$-$C_{10}$)alkylene-, C≡C—($C_1$-$C_{10}$)alkylene- or HS—($C_1$-$C_{10}$)alkylene- and the alkylene can be optionally substituted by one or more groups selected from —OH, halogen, —NHR", —NHC(O)—($C_1$-$C_{10}$)alkylene-C≡CH, or —NHC(O)—($C_1$-$C_{10}$)alkylene-CH=$CH_2$. When the alkylene is substituted with an —NHR" group, variable R" is selected from ($C_1$-$C_{10}$)alkyl, ($C_3$-$C_{10}$)cycloalkyl, or ($C_3$-$C_{10}$)aryl. Reagents that are useful for cleaving the oligo product from the solid support are similar to the ones described above.

In some embodiments, the method further comprises repeating the conjugation step "n" times to form a solid support-bound conjugated molecule according to the following formula:

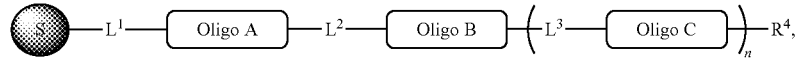

wherein n is an integer of equal to or greater than 1, and each

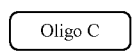

is independently selected from the category oligo described above.

In the above method, the intermediate product after each conjugation step has a terminal group $R^4$. When the $R^4$ is a conjugation functionality $R^{3a}$, this group permits the intermediate to react in subsequent conjugation steps with a complementary conjugation functionality $R^{3b}$ that is present on one end of a conjugation component of the formula:

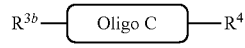

to add

to the solid support-bound conjugated molecule.

After completion of the reaction sequence, the bond $L^1$ that binds the desired product to the solid support is cleaved under suitable cleavage conditions to give a conjugated molecule of the formula:

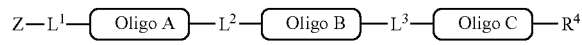

where the terminal group Z is defined above.

Each set of $R^{3a}$, $R^{3b}$, and $L^1$ is independently selected from
(a") $R^{3a}$ is azido, $R^{3b}$ is —C≡C—$R^{23}$, and $L^3$ is

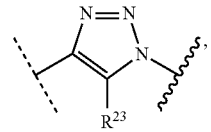

or
(b") $R^{3a}$ is —$NHR^{23}$, $R^{3b}$ is carboxy, and $L^3$ is —C(=O)$NR^{23}$—, or
(c") $R^{3a}$ is carboxy, $R^{3b}$ is —$NHR^{23}$, and $L^3$ is —C(=O)$NR^{23}$—, or
(d") $R^{3a}$ is —$NHR^{23}$, $R^{3b}$ is halo, and $L^3$ is —$NR^{23}$—, or
(e") $R^{3a}$ is —O—P(=O)(OH)(X), $R^{3b}$ is hydroxy, and $L^3$ is —O—P(=O)(OH)—O—, or
(f") $R^{3a}$ is —O—P(=O)(OH)(X), $R^{3b}$ is —$NHR^{23}$, and $L^2$ is —$NR^{23}$—P(=O)(OH)—O—, or
(g") $R^{3a}$ is —O—P(=O)(OH)(X), $R^{3b}$ is thio, and $L^3$ is —S—P(=O)(OH)—O—, or
(h") $R^{3a}$ is —X, $R^{3b}$ is thio, and $L^3$ is —S—, or
(i") $R^{3a}$ is

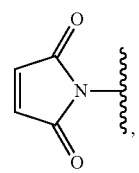

$R^{3b}$ is thio, and $L^3$ is

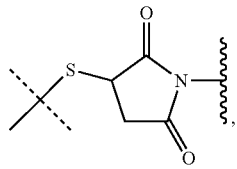

or (j") $R^{3a}$ is —C≡C—$R^{23}$, $R^{3b}$ is azido, and $L^3$ is

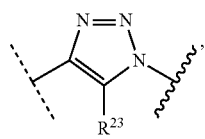

or (k") $R^{3a}$ is halo, $R^{3b}$ is —$NHR^{23}$, and $L^1$ is —$NR^{23}$—, or
(l") $R^{3a}$ is hydroxy, $R^{3b}$ is —O—P(=O)(OH)(X), and $L^3$ is —O—P(=O)(OH)—O—, or
(m") $R^{3a}$ is —$NHR^{23}$, $R^{3b}$ is —O—P(=O)(OH)(X), and $L^3$ is —O—P(=O)(OH)—$NR^{23}$—, or
(n") $R^{3a}$ is thio, $R^{3b}$ is —O—P(=O)(OH)(X), and $L^3$ is —O—P(=O)(OH)—S—, or
(o") $R^{3a}$ is —O—P(=O)(OH)SH, $R^{3b}$ is —X, and $L^3$ is —O—P(=O)(OH)—S—, or
(p") $R^{3a}$ is —X, $R^{3b}$ is —O—P(=O)(OH)SH, and $L^3$ is —O—P(=O)(OH)—S—, or
(q") $R^{3a}$ is —$(CR^{25}R^{25})_s C(=O)OR^{23}$, $R^{3b}$ is —$NHR^{23}$, $L^3$ is —$C(=O)NR^{23}$—,
(r") $R^{3a}$ is —$NHR^{23}$, $R^{3b}$ is —$(CR^{25}R^{25})_s C(=O)OR^{23}$, $L^3$ is —$NR^{23}C(=O)$—, or (s") $R^{3a}$ is thio, $R^{3b}$ is —X, and $L^3$ is —S—, or
(t") $R^{3a}$ is thio, $R^{3b}$ is

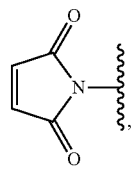

and $L^3$ is

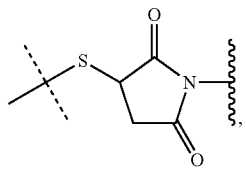

or (u") $R^{3a}$ is —SH, $R^{3b}$ is —O—P(=O)(OH)(O—$(CH_2)_n$—SH) and $L^3$ is —S—S—$(CH_2)$—O—P(OH)(=O)—O—, where group X in conjugation functionalities $R^{3a}$ and $R^{3b}$ is as defined above.

An embodiment of this process is illustrated in Scheme 2. In Scheme 2, m is an integer starting from 1 and increasing by 1 after each conjugation step until a conjugated molecule having the prescribed number ("n") of oligo units is obtained, where "n" is an integer between 0 and 25, for example, "n" can be 0, 1, 2, 3, 4, 5, 6, 7, 8, 9, 10, 12, 14, 16, 18, 20, 22, or 24. The definitions for variables $R^{1a}$, $R^{1b}$, $R^{2a}$, $R^{2b}$, $R^{3a}$, $R^3$ band $R^4$ are as defined above.

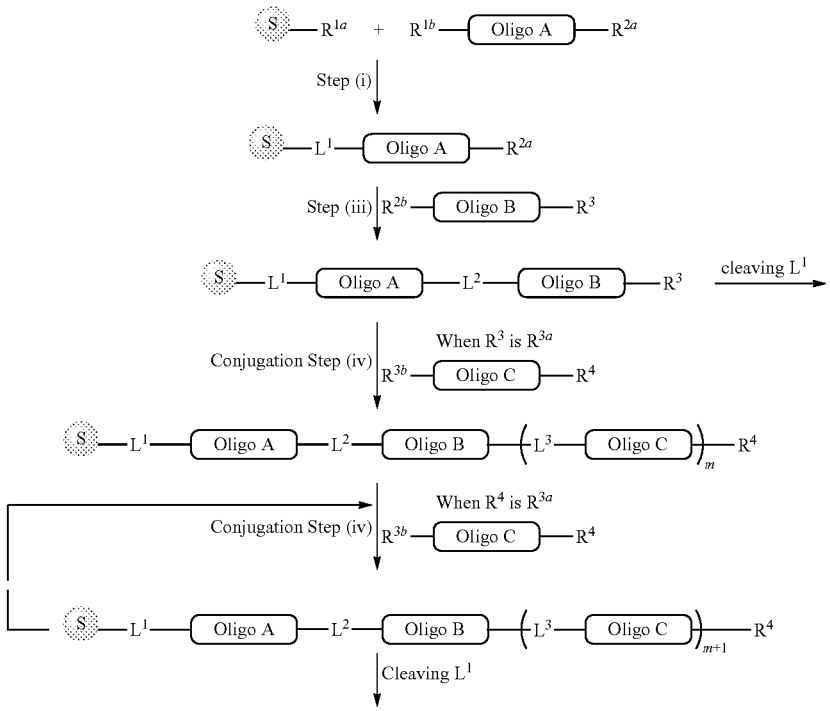

-continued

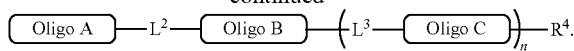

Symmetric Conjugation Methodology

In still another aspect, provided herewith is a method of preparing a compound of the formula

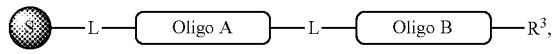

comprising (i) attaching a conjugation component of the formula

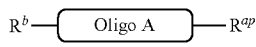

to a solid support

to form a compound of the formula

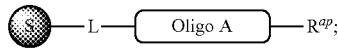

(ii) converting

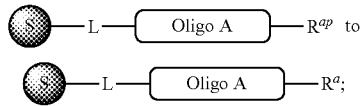

and
(iii) reacting

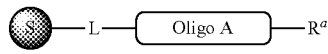

with a conjugation component of the formula

to form

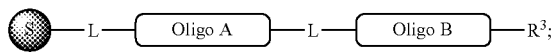

where:

is a solid support material;

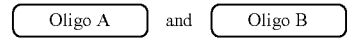

are each independently selected from polymers encompassed by the category oligo defined above;

According to this synthetic methodology, $R^3$ can either be a protected conjugation functionality $R^{ap}$, or $R^3$ is a group selected from a detectable label or a polymer of the categoty oligo. $R^a$ and $R^b$ are complementary conjugation functionalities and L is conjugate linker formed by reaction of $R^a$ and $R^b$. $R^{ap}$, $R^a$, $R^b$, and L are each independently selected from (a) $R^{ap}$ is halo, $R^a$ is azido, $R^b$ is —C≡C—$R^{23}$, and L is

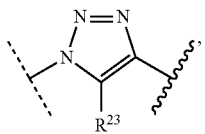

or (b) $R^{ap}$ is —$NR^{23}$Pr, $R^a$ is —$NHR^{23}$, $R^b$ is carboxy, and L is —$NR^{23}$C(=O)—, or
(c) $R^{ap}$ is carboxy ester, $R^a$ is carboxy, $R^b$ is —$NHR^{23}$, and L is —C(=O)$NR^{23}$—, or
(d) $R^{ap}$ is —$NR^{23}$Pr, $R^b$ is —$NHR^{23}$, $R^b$ is halo, and L is —$NR^{23}$—, or
(e) $R^{ap}$ is —OH, phosphate or phosphate ester, $R^a$ is —O—P(=O)(OH)(X), $R^b$ is hydroxy, and L is —O—P(=O)(OH)—O—, or
(f) $R^{ap}$ is —OH, phosphate or phosphate ester, $R^a$ is —O—P(=O)(OH)(X), $R^b$ is —$NHR^{23}$, and L is —O—P(=O)(OH)—$NR^{23}$—, or
(g) $R^{ap}$ is —O—P(=O)(OH)$SR^2$, $R^a$ is —O—P(=OX)OH)SH, $R^b$ is —X, and $L^2$ is —O—P(=O)(OH)—S—, or
(h) $R^{ap}$ is —OH, phosphate or phosphate ester, $R^a$ is —O—P(=O)(OH)(X), $R^b$ is thio, and L is —O—P(=O)(OH)—S—
(i) $R^{ap}$ is —$SR^{24}$, $R^a$ is —SH, $R^b$ is HS—$(CH_2)_n$—O—P(OH)(=O)—O— and L is —S—S—$(CH_2)_n$—O—P(OH)(=O)—O—;

$R^{23}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloalkynyl, substituted cycloalkynyl, heteroaryl, substituted heteroaryl, heterocyclic, and substituted heterocyclic;

X is selected from chlorine, bromine, fluorine, tosylate, mesylate, triflate, or dimethoxy triflate;

Pr is an amino protecting group;

$R^{24}$ is trityl or benzyl;

- - - represents the point of connection to the part of the solid support-bound conjugated molecule that is closer to

and 〰 represents the point of connection to the part of the solid support-bound conjugated molecule that is further away from

.

In another of its aspects, the present invention provides a method for preparing a solid support-bound conjugated molecule of the formula:

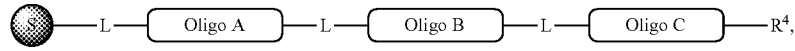

where the compound of formula

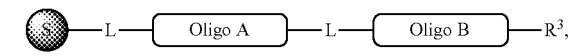

in which $R^3$ is a protected functional group $R^{ap}$ is deprotected to obtain a reactive intermediate

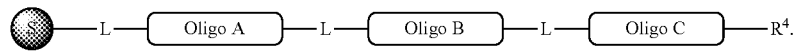

which subsequently is contacted with a conjugation component according to formula:

$R^b$—[ Oligo C ]—$R^4$, to form

In this embodiment, $R^4$ is selected from the group consisting of $R^{ap}$, a detectable label or a polymer from category oligo.

The bond L that binds the desired product to the solid support can be cleaved under suitable cleavage conditions to give a conjugated molecule of the formula:

Z—L—[ Oligo A ]—L—[ Oligo B ]—L—[ Oligo C ]—$R^4$.

In some embodiments, the method further comprises repeating the deprotection and conjugation steps "n" times to form a solid support-bound conjugated molecule of the formula:

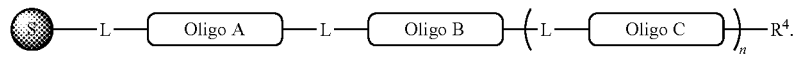

Integer n in the product obtained using the described method can have a value equal to or greater than 1, and each

is independently selected from polymers within the category oligo.

According to the above-described method, the intermediate product after each conjugation step has a terminal group $R^4$. When the $R^4$ is $R^{ap}$, $R^4$ is first converted to a conjugation functionality $R^a$ and then is contacted with a complementary conjugation functionality $R^b$ that is present on one end of the conjugation component of the formula:

$R^b$—[ Oligo C ]—$R^4$, to add a

to the solid support-bound conjugated molecule.

After completing the synthesis to obtain a solid support-bound conjugated molecule that has the specified number of

groups, the bond L that binds the final product to the solid support is cleaved under suitable cleavage conditions to give a resin free conjugated molecule according to formula:

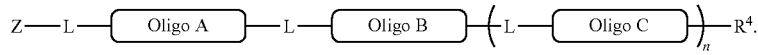

Depending on the nature of the solid support used for synthesis, terminal group Z in the resin free product is a group selected from —OH, OH—$(C_1-C_{10})$alkylene-, —COOH, $NH_2C(O)$—, $NH_2NH$—C(O)—, COOH—$(C_1-C_{10})$alkylene-, $NH_2C(O)$—$(C_1-C_{10})$alkylene-, $NH_2NH$—C(O)—$(C_1-C_{10})$alkylene-, $CH_2$=CH—$(C_1-C_{10})$alkylene-, C≡C—$(C_1-C_{10})$alkylene- or HS—$(C_1-C_{10})$alkylene- and the alkylene can be optionally substituted by one or more groups selected from —OH, halogen, —NHR", —NHC(O)—$(C_1-C_{10})$alkylene-C≡CH, or —NHC(O)—$(C_1-C_{10})$alkylene-CH—$CH_2$. Reagents suitable for cleaving the oligo are as defined above.

In this embodiment, all $R^{ap}$ are the same, all $R^a$ are the same, $R^b$ are the same, and each L is the same, and these variables are as defined above.

An embodiment of this process is illustrated in Scheme 3. In Scheme 3, "m" is an integer that starts from 1 and increases by 1, after each pair of deprotection and conjugation steps, until a conjugated molecule having the prescribed number ("n") of oligo units is obtained, where "n" is an integer between 0 and 25, for example, "n" can be 0, 1, 2, 3, 4, 5, 6, 7, 8, 9, 10, 12, 14, 16, 18, 20, 22, or 24. Other variables are as defined above.

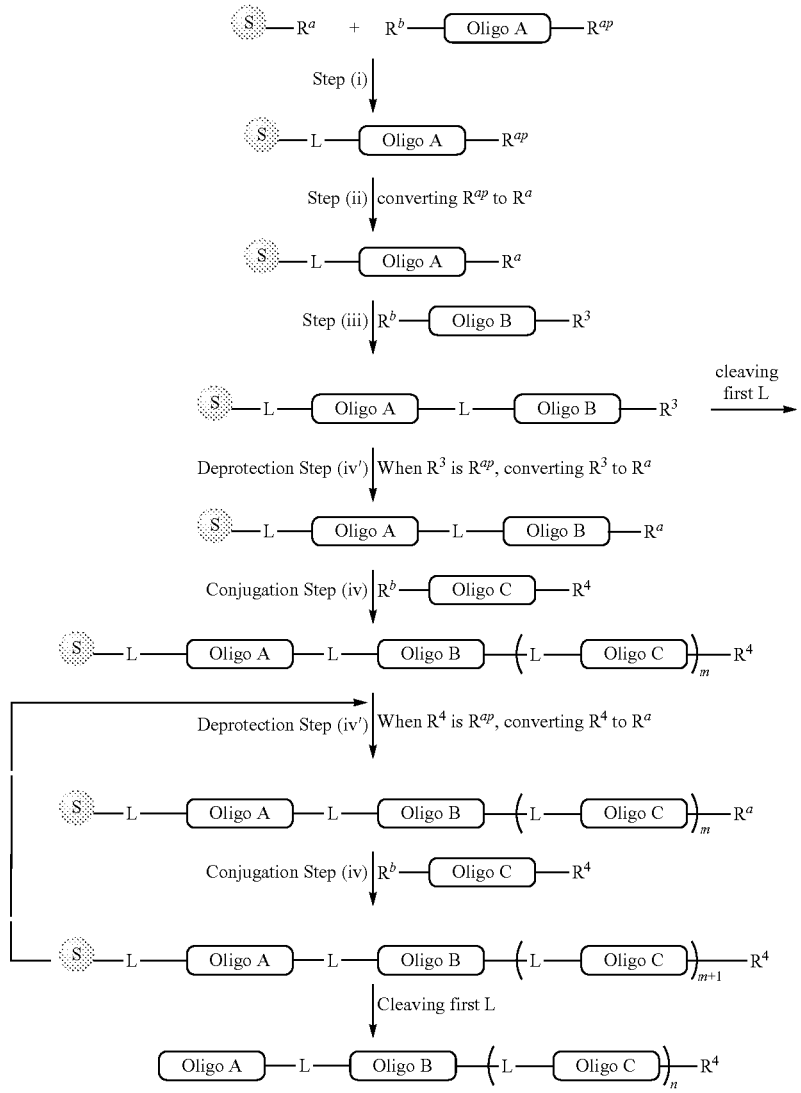

Scheme 3

In some embodiments of the inventive methodology, general, asymmetric or symmetric, $R^{23}$ is hydrogen or $C_{1-6}$ alkyl.

In some embodiments of the inventive methodology, general, asymmetric or symmetric, the conjugation functionalities and the conjugate linker are:

| $R^a$, $R^{1a}$, $R^{2a}$, or $R^{3a}$ | $R^b$, $R^{1b}$, $R^{2b}$ or $R^{3b}$ | L, $L^1$, $L^2$ or $L^3$ |
|---|---|---|
| —C≡C—H | azido | ![triazole] |
| azido | —C≡C—H | ![triazole] |
| carboxy | —NH₂ | —C(=O)NH— |
| —NH₂ | carboxy | —NHC(=O)— |
| halo | —NH₂ | —NH— |
| —NH₂ | halo | —NH— |
| hydroxy | —O—P(=O)(OH)(X) | —O—P(=O)(OH)—O— |
| —O—P(=O)(OH)(X) | hydroxy | —O—P(=O)(OH)—O— |
| —NH₂ | —O—P(=O)(OH)B(X) | —NH—P(=O)(OH)—O— |
| —O—P(=O)(OH)(X) | —NH₂ | —O—P(=O)(OH)—NH— |
| thio | —O—P(=O)(OH)(X) | —S—P(=O)(OH)—O— |
| —O—P(=O)(OH)(X) | thio | —O—P(=O)(OH)—S— |
| thio | —X | —S— |
| —X | thio | —S— |
| —O—P(=O)(OH)SH | —X | —O—P(=O)(OH)—S— |
| —X | —O—P(=O)(OH)SH | —S—P(=O)(OH)—O— |
| NHS ester | —NH₂ | —(CH₂)ₛC(=O)NH— |
| —NH₂ | NHS ester | —NHC(=O)—(CH₂)ₛ— |
| thio | maleimide | succinimide-thioether |
| maleimide | thio | succinimide-thioether |
| —SH | —O—P(=O)(OH)(O—(CH₂)ₙ—SH) | —O—P(=O)(OH)(O—(CH₂)ₙ—S—S— |

Conjugation Components

In another aspect, the invention provides a solid support represented by the formula:

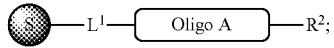

wherein:

is a solid support material;

Oligo A is selected from the category oligo;

$R^2$ is $R^{2a}$ or $R^{2ap}$;

$R^{2ap}$ is selected from the group consisting of halo, $NR^{23}Pr$, carboxy ester, $-NR^{23}Pr$, $-OH$, phosphate, phosphate ester, and $-O-P(=O)(OH)SR^{24}$, $R^{2a}$ is selected from the group consisting of halo, azido, hydroxy, thio, $-NHR^{23}$, carboxy, $-NHR^{23}$, $-O-P(=O)(OH)(SH)$,

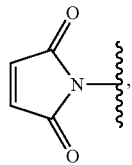

$-C\equiv C-R^{23}$, and $-(CR^{25}R^{25})_sC(=O)OR^{23}$;

$R^{23}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloalkynyl, substituted cycloalkynyl, heteroaryl, substituted heteroaryl, heterocyclic, and substituted heterocyclic;

Pr is an amino protecting group;

$R^{24}$ is trityl or benzyl;

$R^{25}$ is hydrogen or $C_{1-6}$ alkyl;

s is an integer of greater than 1; and

∼ represents the point of connection to

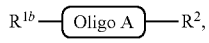.

In another aspect, the invention provides a compound according to formula:

$R^{1b}$—[Oligo A]—$R^2$, wherein $R^2$ is $R^{2a}$ or $R^{2ap}$,

[Oligo A]

is selected from the category oligo;

$R^{1b}$ is selected from the group consisting of $-C\equiv C-R^{23}$, carboxy, $-NHR^{23}$, halo, hydroxy, thio, azido, $-O-P(=O)(OH)(X)$, $-O-P(=O)(OH)SH$, $-(CR^{25}R^{25})_sC(=O)OR^{23}$, and

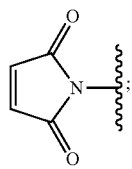

$R^{2ap}$ is selected from the group consisting of halo, $NR^{23}Pr$, carboxy ester, $-OH$, phosphate, phosphate ester, and $-O-P(=O)(OH)SR^{24}$;

$R^{2a}$ is selected from the group consisting of halo, azido, hydroxy, thio, $-NHR^{23}$, carboxy, $-O-P(=O)(OH)Br$,

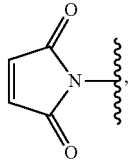

$-C\equiv C-R^{23}$, $-(CR^{25}R^{25})_sC(=O)OR^{23}$ and $-O-P(=O)(OH)SH$;

$R^{23}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloalkynyl, substituted cycloalkynyl, heteroaryl, substituted heteroaryl, heterocyclic, and substituted heterocyclic;

$R^{24}$ is trityl or benzyl;

Pr is an amino protecting group;

and ∼ represents the point of connection to

[Oligo A];

provided that $R^2$ does not react with $R^{1b}$.

Labels

Pursuant to the invention, a conjugated molecule or a components of such molecule can comprise one or more labels that are attached directly or through a linker. Such labeling can permit detection of the presence, the whereabouts and/or the quantitiy of a certain conjugation component or of conjugated molecules. For instance, the labeling can allow differentiation of different conjugation components or conjugated molecules in a nano-scale information processing system as above.

In this regard, a "label" is a group that can be detected by any means. Accordingly, the category of suitable labels includes but is not limited to fluorescent moieties, bioluminescent moieties, chemiluminescent moieties, colorimetric moieties, enzymatic moieties that generate a detectable signal when contacted with a substrate, spectrally resolvable quantum dots, metal nanoparticles or nanoclusters, paramagnetic, superparamagnetic and ferromagnetic substances, fluorophores, quenchers, and the like. A label also can be a group that carries a radioactive atom, such as Gallium-67 and Indium-111. In addition, a label can be polypeptide or protein that acts as a receptor or as a ligand for a cognate molecule the binding of which generates a detectable signal.

Examples of detectable moieties conjugated to another molecule are described in U.S. Pat. No. 4,855,225 and No. 5,188,934, in U.S. patent application publications No. 2005/0112065, No. 2007/0110798 and No. 2011/0077169, in published international application WO 1991/005060, and in Lee et al., *Nucleic Acids Res.* 20: 2471-483 (1992). Additionally, multiple detectable groups can be attached to a single conjugation component or to a conjugated molecule to provide a combined signal that allows the conjugation component or conjugated cmolecule to be identified and distinguished from others to which are attached a different detectable moiety or a different set of detectable groups. That such combinations of detectable groups are known is evidenced, for example, those described in U.S. Pat. No. 6,632,609 and in Speicher et al., *Nature Genetics* 12: 368-75 (1996).

Fluorophores, also known as fluorescent dyes, are detectable groups that absorb light energy at a defined excitation wavelength and emit light energy at a different wavelength.

Different fluorophores can be selected for use to give a mixture detectable groups that can be detected based on their spectral characteristics, particularly fluorescence emission wavelength and/or intensity, under certain detection conditions.

Quenchers are detectable groups that are capable of absorbing the energy of an excited fluorescent detectable group when located in close proximity with the excited fluorescent detectable group and of dissipating that energy without the emission of visible light. Examples of quenchers include, but are not limited to, DABCYL (4-(4'-dimethylaminophenylazo)benzoic acid) succinimidyl ester, diarylrhodamine carboxylic acid, succinimidyl ester (QSY-7), and 4',5'-dinitrofluorescein carboxylic acid, succinimidyl ester (QSY-33) (all available from Molecular Probes), quencher1 (Q1; available from Epoch), or "black hole quenchers" BHQ-1. BHQ-2, and BHQ-3 (available from BioSearch, Inc.).

In some embodiments, the detectable group is selected from:

| Name | Structure |
|---|---|
| pyrene azide (N-(3-Azidopropyl)-4-pyren-1-yl-butyramide) | 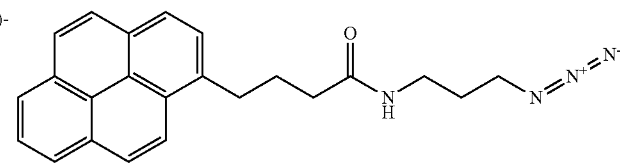 |
| hydroxy-coumarin azide (3-Azido-7-hydroxycoumarin) | 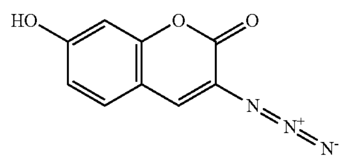 [SMILES: [N-]=[N+]=Nc1cc2ccc(O)cc2oc1=O] |
| 5-FAM azide (N-(3-azidopropyl)-3',6'-dihydroxy-3-oxo-3H-spiro[isobenzofuran-1,9'-xanthene]-5-carboxamide) | 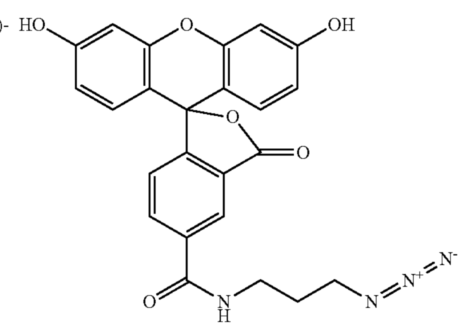 |
| Cy3 azide | 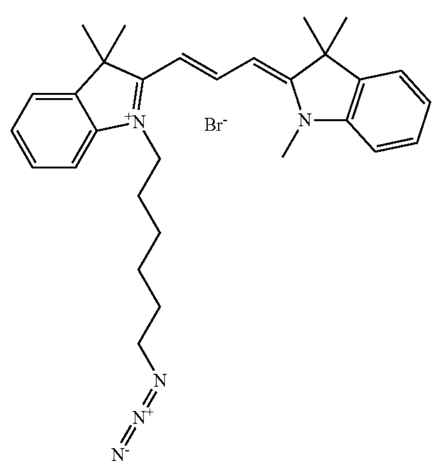 [SMILES: CN1/C(=C\C=C\C2=[N+](CCCCCCN=[N+]=[N-])c3ccccc3C2(C)C)C(C)(C)c2ccccc21 ; [Br-]] |

-continued
| Name | Structure |
|---|---|
| Cy5-azide | 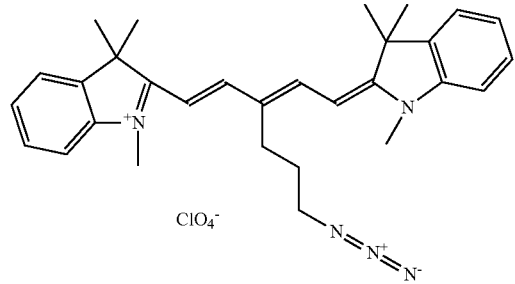 |
| TAMRA alkyne (5-Carboxytetramethylrhodamine, Propargylamide) | 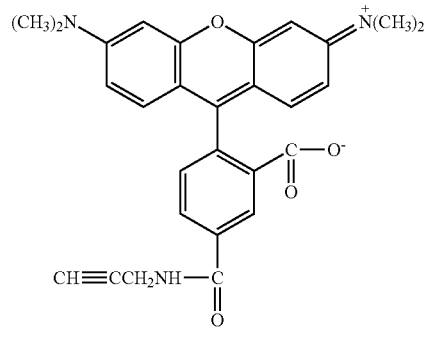 |
| 5-(Bromomethyl) Fluorescein | 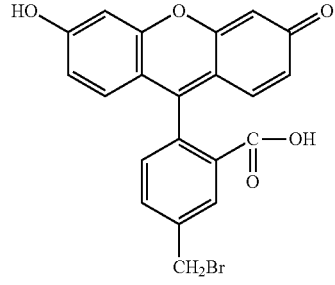 |
| Dabcyl Succinimidyl Ester (4-((4-(dimethylamino)phenyl)azo)benzoic Acid | 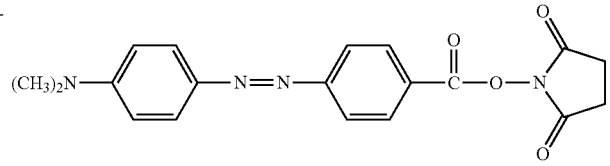 |
| Alexa Fluor 430 Carboxylic Acid, Succinimidyl Ester | 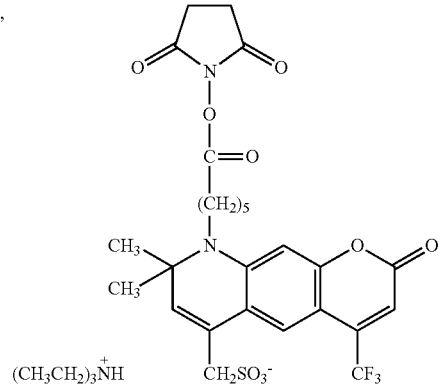 |

Use of the Conjugated Molecules

The conjugated molecules prepared by the methods described herein can be used to develop molecular processing networks, of different sizes and complexities, that are comprised of conditional nucleic acid-exchange reactions. The conjugated molecules also can be useful as biological transistors, which can constitute integrated circuits for executing compound logic functions, e.g., in diagnostic or therapeutic contexts that entail targeting of neoplastic or virus-infected cells. Thus, conjugated molecules of the invention can be employed to implement nano-scale information processing systems, suitable for solving computational problems in a test tube or in a cell. See U.S. patent application Ser. No. 13/072,438. As noted above, such nano-scale systems can be compatible with biological environments and have the potential for use in the diagnosis and treatment of complex diseases, among other applications.

Use of conjugated molecules of the invention in the manner described here typically will entail transport of the molecules into cells. Any methodology suitable for such intracellular delivery can be employed. Illustrative of reagents that promote delivery into cells of macromolecules, such as the conjugated molecules of the invention, are transfecting agents, liposomes, dendrimers, cholesterol, see Percot et al., *Int'l J. Pharm.* 278: 143-63 (2004), and delivery peptides and proteins, including polyamines such as carboxy spermine, poly-Arginine, poly-Lysine and the RGD peptide.

Thus, transport across a cell membrane could be achieved by coupling an inventive oligo covalently to a peptide that contains a cell internalization signal, a nuclear or sub-cellular localization signal, and/or a cell targeting and endocytosis-triggering signal. Such a peptide can be naturally-occurring or derived from synthetic or engineered proteins; e.g., the peptide can be a synthetic functional equivalent of naturally-occurring peptide. See Luo et al., *Nature Biotechnology* 18: 33-37 (2000), and U.S. Pat. No. 7,087,770.

Cell delivery peptides and proteins can be covalently linked to the inventive oligo by a disulfide likage. Typically, the cell delivery peptide containing a cysteine residue will be allowed to contact a free sulhydryl containing oligo under oxidative conditions to facilitate the formation of the disulfide linkage. The progress of the conjugation reaction and eventual purification of the conjugated product can be performed by HPLC, using a C-18 reverse-phase column, and mass spectral analysis for identification of the product.

According to one delivery strategy, a cell delivery peptide or protein will be first bound to the inventive oligo. The peptide- or protein-oligo complex then will be admixed with a transfection agent or mixture of agents, and the resulting mixture will be employed to deliver the oligo into cells. Suitable transfection agents include cationic lipid compositions, particularly monovalent and polyvalent cationic lipid compositions, more particularly LIPOFECTIN®, LIPOFECTAMINE®, CELLFECTIN®, DMRIE-C®, DOTAP®, and DOSPER®, and dendrimer compositions, particularly G5-G10 dendrimers, including dense star dendrimers, poly (amidoamine) dendrimers (PAMAM®), grafted dendrimers, and dendrimers known as dendrigrafts and SuperFect®.

General Synthetic Methods

The starting materials for preparing conjugated molecules according to the present invention include but are limted to, oligonucleotides, nucleotide monomers, peptides, proteins, amino acids, peptide nucleic acids and peptide nucleic acid derivatives. The starting materials can be purchased from commercial vendors or synthesized prior to use. The inventive conjugation components are prepared by functionalizing a polymer within the category oligo to contain one or two conjugation functionalities.

In the following examples preferred process conditions are given, i.e., reaction temperatures, times, mole ratios of reactants, solvents used and pressures. However, other process conditions can also be used unless otherwise stated. Optimum reaction conditions may vary depending on the reactants or solvents used, but such conditions can be determined by one skilled in the art by routine optimization procedures.

In addition to the protected groups described here, other conventional protecting groups may be necessary to prevent certain functional groups from undergoing undesired reactions. Suitable protecting groups for various functional groups as well as suitable conditions for protecting and deprotecting particular functional groups are well known in the art. For instance, numerous protecting groups are described in T. W. Greene and G. M. Wuts, PROTECTING GROUPS IN ORGANIC SYNTHESIS, Third Edition (Wiley, New York, 1999), and publications cited there.

Furthermore, various oligos may contain one or more chiral centers. Accordingly, conjugated molecules can be prepared or isolated as pure stereoisomers, i.e., as individual enantiomers or diastereomers, or as mixtures of stereoisomer, such racemic mixtures. All such stereoisomers and mixtures of stereoisomers are within the scope of this invention. Such compounds can be prepared using optically active starting materials, for instance, or stereoselective reagents. Alternatively, a mixture of two or more stereoisomers can be resolved using chiral column chromatography or chiral resolving agents.

Oligos that are oligonucleotides may be prepared by conventional solid-phase synthesis methodology, such as the phosphoramidite technique, which uses phosphoramidite building blocks derived from protected 2'-deoxynucleosides (dA, dC, dG, and T) and ribonucleosides (A, C, G, and U). To obtain a desired oligonucleotide, the building blocks are sequentially coupled to the growing oligonucleotide chain in the order required by the sequence of the product. Examples of such methods are described in Reese, *Organic & Biomolecular Chemistry* 3: 3851 (2005), Iyer et al., "Oligonucleotide synthesis" in COMPREHENSIVE NATURAL PRODUCTS CHEMISTRY, Vol. 7: DNA and Aspects of Molecular Biology; and Ogilvie; *J. Amer. Chem. Soc.* 99: 7741-43 (1997).

Peptides can be prepared from amino acids under amide coupling conditions, such as suing an amide coupling reagent. For example, the peptides can be prepared using a solid-phase methodology as those described in F. F. Nord and R. B. Merrifield, SOLID-PHASE PEPTIDE SYNTHESIS (Wiley 2006).

Peptide nucleic acids can be prepared according to conventional methods as described, for instance, in U.S. Pat. No. 5,539,082 and No. 6,395,474.

The various compounds described herein, such as conjugation components, intermediates, and conjugated molecules, may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

EXAMPLES

The examples that follow are provided to illustrate certain aspects of the present invention and to aid those of skill in the art in practicing the invention. The examples are not to be considered to limit the scope of the invention.

Example 1

A PNA Conjugation Component Conjugated with a DNA Conjugation Component

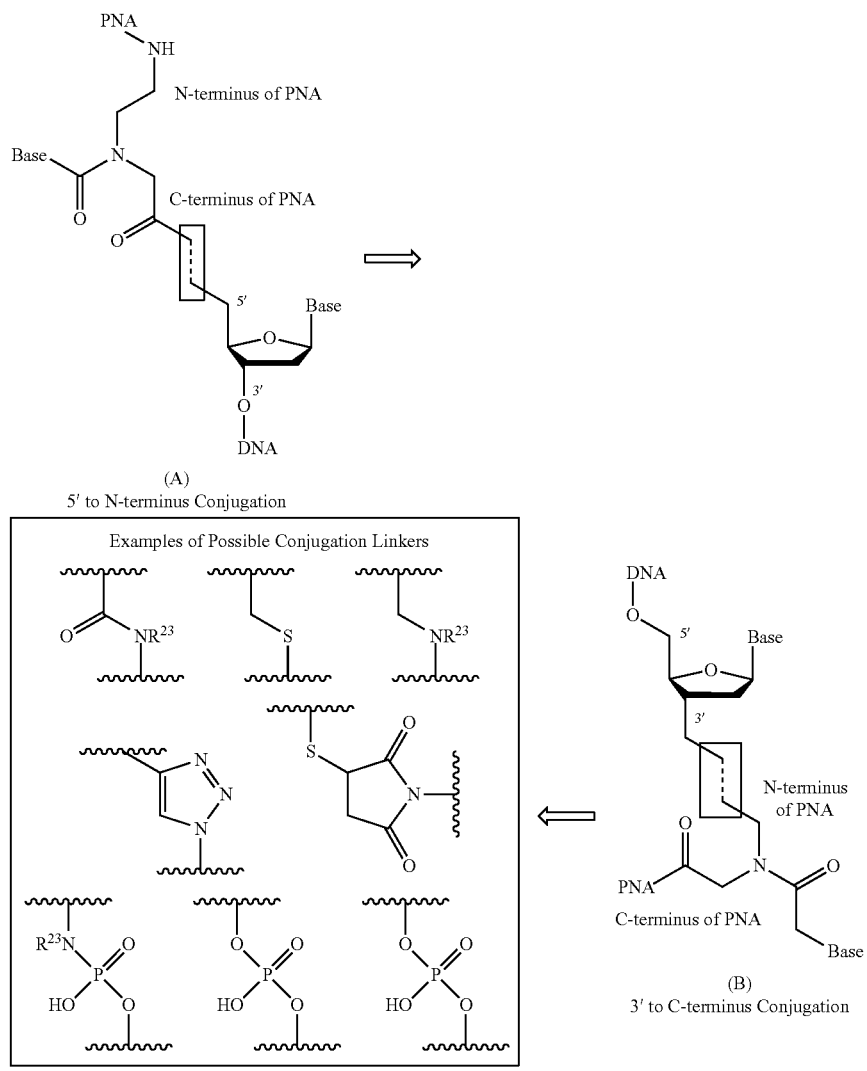

Scheme 4 above illustrates a general protocol for conjugating a DNA to a peptide nucleic acid to obtain a heteropolymer. In this scheme the 5'-terminal (5'-end) of an appropriately functionalized DNA is permitted to contact a reactive group on the C-terminus of a PNA moiety to synthesize a DNA-PNA heteropolymer (Scheme 4 path (A), 5' to N-terminal conjugation).

In one embodiment, the conjugation reaction proceeds by providing a nucleophilic group, for example, a thiol, amine, or hydroxide at the 5-terminus of the DNA and a suitable leaving group such as halogen, mesylate, or tosylate at the N-terminus of the PNA. Alternatively, conjugation can proceed by functionalizing the 5'-terminal of the Da to bear a suitable leaving group and allowing such a DNA moiety to react with a nucleophile attached to the N-terminus of a PNA. Pursuant to another aspect of the invention, conjugation of the DNA to the PNA can proceed via the formation of a disulfide bond or the formation of an amide (peptide) bond. Alternatively, an alkyne functionalized DNA can be contacted with an azide functionalized PNA to form a traizole ring that connects the 5-terminus of the DNA to the N-terminus of the PNA. Protocols for conjugating a DNA to a PNA via an amide linkage, thioether linkage, or triazine moiety are further described below.

The DNA-PNA heteropolymers thus obtained can be cleaved from the solid supports using a variety of cleaving reagent. Depending on the type of solid support used and therefore, the nature of the bond conjugating the DNA or the PNA to a support, strong and weak acids such as hydrogen fluoride, trifluoroacetic acid, trichloroacetic acid, bases such as ammonia, amines, or other reagents such as hydrazine, uv light, and hydidres can be used to cleave the heteropolymer from the supports. Typically, the cleaving reagent is used along with scavengers to prevent racemization of the product.

In the specific example illustrated below, the conjugation product (X) is cleaved from the support through an elimination reaction under basic conditions (concentrated ammonium hydroxide). The specific support used in this case is a 1000 angstrom Controlled Pore Glass (CPG) bead functionalized with the UnySupport linker commercially available from GlenResearch.

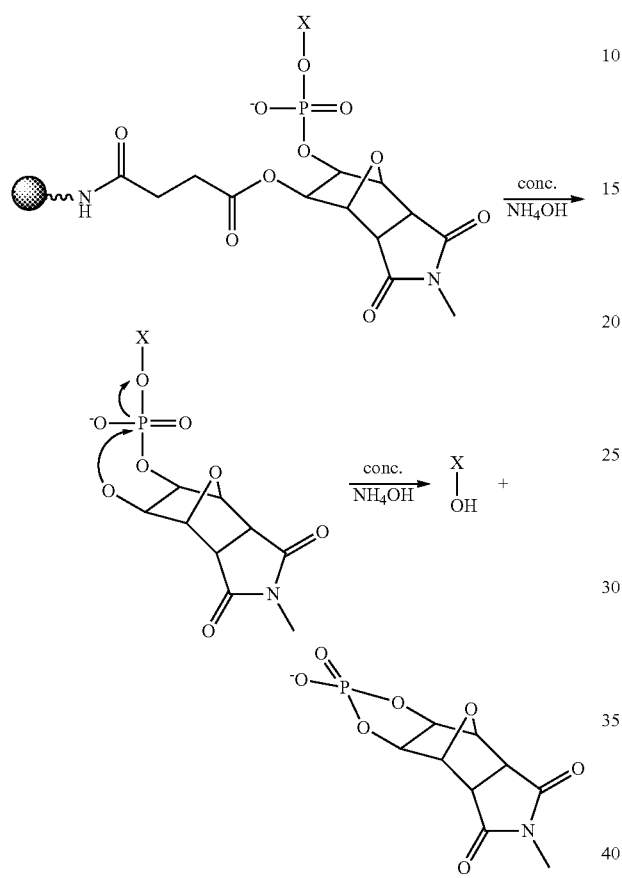

As described above the synthesis of a DNA-PNA heteropolymer having a 5' to N-terminal connectivity requires the 5'-end of the DNA to be suitable functionalized to facilitate the conjugation reaction with the N-terminal of a PNA moiety. Illustrative of groups that are suitable for functionalizing the 5'-terminal of DNA are those shown in Scheme 5 below where variable "A" represents the 5'-terminal group of a DNA.

Scheme 5

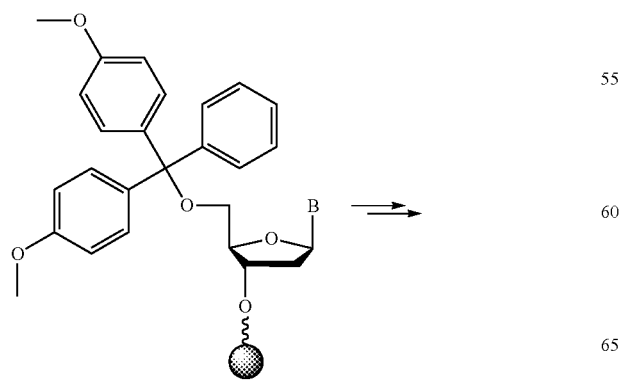

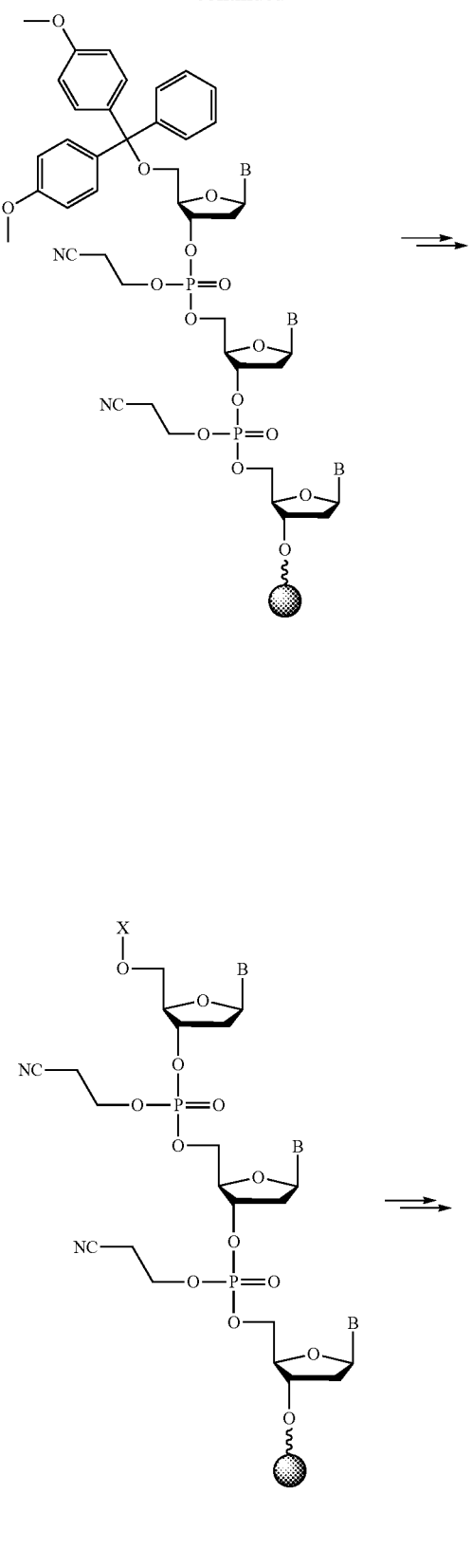

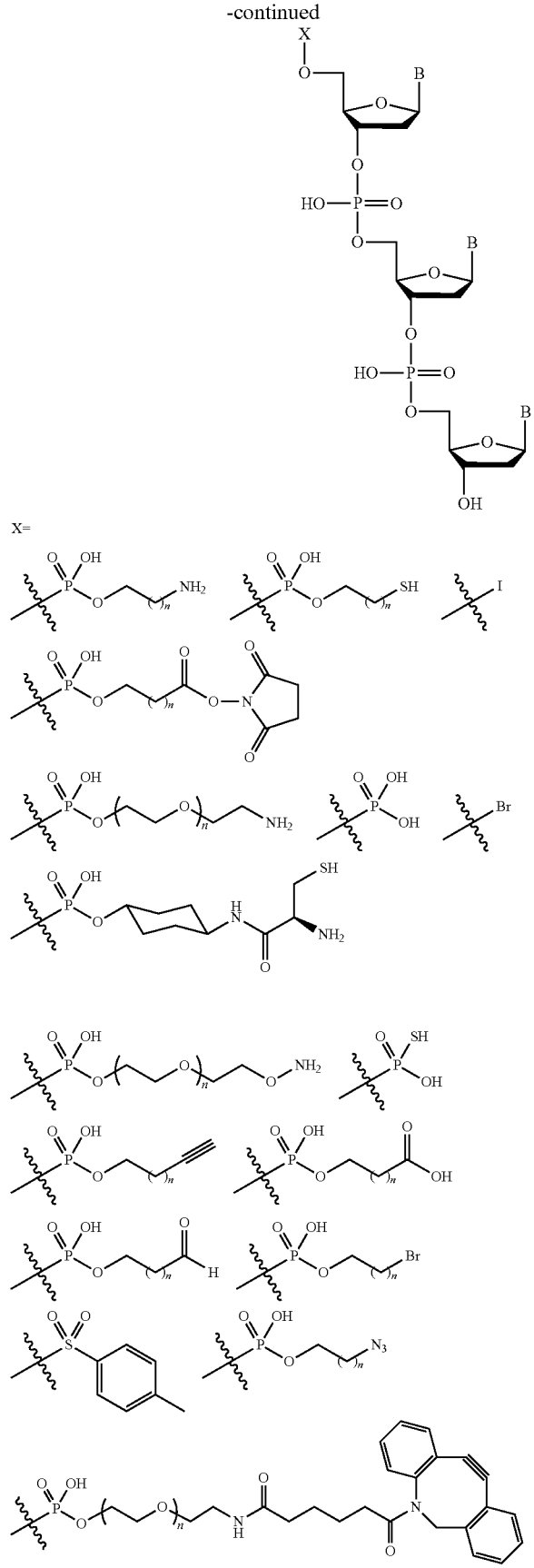

Methodologies for introducing functional groups illustrated in Scheme 5 above, at the 5'-terminal of a DNA are well know in the art See Isaac S. Marks et al., Bioconjugate Chemistry, (2011), 22(7), pp 1259-1263; Neal K. Devaraj et al., J Am Chem. Soc., (2005), 127(24), pp 8600-8601; Joseph G. Harrison and Shankar Balasubramanian, Nucl. Acids Res., (1998) 26 (13), pp 3136-3145; and Podyminogin M A et al., Nucleic Acids Res., (2001), 29(24), pp 5090-8. Alternatively, a DNA-PNA heteropolymer that has a 3' to C-terminal connectivity can be synthesized using a protocol similar to the one illustrated above in Scheme 4, path (B). The synthesis such a heteropolymer proceeds by introducing a functional group selected from one of the groups that define variable "A" in Scheme 5 above at the 3'-end of a DNA and contacting the functionalized DNA with a PNA whose C-terminus is separately functionalized to include a group that can react with the 3'-end of the DNA.

The PNa moiety that takes part in the conjugation reaction can be functionalized at the C-terminal or the N-terminal of the PNA molecule. FIGS. 3 and 4 illustrate reagents for N-terminal and C-terminal modifications of PNA's. Protocols for modifying the N- and C-terminii of PNA's using these reagents are well known in the chemical art. See Andriy A. Mokhir et al. Bioconjugate Chem., (2003), 14 (5), pp 877-883; Brian D. Gildea et al., Tetrahedron Letters, (1998), Volume 39, Issue 40, pp 7255-7258

Schemes 6-8 illustrate exemplary strategies for synthesizing a 3'-functionalized DNA. The product DNA's illustrated in each of Scheme 6-8 can be used to form the inventive DNA-PNA heteropolymer as further described below.

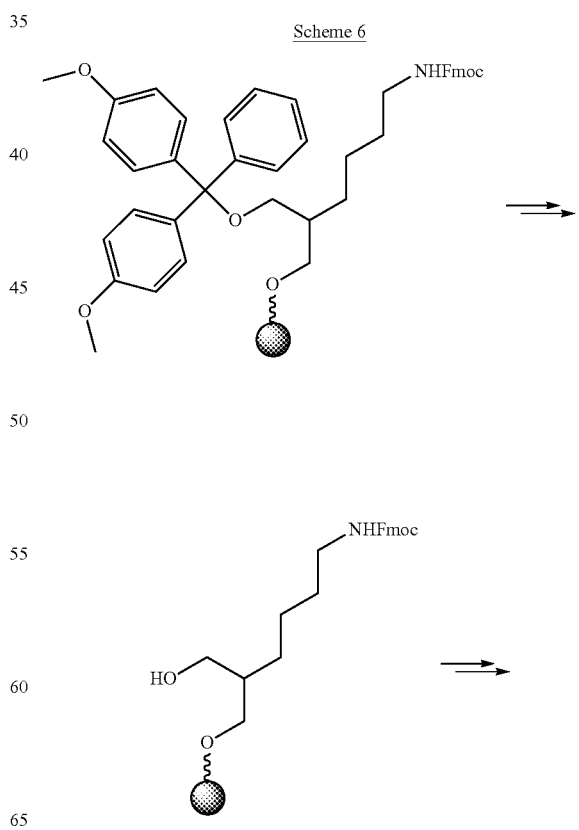

Scheme 6

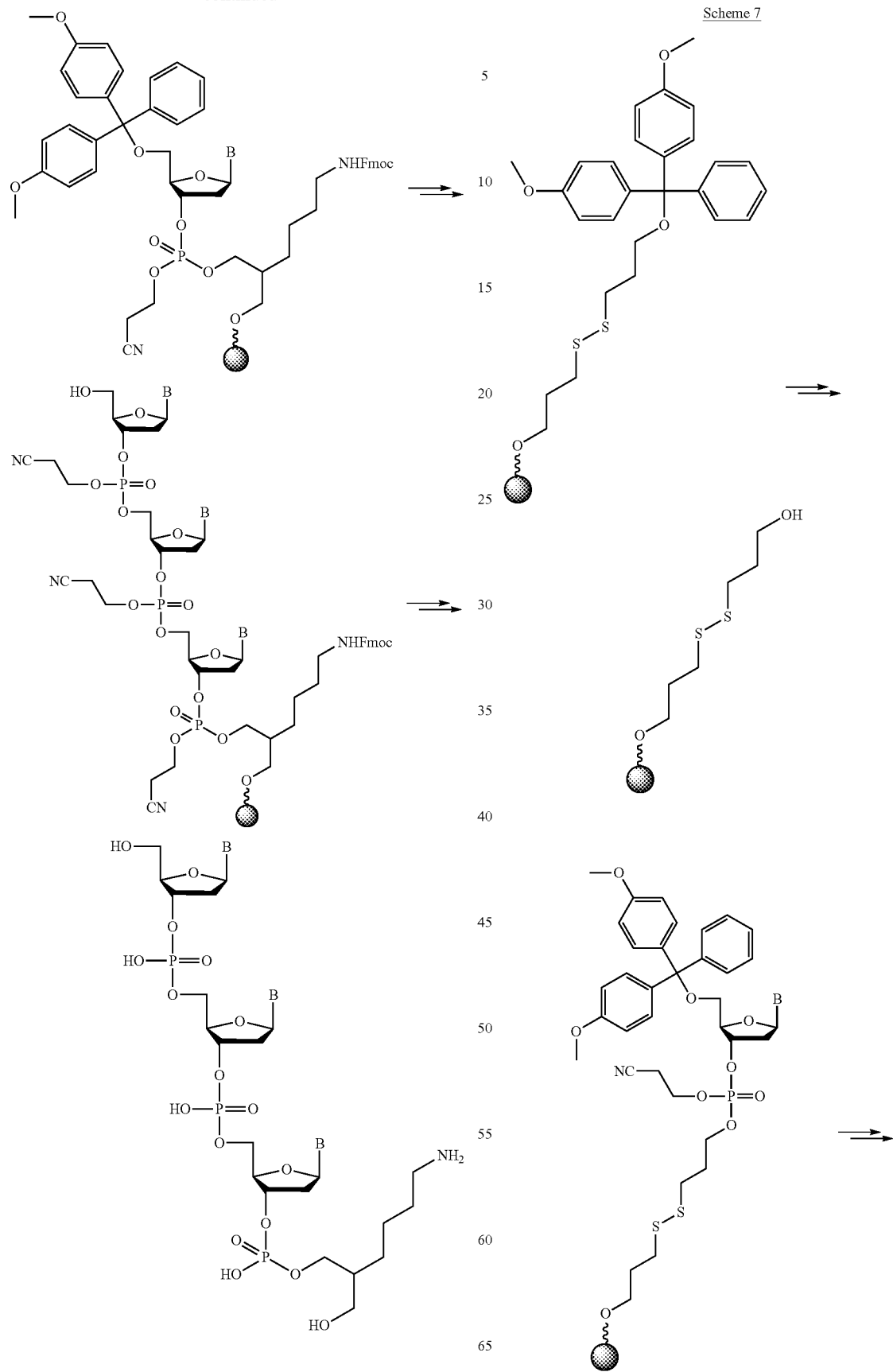

67 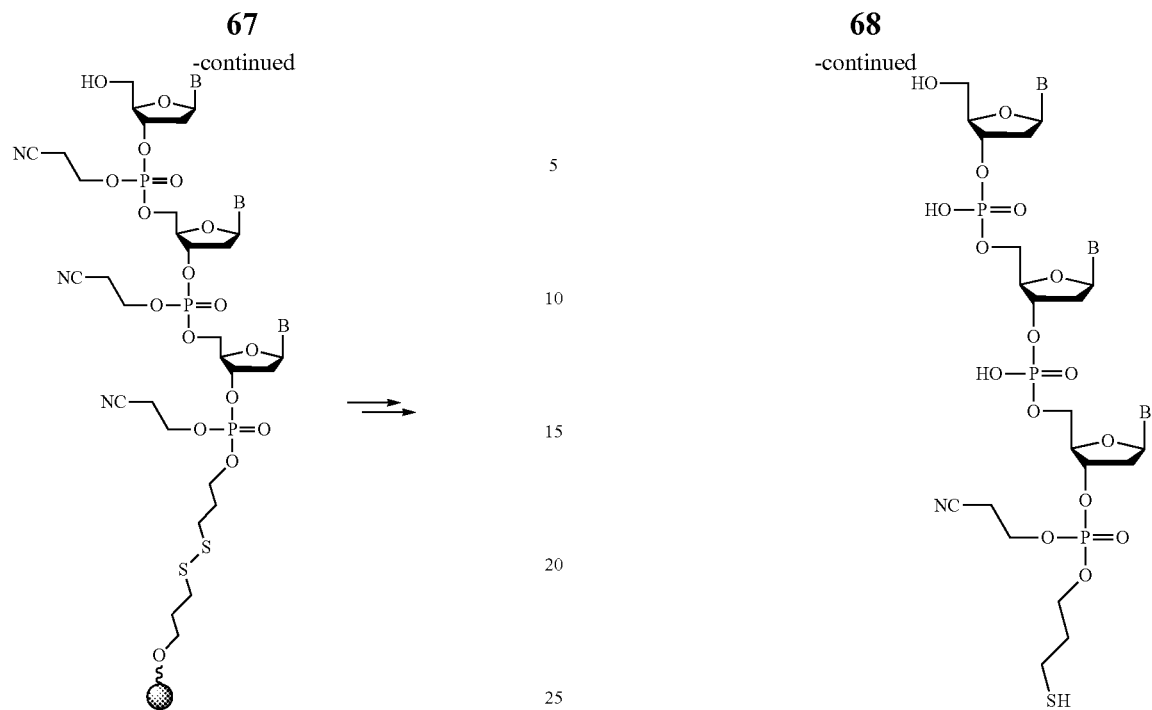 68
Scheme 8
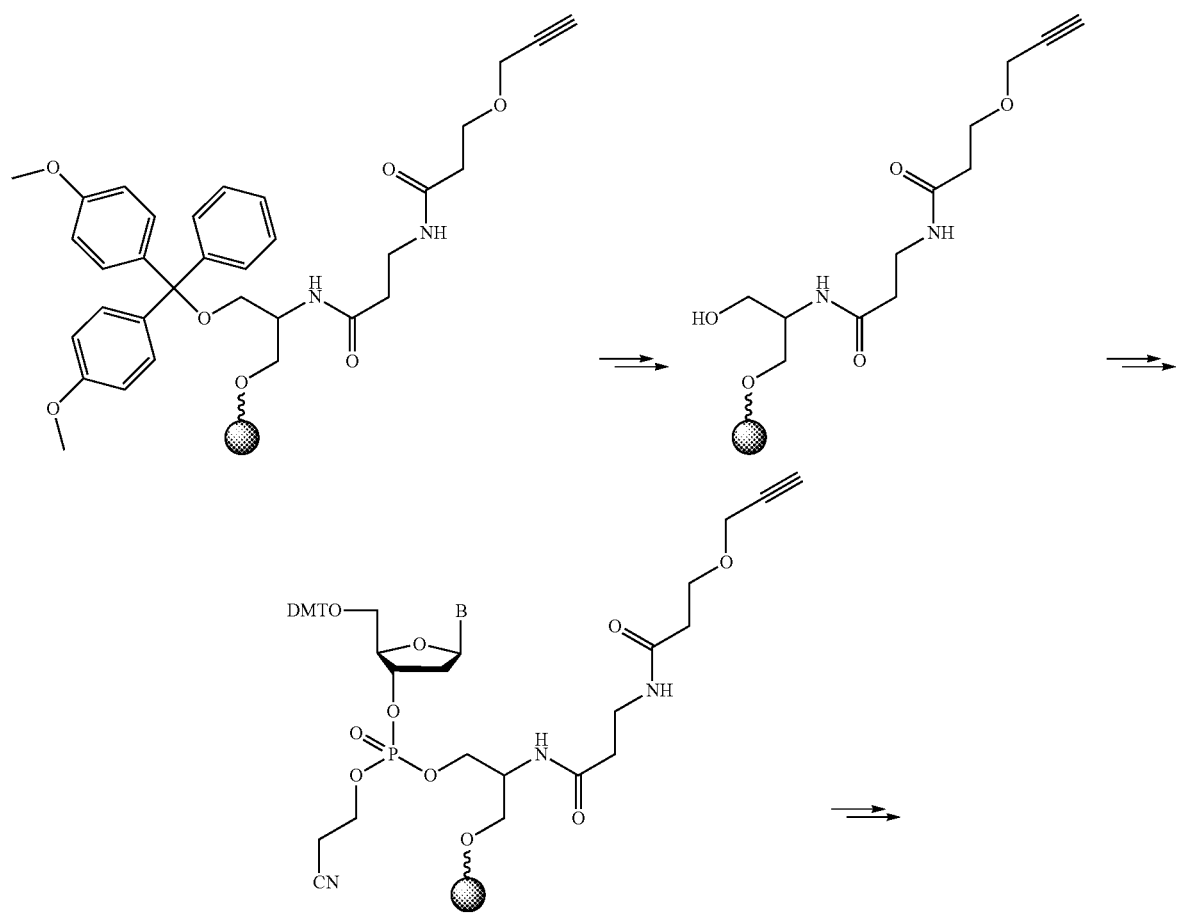

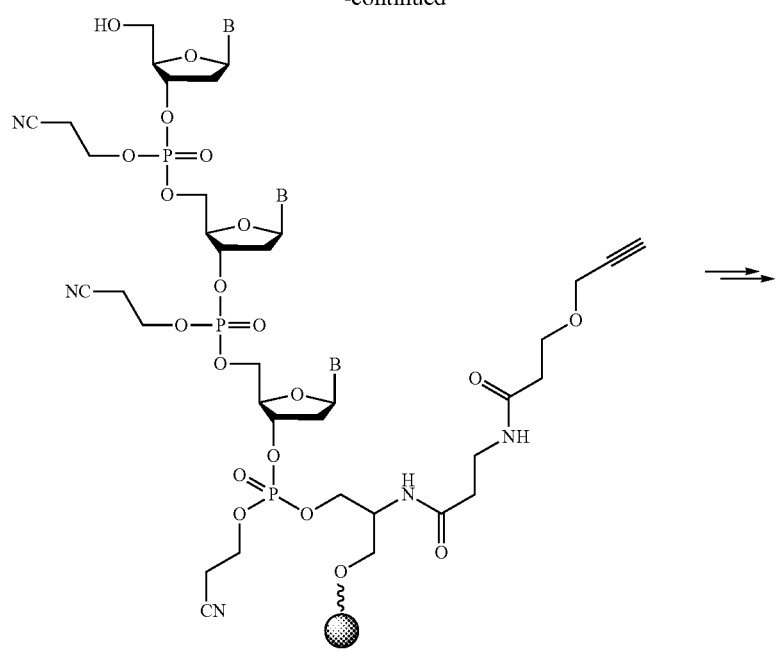
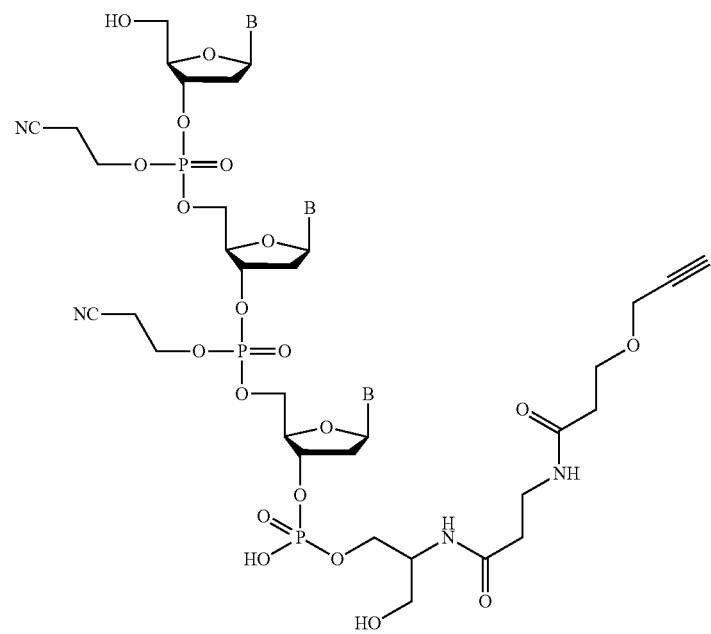

Example 2

Amide Conjugate Linker Formation (1)

Scheme 9 illustrates the synthesis of a DNA-PNA heteropolymer having a 5' to C-terminal connectivity.

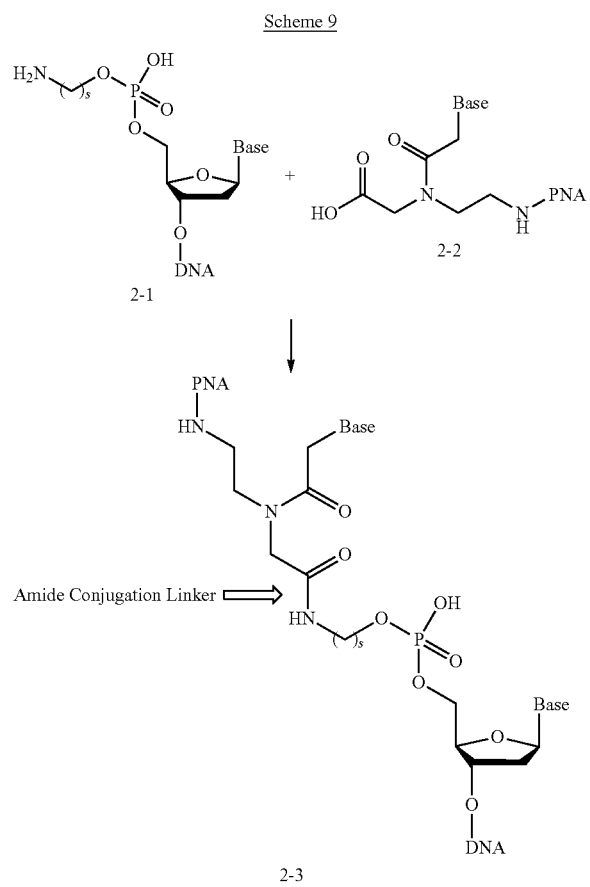

As illustrated above, the synthesis of the inventive conjugated molecule, that is, a DNA-PNA heteropolymer proceeds by contacting the amino group at 5'-end of the DNA (component 2-1) to the carboxyl group of a PNA (component 2-2). The product 2-3 is obtained through the formation of an amide bond using reaction conditions similar to those used for performing conventional amide-couplings. The numerical value of subscript "s" dictates the distance separating the PNA from the DNA in the final product and may influence the physical and/or biochemical properties of the heteropolymer.

Suitable coupling reagents for forming an amide bond include carbodiimides, such as N—N'-dicyclohexylcarbodiimide (DCC), N—N'-diisopropylcarbodiimide (DIPCDI), and 1-ethyl-3-(3'-dimethylaminopropyl)carbodiimide (EDCI). The carbodiimides may be used alone or along with additives that promote and improve coupling efficiency. Such coupling additives include without limitation dimethylaminopyridine (DMAP) or compounds belonging to the class benzotriazoles, e.g., 7-aza-1-hydroxybenzotriazole (HOAt), 1-hydroxybenzotriazole (HOBt), and 6-chloro-1-hydroxybenzotriazole (Cl-HOBt).

Amide coupling reagents also include amininum and phosphonium based reagents. Aminium salts include N-[(dimethylamino)-1H-1,2,3-triazolo[4,5-b]pyridine-1-ylmethylene]-N-methylmethanaminium hexafluorophosphate N-oxide (HATU), N-[(1H-benzotriazol-1-yl)(dimethylamino)methylene]-N-methylmethanaminium hexafluorophosphate N-oxide (HBTU), N-[(1H-6-chlorobenzotriazol-1-yl)(dimethylamino)methylene]-N-methylmethanaminium hexafluorophosphate N-oxide (HCTU), N-[(1H-benzotriazol-1-yl)(dimethylamino)methylene]-N-methylmethanaminium tetrafluoroborate N-oxide (TBTU), and N-[(1H-6-chlorobenzotriazol-1-yl)(dimethylamino)methylene]-N-methylmethanaminium tetrafluoroborate N-oxide (TCTU). Phosphonium salts include 7-azabenzotriazol-1-yl-N-oxy-tris(pyrrolidino)phosphonium hexafluorophosphate (PyAOP) and benzotriazol-1-yl-N-oxy-tris(pyrrolidino) phosphonium hexafluorophosphate (PyBOP). An amide formation step may be conducted in a polar solvent such as dimethylformamide (DMF), where the solvent also may include an organic base such as diisopropylethylamine (DIEA) or dimethylaminopyridine (DMAP).

Example 3

Amide Conjugate Linker Formation (2)

Heteropolymers having an amide linkage between the DNA and PNA units also are synthesized by permitting a PNA modified to have a free amino group at its C-terminus to contact a 5'-carboxyl DNA as illustrated below in Scheme 10.

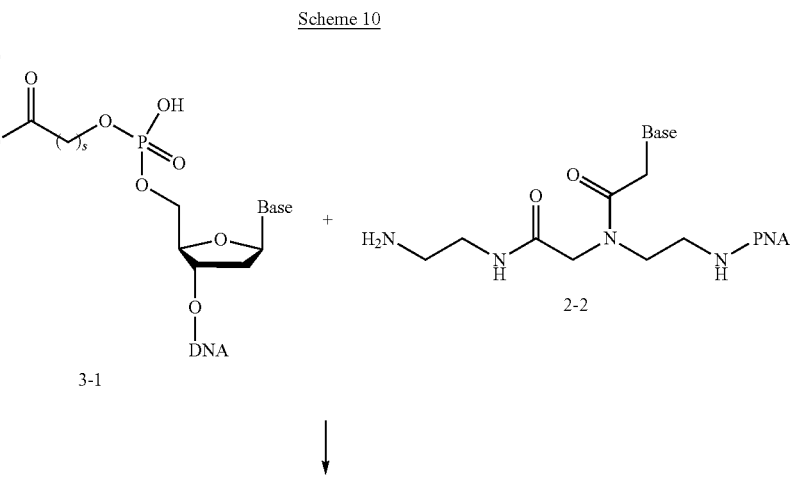

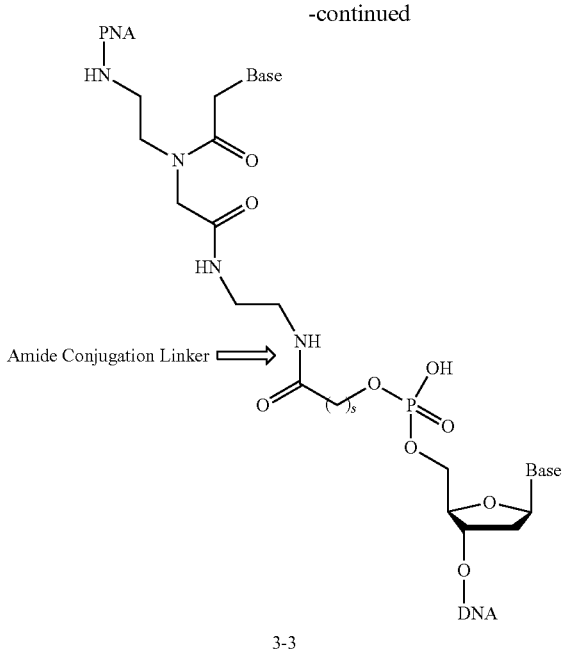

3-3

Briefly, the final product having an amide conjugate linker is formed by contacting the amino group PNA conjugation component 2-2 with a (2,5-dioxopyrrolidin-1-yl)oxycarbonyl conjugation functionality of at the 5'-end of DNA conjugation component 3-1.

Example 4

Triazole Conjugate Linker Formation (1)

Heteropolymers having a triazole linkage, such as component 4-3 in Scheme 11 below are synthesized by contacting a 3'-alkynyl modified DNA (component 4-1) with a N-terminal azide modified PNA (component 4-2).

Scheme 11

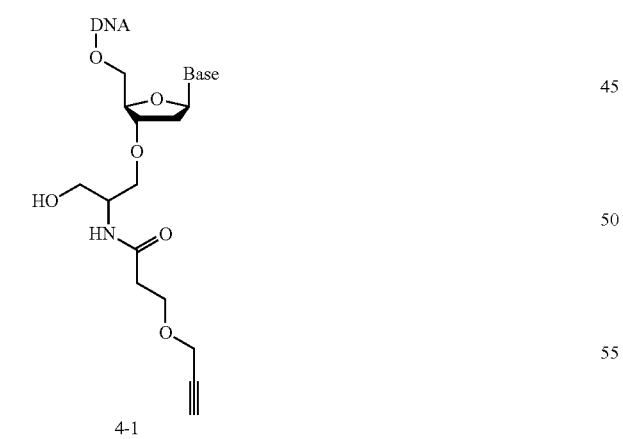

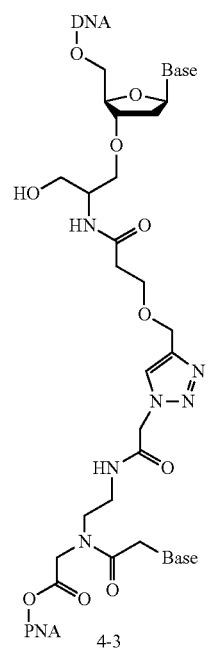

4-3

Alternatively, the DNA can be functionalized to have an alkynyl group at its 5'-end and an azide at the C-terminal end of a PNA. Briefly, synthesis proceeds as follows. The 5'-functionalized DNA is dissolved in a solution of water and alcohol. Typically the ratio of water to alcohol is in the range from 3:1 to 1:3. The choice of alcohol depends on the amount and chemical nature of the DNA being used. Exemplary alcohols include without limitation, ethanol, propanol, n-butanol, t-butanol and i-propanol. Other organic solvents such as dimethylformamide (DMF) can also be added to the aqueous-alcoholic DNA solution to enhance dissolution of DNA. A copper catalyst, such as copper sulfate or CuI is added to the DNA solution, followed by the addition of a buffered solution of the PNA azide. To aid the conjugation, cofactors such as tris-hydroxypropyltriazole can be added to the reaction mixture. The mole ratio of DNA to PNA in the reaction mixture can range from 1:1 to 1:3. The amount of DNA in the reaction mixture can be from about 1.0 nmoles to about 20 μmoles, for example about 50 nmoles, 100 nmoles, 150 nmoles, 200 nmoles, 250 nmoles, 300 nmoles, 350 nmoles, 400 nmoles, 500 nmoles, 600 nmoles, 700 nmoles, 800 nmoles, 900 nmoles, 1 μmole, 2 μmoles, 3 μmoles, 4 μmoles, 5 μmoles, 6 μmoles, 7 μmoles, 8 μmoles, 10 μmoles, 12 μmoles, 14 μmoles, 16 μmoles, 18 μmoles, or 20 μmoles. The amount of PNA is from about 1 nmoles to about 60 μmoles such as about 1.0 nmoles, 3 nmoles, 6 nmoles, 9 nmoles, 12 nmoles, 15 nmoles, 18 nmoles, 21 nmoles, 24 nmoles, 27 nmoles, 30 nmoles, 40 nmoles, 50 nmoles, 100 nmoles, 150 nmoles, 200 nmoles, 250 nmoles, 300 nmoles, 350 nmoles, 400 nmoles, 500 nmoles, 600 nmoles, 700 nmoles, 800 nmoles, 900 nmoles, 1 μmole, 2 μmoles, 3 μmoles, 4 μmoles, 5 μmoles, 6 μmoles, 7 μmoles, 8 μmoles, 10 μmoles, 12 μmoles, 14 μmoles, 16 moles, 18 μmoles, 20 μmoles, 30 μmoles, 40 μmoles, 50 μmoles, or 60 μmoles. Depending on the scale of the reaction, the final volume of the reaction mixture can range from about 10 μl to about 1 mL.

In a variation of the above described synthetic protocol, the starting DNA or the PNA may be tethered to to solid support. Solvents such as dichloromethane or DMF that hydrate and swell solid supports can be added to enhance conjugation. In this case the final conjugated molecule (i.e. DNA-PNA heteropolymer) is cleaved from the support following synthesis.

Example 5

Triazole Conjugate Linker Formation (2)

Scheme 12 illustrates the synthesis of a DNA-PNA heteropolymer (component 5-3) obtained by contacting a PNA having an alkynyl functionality at the C-teminal (component 5-2) with a 5'-azide functionalized DNA (component 5-1).

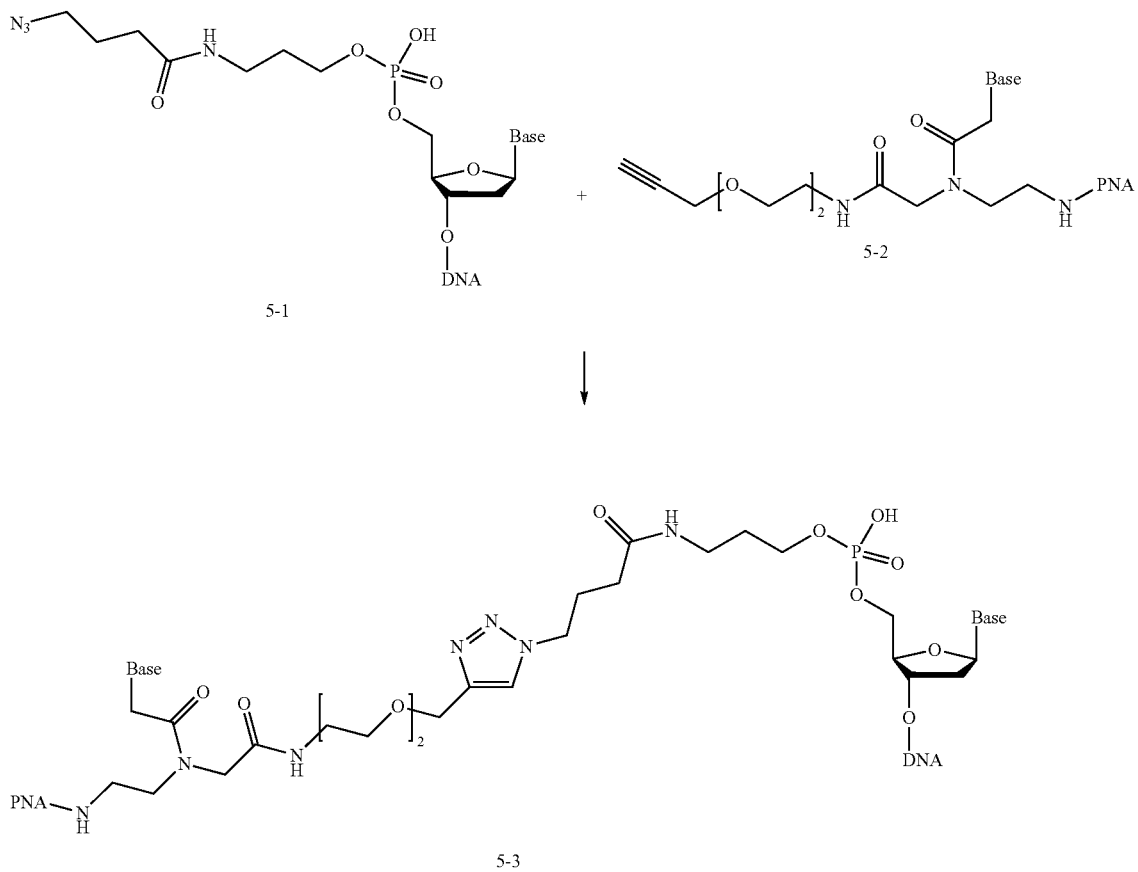

Example 6

Symmetric Conjugation Strategy Using Triazole Conjugate Linkers

An exemplary synthesis of the inventive conjugate compounds using a symmetric conjugation strategy based on the formation of triazoles as the conjugate linkers is illustrated below in Scheme 13.

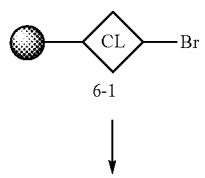

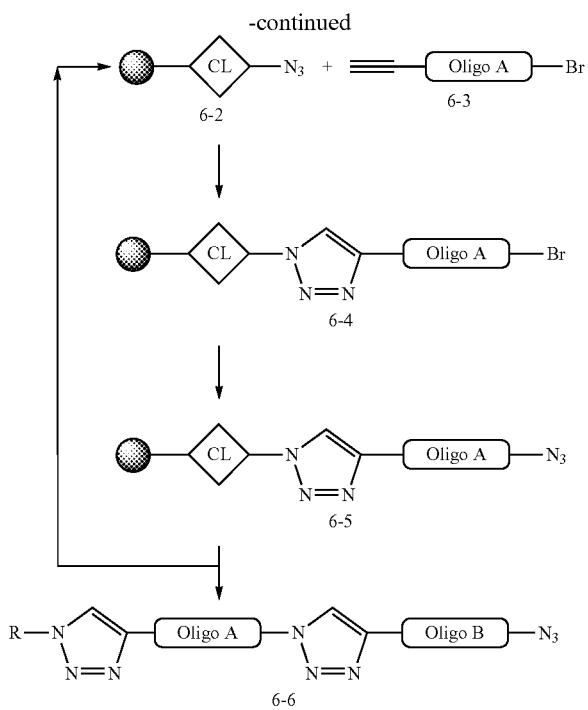

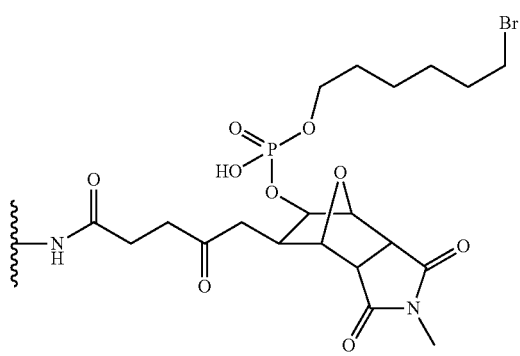 [SMILES: *NC(=O)CCC(=O)CC1C(OP(=O)(O)OCCCCCCBr)C2OC1C1C(=O)N(C)C(=O)C21]

The synthesis proceeds by contacting, a solid support 6-1 having an appropriate surface functional group, such as a bromo, a chloro, a tosylate, a mesylate, or any other suitable leaving group (a protected conjugation functionality) with an azide, (e.g., NaN$_3$), to form the azide functionalized solid support 6-2. The group "CL" conjugated to the solid support in the Scheme above can be a bicyclic molecule capable of undergoing a dephosphorylation reaction. Illustrative of a 'CL' moiety having a bicyclic core is the group illustrated below, where the ∼∼∼ indicates point to attachment to a solid support such as controlled pore glass.

This support is then contacted with a conjugation component 6-3 having the alkynyl conjugation functionality at one end and a bromo group at its other end to obtain a solid support conjugated component 6-4. After converting the bromo group of component 6-4 to an azide, conjugation functionality 6-5 can further react with a second conjugation component 6-3 to form a solid supported conjugated molecule which can be cleaved from the solid support to yield conjugated molecule 6-6. Depending on the desired size of the final product, the solid supported conjugated molecule 6-5 can react with required number of conjugation components 6-3 prior to cleavge of the product from the solid support. The conjugation components 6-3 may be the same or different, but each of these conjugation components must have an alkynyl conjugation functionality and a bromo group at their respective terminii.

Example 7

Thioether Conjugate Linker Formation (1)

DNA-PNA heteropoymers having a 5' to C-terminus connectivity via a thioether conjugate linker are synthesized by contacting a 5'-bromo modified DNA (component 7-1) with a C-terminal thiol modified PNA (component 7-2) as shown below in Scheme 14. The product is a conjugated molecule 7-3 that has an alkylthioether linkage.

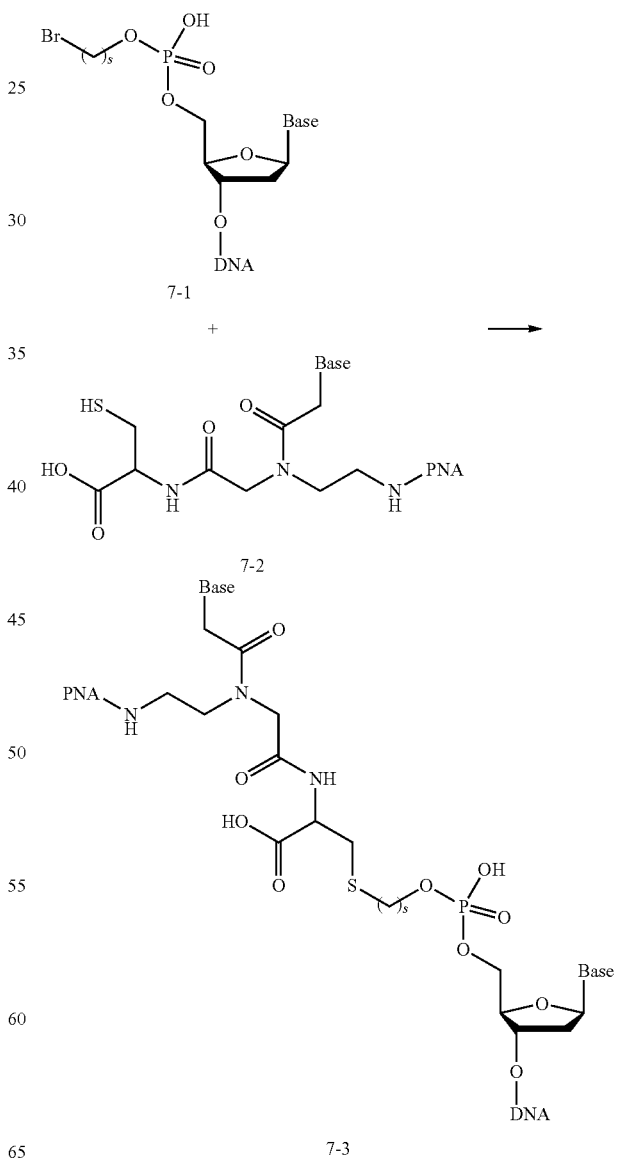

Example 8

Thioether Conjugate Linker Formation (2)

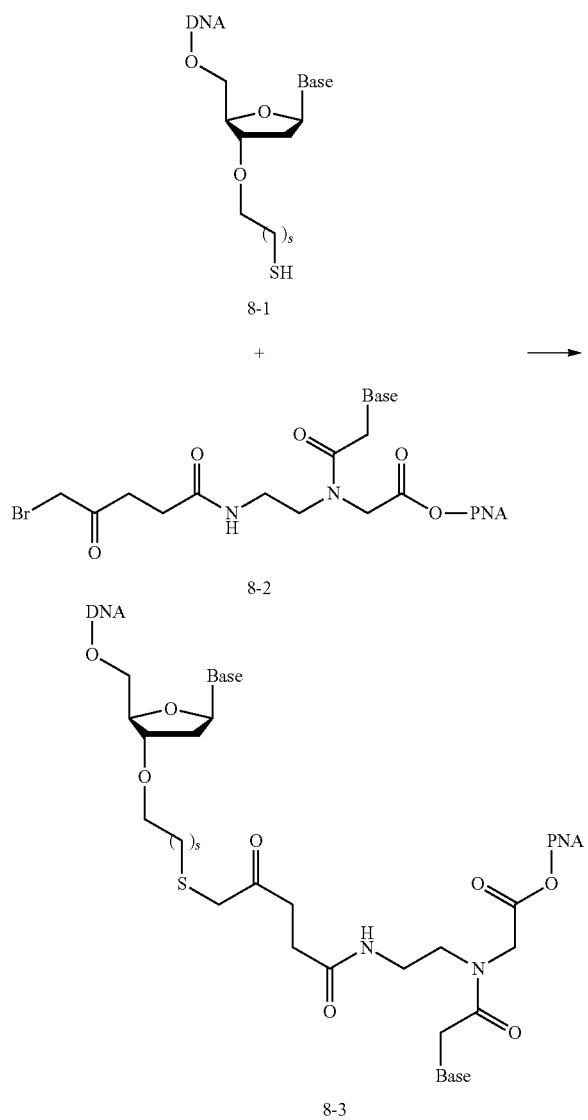

In this example a thioether conjugate linker can be formed by contacting a thiol conjugation functionality of a DNA conjugation component 8-1 with a bromo conjugation functionality of a PNA conjugation component 8-2 under conditions to give conjugated molecule 8-3.

In a variation of the protocol illustrated above the disulfide of a 3'-thiol functionalized DNA and a PNA having a N-terminal maleimide group can be used for synthesizing a DNA-PNA heteropolymer. Briefly, the 3'-functionalized DNA is dissolved in a buffer and a reductant such as DTT, TCEP, [N,N'-dimethyl-N,N'-bis(mercaptoacetyl)hydrazine (DMH), bis(2-mercaptoethyl)sulfone (BMS) or meso-2,5-dimercapto-N,N,N',N'-tetramethyladipamide (DTA) is added to the buffer solution. The amount of reductant added is greater than the amout of DNA present in the buffer solution and the reaction mixture is stirred at room temperature for about 1-2 hours. A solution of PNA in DMF is then added to the buffered solution of DNA and reductant. After stirring for 6-16 hours, the crude product is lyophilized, prior to purification using reverse-phase high performance liquid chromatography.

The mole ratio of DNA to reductant in the buffer solution can range from 1:1.2 to 1:3. The mole ratio of DNA to PNA in the reaction mixture can range from 1:0.2 to 1:5. The amount of DNA in the reaction mixture can be in the range from about 5.0 nmoles to about 20 μmoles both numbers inclusive, while the amount of PNA is from about 1 nmoles to about 100 μmoles both numbers inclusive. As described above, depending on the scale of the reaction, the final volume of the reaction mixture can range from about 10 μl to about 1 mL. The conjugation reaction can be performed using a solid support bound DNA or a solid support bound PNA. In this case the final conjugated molecule (i.e., DNA-PNA heteropolymer) is cleaved from the support following synthesis.

While particular embodiments of the subject invention have been discussed, they are illustrative only and not restrictive of the invention. A review of this specification will make many variations of the invention apparent to those skilled in the field of the invention. The full scope of the invention should be determined by reference both to the claims below, along with their full range of equivalents, and to the specification, with such variations.

What is claimed is:

1. A method of preparing a compound of the formula

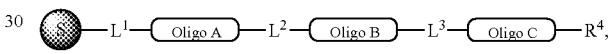

comprising
(i) attaching a conjugation component of the formula

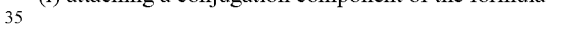

wherein $R^2$ is $R^{2a}$ or $R^{2ap}$,
to a solid support

to form a compound of the formula

(ii) when $R^2$ is $R^{2ap}$, converting

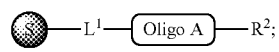

(iii) contacting

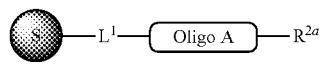

with a conjugation component of the formula

wherein R³ is R³ᵃ, or R³ᵃᵖ;
to form

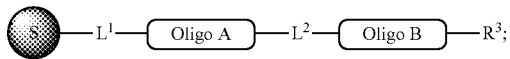

(iv) when R³ is R³ᵃᵖ, converting

to

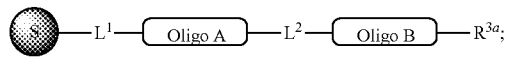

and
(v) contacting

with a conjugation component of the formula

to provide the compound of the formula

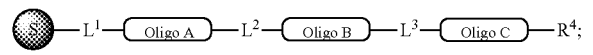

wherein:

is a solid support material;

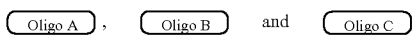

are independently an oligo, where each oligo is independently a polymer, having from 2 to about 150 covalently linked monomer units, that is characterized by a sequence of 2'-deoxyribosenucleotide residues (DNA), ribonucleotide residues (RNA), and peptide nucleic acids (PNAs), or a combination thereof;
$R^{1a}$ and $R^{1b}$ are complementary conjugation functionalities and $L^1$ is conjugate linker, and $R^{1a}$, $R^{1b}$, and $L^1$ are (a) $R^{1a}$ is azido, $R^{1b}$ is —C≡C—$R^{23}$, and $L^1$ is

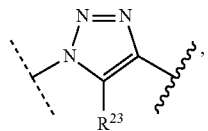

or
(b) $R^{1a}$ is —NHR²³, $R^{1b}$ is carboxy, and $L^1$ is —NR²³C(=O)—, or
(c) $R^{1a}$ is carboxy, $R^{1b}$ is —NHR²³, and $L^1$ is —C(=O)NR²³—, or
(d) $R^{1a}$ is —NHR²³, $R^{1b}$ is halo, and $L^1$ is —NR²³—, or
(e) $R^{1a}$ is —O—P(=O)(OH)(X), $R^{1b}$ is hydroxy, and $L^1$ is —O—P(=O)(OH)—O—, or
(f) $R^{1a}$ is —O—P(=O)(OH)(X), $R^{1b}$ is —NHR²³, and $L^1$ is —O—P(=O)(OH)—NR²³—, or
(g) $R^{1a}$ is —O—P(=O)(OH)(X), $R^{1b}$ is thio, and $L^1$ is —O—P(=O)(OH)—S—, or
(h) $R^{1a}$ is halo, $R^{1b}$ is thio, and $L^1$ is —S—, or
(i) $R^{1a}$ is

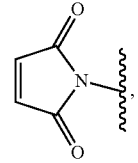

$R^{1b}$ is thio, and $L^1$ is

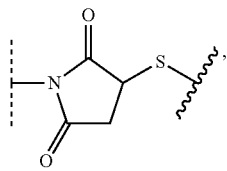

or
(j) $R^{1a}$ is —C≡C—$R^{23}$, $R^{1b}$ is azido, and $L^1$ is

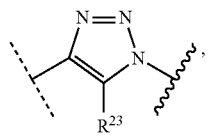

or
(k) $R^{1a}$ is halo, $R^{1b}$ is —NHR²³, and $L^1$ is —NR²³—, or
(l) $R^{1a}$ is hydroxy, $R^{1b}$ is —O—P(=O)(OH)(X), and $L^1$ is —O—P(=O)(OH)—O—, or
(m) $R^{1a}$ is —NHR²³, $R^{1b}$ is —O—P(=O)(OH)(X), and $L^1$ is —NR²³—P(=O)(OH)—O—, or
(n) $R^{1a}$ is thio, $R^{1b}$ is —O—P(=O)(OH)(X), and $L^1$ is —S—P(=O)(OH)—O—, or
(o) $R^{1a}$ is —O—P(=O)(OH)SH, $R^{1b}$ is —X, and $L^1$ is —O—P(=O)(OH)—S—, or
(p) $R^{1a}$ is —X, $R^{1b}$ is —O—P(=O)(OH)SH, and $L^1$ is —S—P(=O)(OH)—O—, or (q) $R^{1a}$ is $-(CR^{25}R^{25})_sC(=O)OR^{23}$, $R^{1b}$ is $-NHR^{23}$, $L^1$ is $-(CR^{25}R^{25})_sC(=O)NR^{23}-$, or (r) $R^{1a}$ is $-NHR^{23}$, $R^{1b}$ is $-(CR^{25}R^{25})_sC(=O)OR^{23}$, $L^1$ is $-NR^{23}C(=O)-(CR^{25}R^{25})_s-$, or (s) $R^{1a}$ is thio, $R^{1b}$ is halo, and $L^1$ is $-S-$, or (t) $R^{1a}$ is thio, $R^{1b}$ is

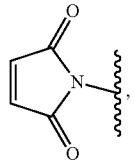 [SMILES: *N1C(=O)C=CC1=O]

and $L^1$ is

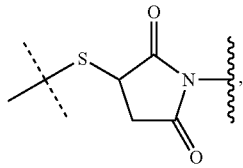

(u) $R^{1a}$ is $-SH$, $R^{1b}$ is $-O-P(=O)(OH)(O-(CH_2)_n-SH)$ and $L^1$ is $-S-S-(CH_2)_n-O-P(OH)(=O)-O-$;

$R^{2a}$ and $R^{2b}$ are complementary conjugation functionalities and $L^2$ is conjugate linker, and $R^{2ap}$, $R^{2a}$, $R^{2b}$, and $L^2$ are (a') $R^{2ap}$ is halo, $R^{2a}$ is azido, $R^{2b}$ is $-C\equiv C-R^{23}$, and $L^2$ is

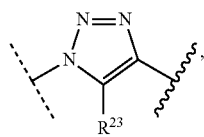

or (b') $R^{2ap}$ is $-NR^{23}Pr$, $R^{2a}$ is $-NHR^{23}$, $R^{2b}$ is carboxy, and $L^2$ is $-NR^{23}C(=O)-$, or (c') $R^{2ap}$ is carboxy ester, $R^{2a}$ is carboxy, $R^{2b}$ is $-NHR^{23}$, and $L^2$ is $-C(=O)NR^{23}-$, or (d') $R^{2ap}$ is $-NR^{23}Pr$, $R^{2a}$ is $-NHR^{23}$, $R^{2b}$ is halo, and $L^2$ is $-NR^{23}-$, or (e') $R^{2ap}$ is $-OH$, phosphate or phosphate ester, $R^{2a}$ is $-O-P(=O)(OH)(X)$, $R^{2b}$ is hydroxy, and $L^2$ is $-O-P(=O)(OH)-O-$, or (f') $R^{2ap}$ is $-OH$, phosphate or phosphate ester, $R^{2a}$ is $-O-P(=O)(OH)(X)$, $R^{2b}$ is $-NHR^{23}$, and $L^2$ is $-O-P(=O)(OH)-NR^{23}-$, or (g') $R^{2ap}$ is $-OH$, phosphate or phosphate ester, $R^{2a}$ is $-O-P(=O)(OH)(X)$, $R^{2b}$ is thio, and $L^2$ is $-O-P(=O)(OH)-S-$, or (h') $R^{2a}$ is $-X$, $R^{2b}$ is thio, and $L^2$ is $-S-$, or (i') $R^{2a}$ is

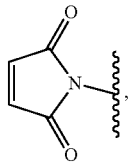 [SMILES: *N1C(=O)C=CC1=O]

$R^{2b}$ is thio, and $L^2$ is

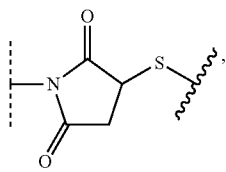

or (j') $R^{2a}$ is $-C\equiv C-R^{23}$, $R^{2b}$ is azido, and $L^2$ is

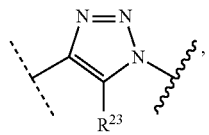

or (k') $R^{2a}$ is halo, $R^{2b}$ is $-NHR^{23}$, and $L^2$ is $-NR^{23}-$, or (l') $R^{2a}$ is hydroxy, $R^{2b}$ is $-O-P(=O)(OH)(X)$, and $L^2$ is $-O-P(=O)(OH)-O-$, or (m') $R^{2a}$ is $-NHR^{23}$, $R^{2b}$ is $-O-P(=O)(OH)(X)$, and $L^2$ is $-NR^{23}-P(=O)(OH)-O-$, or (n') $R^{2a}$ is thio, $R^{2b}$ is $-O-P(=O)(OH)(X)$, and $L^2$ is $-S-P(=O)(OH)-O-$, or (o') $R^{2ap}$ is $-O-P(=O)(OH)SR^{24}$, $R^{2a}$ is $-O-P(=O)(OH)SH$, $R^{2b}$ is $-X$, and $L^2$ is $-O-P(=O)(OH)-S-$, or (p') $R^{2a}$ is $-X$, $R^{2b}$ is $-O-P(=O)(OH)SH$, and $L^2$ is $-S-P(=O)(OH)-O-$, or (q') $R^{2a}$ is $-(CR^{25}R^{25})_sC(=O)OR^{23}$, $R^{2b}$ is $-NHR^{23}$, $L^2$ is $-(CR^{25}R^{25})_sC(=O)NR^{23}-$, or (r') $R^{2a}$ is $-NHR^{23}$, $R^{2b}$ is $-(CR^{25}R^{25})_sC(=O)OR^{23}$, $L^2$ is $-NR^{23}C(=O)-(CR^{25}R^{25})_s-$, or (s') $R^{2a}$ is thio, $R^{2b}$ is halo, and $L^2$ is $-S-$, or (t') $R^{2a}$ is thio, $R^{2b}$ is

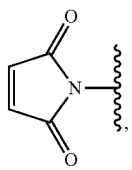

and L² is

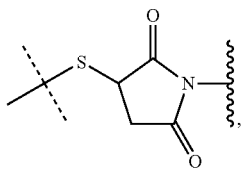

or
- (u') R²ᵃ is —SH, R²ᵇ is —O—P(=O)(OH)(O—(CH₂)ₙ—SH) and L² is —S—S—(CH₂)ₙ—O—P(OH)(=O)—O—;

R³ᵃ and R³ᵇ are complementary conjugation functionalities and L³ is conjugate linker, and R³ᵃᵖ, R³ᵃ, R³ᵇ, and L³ are
- (a") R³ᵃᵖ is halo, R³ᵃ is azido, R³ᵇ is —C≡C—R²³, and L³ is

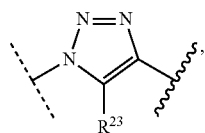

or
- (b") R³ᵃp is —NR²³Pr, R³ᵃ is —NHR²³, R³ᵇ is carboxy, and L³ is —NR²³C(=O)—, or
- (c") R³ᵃᵖ is carboxy ester, R³ᵃ is carboxy, R³ᵇ is —NHR²³, and L³ is —C(=O)NR²³—, or
- (d") R³ᵃᵖ is —NR²³Pr, R³ᵃ is —NHR²³, R³ᵇ is halo, and L³ is —NR²³—, or
- (e") R³ᵃᵖ is —OH, phosphate or phosphate ester, R³ᵃ is —O—P(=O)(OH)(X), R³ᵇ is hydroxy, and L³ is —O—P(=O)(OH)—O—, or
- (f") R³ᵃᵖ is —OH, phosphate or phosphate ester, R³ᵃ is —O—P(=O)(OH)(X), R³ᵇ is —NHR²³, and L³ is —O—P(=O)(OH)—NR²³—, or
- (g") R³ᵃᵖ is —OH, phosphate or phosphate ester, R³ᵃ is —O—P(=O)(OH)(X), R³ᵇ is thio, and L³ is —O—P(=O)(OH)—S—, or
- (h") R³ᵃ is —X, R³ᵇ is thio, and L³ is —S—, or
- (i") R³ᵃ is

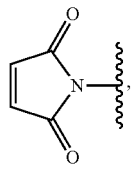

R³ᵇ is thio, and L³ is

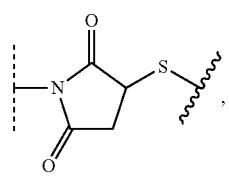

or
- (j") R³ᵃ is —C≡C—R²³, R³ᵇ is azido, and L³ is

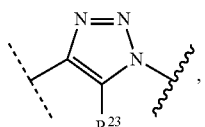

or
- (k") R³ᵃ is halo, R³ᵇ is —NHR²³, and L³ is —NR²³—, or
- (l") R³ᵃ is hydroxy, R²ᵇ is —O—P(=O)(OH)(X), and L³ is —O—P(=O)(OH)—O—, or
- (m") R³ᵃ is —NHR²³, R³ᵇ is —O—P(=O)(OH)(X), and L³ is —NR²³—P(=O)(OH)—O—, or
- (n") R³ᵃ is thio, R³ᵇ is —O—P(=O)(OH)(X), and L³ is —S—P(=O)(OH)—O—, or
- (o") R³ᵃᵖ is —O—P(=O)(OH)SR²⁴, R³ᵃ is —O—P(=O)(OH)SH, R³ᵇ is —X, and L³ is —O—P(=O)(OH)—S—, or
- (p") R³ᵃ is —X, R³ᵇ is —O—P(=O)(OH)SH, and L³ is —S—P(=O)(OH)—O—, or
- (q") R³ᵃ is —(CR²⁵R²⁵)ₛC(=O)R²³, R³ᵇ is —NHR²³, L³ is —(CR²⁵R²⁵)ₛC(=O)NR²³—, or
- (r") R³ᵃ is —NHR²³, R³ᵇ is —(CR²⁵R²⁵)ₛC(=O)R²³, L³ is —NR²³C(=O)—(CR²⁵R²⁵)ₛ—, or
- (s") R³ᵃ is thio, R³ᵇ is —X, and L³ is —S—, or
- (t") R³ᵃ is thio, R³ᵇ is

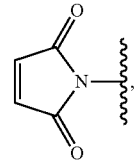

and L³ is

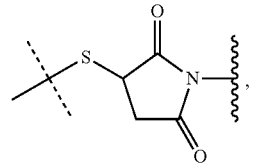

or
- (u") R³ᵃ is —SH, R³ᵇ is —O—P(=O)(OH)(O—(CH₂)ₙ—SH) and L³ is —S—S—(CH₂)ₙ—O—P(OH)(=O)—O—;

R⁴ is selected from the group consisting of R³ᵃ, R³ᵃᵖ, halo, —NR²³Pr, —OH, —O—P(=O)(OH)SR²⁴, carboxy ester, phosphate, phosphate ester, azido, —C≡C—R²³, —NHR²³, carboxy, hydroxy, —(CR²⁵R²⁵)ₛC(=O)OR²³, —O—P(=O)(OH)SH, or —O—P(=O)(OH)Br, or an oligo;

X is chlorine, bromine, fluorine, tosylate, mesylate, triflate, or dimethoxy triflate, n is 1, 2, 3, 4, 5, or 6;

R²³ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloalkynyl, substituted cycloalkynyl, heteroaryl, substituted heteroaryl, heterocyclic, and substituted heterocyclic;

Pr is an amino protecting group;
$R^{24}$ is trityl or benzyl;
$R^{25}$ is hydrogen or $C_{1-6}$ alkyl;
n is 1, 2, 3, 4, 5, or 6;
s is an integer of greater than 1;
provided that $R^2$ does not react with $R^{1a}$ or $R^{1b}$, $R^3$ does not react with $R^{2a}$ or $R^{2b}$ and $R^4$ does not react with $R^{3a}$ or $R^{3b}$;
- - - represents the point of connection to the part of the solid support-bound conjugated molecule that is closer to

, and ∿∿∿ represents the point of connection to the part of the solid support-bound conjugated molecule that is further away from

.

2. The method of claim 1 for preparing a compound of the formula

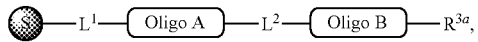

comprising
(i) attaching a compound of the formula

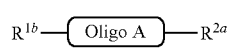

to a solid support

to form a compound of the formula

and (iii) reacting

with a compound of the formula

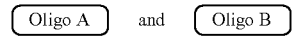

to form

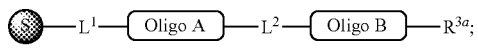

wherein:

is a solid support material;

Oligo A and Oligo B are independently an oligo;
$R^{1a}$ and $R^{1b}$ are complementary conjugation functionalities and $L^1$ is conjugate linker, $R^{2a}$ and $R^{2b}$ are complementary conjugation functionalities and $L^2$ is conjugate linker, and $R^{1a}$, $R^{1b}$, $L^1$, $R^{2a}$, $R^{2b}$, $L^2$, and $R^{3a}$ are selected from

| $R^{1a}$, $R^{2a}$, or $R^{3a}$ | $R^{1b}$ or $R^{2b}$ | $L^1$ or $L^2$ |
|---|---|---|
| —C≡C—$R^{23}$ | azido | triazole with $R^{23}$ |
| azido | —C≡C—$R^{23}$ | triazole with $R^{23}$ |
| carboxy | —NHR$^{23}$ | —C(=O)NR$^{23}$— |
| —NHR$^{23}$ | carboxy | —NR$^{23}$C(=O)— |
| halo | —NHR$^{23}$ | —NR$^{23}$— |
| —NR$^{23}$ | halo | —NR$^{23}$— |
| hydroxy | —O—P(=O)(OH)(X) | —O—P(=O)(OH)—O— |
| —O—P(=O)(OH)(X) | hydroxy | —O—P(=O)(OH)—O— |
| —NHR$^{23}$ | —O—P(=O)(OH)(X) | —NR$^{23}$—P(=O)(OH)—O— |
| —O—P(=O)(OH)(X) | —NHR$^{23}$ | —O—P(=O)(OH)—NR$^{23}$— |

-continued

| $R^{1a}$, $R^{2a}$, or $R^{3a}$ | $R^{1b}$ or $R^{2b}$ | $L^1$ or $L^2$ |
|---|---|---|
| thio | —O—P(=O)(OH)(X) | —S—P(=O)(OH)—O— |
| —O—P(=O)(OH)(X) | thio | —O—P(=O)(OH)—S— |
| thio | —X | —S— |
| —X | thio | —S— |
| —O—P(=O)(OH)SH | —X | —O—P(=O)(OH)—S— |
| —X | —O—P(=O)(OH)SH | —S—P(=O)(OH)—O— |
| —(CR$^{25}$R$^{25}$)$_s$C(=O)OR$^{23}$ | —NHR$^{23}$ | —(CR$^{25}$R$^{25}$)$_s$C(=O)NR$^{23}$— |
| —NHR$^{23}$ | —(CR$^{25}$R$^{25}$)$_s$C(=O)OR$^{23}$ | —NR$^{23}$C(=O)—(CR$^{25}$R$^{25}$)$_s$— |
| thio | 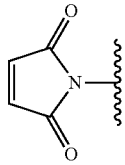 [SMILES: *N1C(=O)C=CC1=O] | 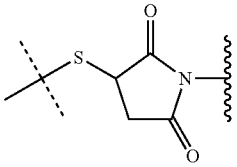 |
| 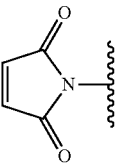 | thio | 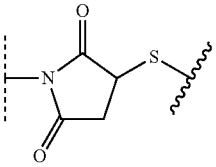 |
| —SH | —O—P(=O)(OH)(O—(CH$_2$)$_n$—SH) | —S—S—(CH$_2$)$_n$—O—P(OH)(=O)—O— | wherein the selection of $R^{1a}$, $R^{2a}$, or $R^{3a}$ is independent of each other provided that $L^1$ and $L^2$ are different, $R^{2a}$ does not react with $R^{1a}$ or $R^{1b}$, and $R^{3a}$ does not react with $R^{2a}$ or $R^{2b}$;

X is chlorine, bromine, fluorine, tosylate, mesylate, triflate, or dimethoxy triflate;

$R^{23}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloalkynyl, substituted cycloalkynyl, heteroaryl, substituted heteroaryl, heterocyclic, and substituted heterocyclic;

$R^{25}$ is hydrogen or C$_{1-6}$ alkyl;

s is an integer of greater than 1;

- - - represents the point of connection to the part of the solid support-bound conjugated molecule that is closer to

, and ∿∿∿ represents the point of connection to the part of the solid support-bound conjugated molecule that is further away from

.

3. A method of preparing a compound of the formula

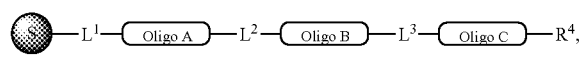

comprising
cleaving the bond between

and $L^1$ of the compound of the formula

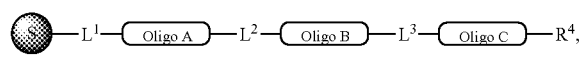

thereby obtaining

wherein:
the compound of

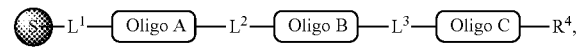

is prepared according to the method of claim 1;

$L^1$, $L^2$, $R^3$, $R^4$,

Oligo A, Oligo B and Oligo C are as defined in claim 1; and

Z is —OH, OH—$(C_1$-$C_{10})$alkylene-, —COOH, $NH_2C(O)$—, $NH_2NH$—C(O)—, COOH—$(C_1$-$C_{10})$alkylene-, $NH_2C(O)$—$(C_1$-$C_{10})$alkylene-, $NH_2NH$—C(O)—$(C_1$-$C_{10})$alkylene-, $CH_2$=CH—$(C_1$-$C_{10})$alkylene-, C≡C—$(C_1$-$C_{10})$alkylene- or HS—$(C_1$-$C_{10})$alkylene- and any alkylene is optionally substituted by one or more groups selected from —OH, halogen, —NHR'', —NHC(O)—$(C_1$-$C_{10})$alkylene-C≡CH, and —NHC(O)—$(C_1$-$C_{10})$alkylene-CH=$CH_2$;

R'' is selected from $(C_1$-$C_{10})$alkyl, $(C_3$-$C_{10})$cycloalkyl, or $(C_3$-$C_{10})$aryl.

4. The method of claim 1, wherein the method further comprises preparing a compound of the formula

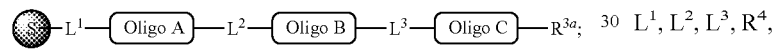

comprising
(i) converting the compound of formula

to

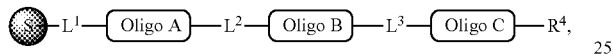

and
(ii) contacting

with a conjugation component of the formula

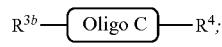

wherein steps (i) and (ii) are performed a sufficient number of times to provide the compound of the formula

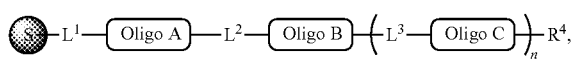

wherein:
n is an integer between 2 and 25, and

$L^1$, $L^2$, $R^{3a}$, $R^4$,

Oligo A, Oligo B, and Oligo C are as defined in claim 1.

5. A method for preparing a compound of the formula

comprising cleaving a compound of formula

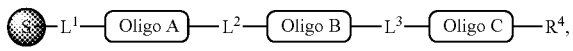

from the solid support, wherein

Z is —OH, OH—$(C_1$-$C_{10})$alkylene-, —COOH, $NH_2C(O)$—, $NH_2NH$—C(O)—, COOH—$(C_1$-$C_{10})$alkylene-, $NH_2C(O)$—$(C_1$-$C_{10})$alkylene-, $NH_2NH$—C(O)—$(C_1$-$C_{10})$alkylene-, $CH_2$=CH—$(C_1$-$C_{10})$alkylene-, C≡C—$(C_1$-$C_{10})$alkylene- or HS—$(C_1$-$C_{10})$alkylene- and the alkylene can be optionally substituted by one or more groups selected from —OH, halogen, —NHR'', —NHC(O)—$(C_1$-$C_{10})$alkylene-C≡CH, or —NHC(O)—$(C_1$-$C_{10})$alkylene-CH=$CH_2$;

R'' is $(C_1$-$C_{10})$alkyl, $(C_3$-$C_{10})$cycloalkyl, or $(C_3$-$C_{10})$aryl; and

$L^1$, $L^2$, $L^3$, $R^4$,

Oligo A, Oligo B, and Oligo C are as defined in claim 1.

6. A method for preparing a compound of the formula

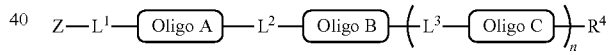

comprising cleaving a compound of formula

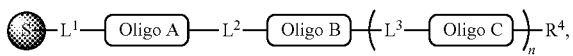

from

wherein

Z is —OH, OH—$(C_1$-$C_{10})$alkylene-, —COOH, $NH_2C(O)$—, $NH_2NH$—C(O)—, COOH—$(C_1$-$C_{10})$alkylene-, $NH_2C(O)$—$(C_1$-$C_{10})$alkylene-, $NH_2NH$—C(O)—$(C_1$-$C_{10})$alkylene-, $CH_2$=CH—$(C_1$-$C_{10})$alkylene-, C≡C—$(C_1$-$C_{10})$alkylene- or HS—$(C_1$-$C_{10})$alkylene- and the alkylene can be optionally substituted by one or more groups selected from —OH, halogen, —NHR'', —NHC(O)—$(C_1$-$C_{10})$alkylene-C≡CH, or —NHC(O)—$(C_1$-$C_{10})$alkylene-CH=$CH_2$;

R'' is $(C_1$-$C_{10})$alkyl, $(C_3$-$C_{10})$cycloalkyl, or $(C_3$-$C_{10})$aryl; and n,

, $L^1, L^2, L^3, L^4$,

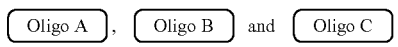

are as defined in claim 4.

7. A method of preparing a compound of the formula

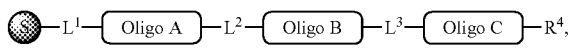

comprising
(i) attaching a conjugation component of the formula

wherein $R^2$ is $R^{2a}$ or $R^{2ap}$,
to a solid support

to form a compound of the formula

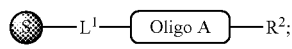

(ii) when $R^2$ is $R^{2ap}$, converting

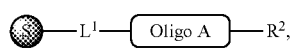

to

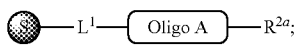

(iii) contacting

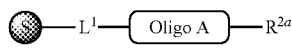

with a conjugation component of the formula

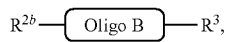

wherein $R^3$ is $R^{3a}$, or $R^{3ap}$;

to form

(iv) when $R^3$ is $R^{3ap}$, converting

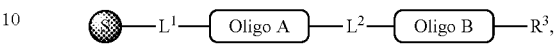

to

and
(v) contacting

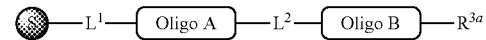

with a conjugation component of the formula

to provide the compound of the formula

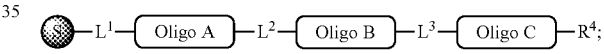

wherein:

is a solid support material;

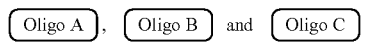

are independently an oligo, where each oligo is independently a polymer, having from 2 to about 150 covalently linked monomer units, that is characterized by a sequence of 2'-deoxyribosenucleotide residues (DNA), ribonucleotide residues (RNA), and peptide nucleic acids (PNAs), or a combination thereof;
wherein
(a) $R^{1a}$ is azido, $R^{1b}$ is $-C{\equiv}C-R^{23}$, and $L^1$ is

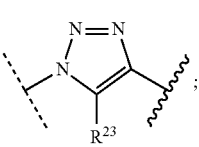

(a') $R^{2ap}$ is halo, $R^{2a}$ is azido, $R^{2b}$ is —C≡C—$R^{23}$, and $L^2$ is

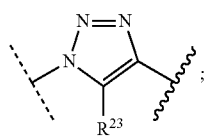

(a'') $R^{3ap}$ is halo, $R^{3a}$ is azido, $R^{3b}$ is —C≡C—$R^{23}$, and $L^3$ is

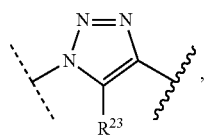

or $R^4$ is selected from the group consisting of $R^{3a}$, $R^{3ap}$, halo, —$NR^{23}Pr$, —OH, —O—P(=O)(OH)$SR^{24}$, carboxy ester, phosphate, phosphate ester, azido, —C≡C—$R^{23}$, —$NHR^{23}$, carboxy, hydroxy, —$(CR^{25}R^{25})_sC(=O)OR^{23}$, —O—P(=O)(OH)SH, or —O—P(=O)(OH)Br, or an oligo;

n is 1, 2, 3, 4, 5, or 6;

$R^{23}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, cycloalkynyl, substituted cycloalkynyl, heteroaryl, substituted heteroaryl, heterocyclic, and substituted heterocyclic;

Pr is an amino protecting group;

$R^{24}$ is trityl or benzyl;

$R^{25}$ is hydrogen or $C_{1-6}$ alkyl;

s is an integer of greater than 1;

provided that $R^2$ does not react with $R^{1a}$ or $R^{1b}$, $R^3$ does not react with $R^{2a}$ or $R^{2b}$ and $R^4$ does not react with $R^{3a}$ or $R^{3b}$;

- - - represents the point of connection to the part of the solid support-bound conjugated molecule that is closer to

, and ⌇⌇⌇ represents the point of connection to the part of the solid support-bound conjugated molecule that is further away from

.

8. The method of claim 7, wherein the method further comprises preparing a compound of the formula

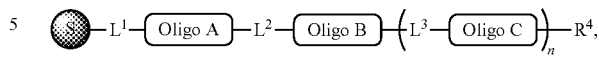

comprising
(i) converting the compound of formula

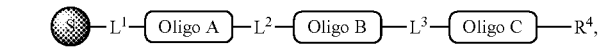

to

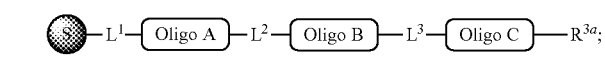

(ii) when $R^3$ is $R^{3ap}$, converting

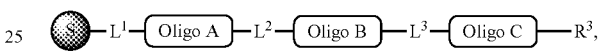

to

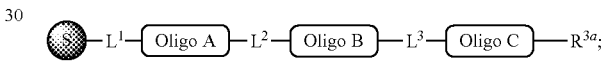

and
(iii) contacting

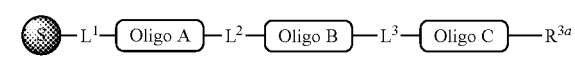

with a conjugation component of the formula

wherein steps (i), (ii) and (iii) are performed a sufficient number of times to provide the compound of the formula

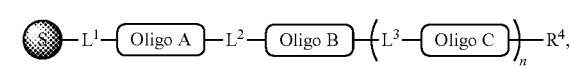

wherein:
n is an integer between 2 and 25, and

, $L^1$, $L^2$, $L^{3a}$, $R^{3b}$, $R^4$,

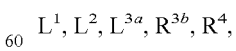

are as defined in claim 7.

* * * * *